(12) United States Patent
Qin

(10) Patent No.: US 11,542,283 B2
(45) Date of Patent: Jan. 3, 2023

(54) SYNTHESIS OF PEPTIDE BORATE ESTER COMPOUND AND USE THEREOF

(71) Applicant: JIANGSU CHIA TAI FENGHAI PHARMACEUTICAL CO., LTD., Jiangsu (CN)

(72) Inventor: Yanru Qin, Jiangsu (CN)

(73) Assignee: JIANGSU CHIA TAI FENGHAI PHARMACEUTICAL CO., LTD., Jiangsu (CN)

( * ) Notice: Subject to any disclaimer, the term of this patent is extended or adjusted under 35 U.S.C. 154(b) by 0 days.

(21) Appl. No.: 17/059,066

(22) PCT Filed: May 27, 2019

(86) PCT No.: PCT/CN2019/088506
§ 371 (c)(1),
(2) Date: Nov. 25, 2020

(87) PCT Pub. No.: WO2019/228299
PCT Pub. Date: Dec. 5, 2019

(65) Prior Publication Data
US 2021/0214377 A1    Jul. 15, 2021

(30) Foreign Application Priority Data
May 28, 2018  (CN) .......................... 201810524104.0

(51) Int. Cl.
*C07F 5/04* (2006.01)
*A61P 35/00* (2006.01)

(52) U.S. Cl.
CPC ............... *C07F 5/04* (2013.01); *A61P 35/00* (2018.01)

(58) Field of Classification Search
CPC ...................................................... C07F 5/04
See application file for complete search history.

(56) References Cited

U.S. PATENT DOCUMENTS 9,340,559 B2 * 5/2016 Ruggeri ................ A61K 45/06
2012/0289699 A1   11/2012 Henschke et al.

FOREIGN PATENT DOCUMENTS

| CN | 101094648 A | 12/2007 |
|----|-------------|---------|
| CN | 103304629 A | 9/2013 |
| CN | 103539832 A | 1/2014 |
| CN | 105732683 A | 7/2016 |
| CN | 107400142 A | 11/2017 |
| WO | WO 2002/059130 A1 | 8/2002 |
| WO | WO 2014/072985 A1 | 5/2014 |
| WO | WO 2019/228299 A1 | 12/2019 |

OTHER PUBLICATIONS

Hou, D. et al. "Bortezomib Congeners Induce Apoptosis ot Hepatocellular Carcinoma via CIP2A Inhibition," *Molecules*, vol. 18, pp. 15398-15411 (2013).
International Search Report, dated Aug. 27, 2019 in connection with PCT International Application No. PCT/CN2019/088506.
Geurink, P.P. et al. "Incorporation of Fluorinated Phenylalanine Generates Highly Specific Inhibitor of Proteasome's Chymotrypsin-like Sites," *J. Med. Chem.* vol. 54, pp. 2319-2323 (2010).
Lei, M. et al. "3D-QSAR-aided Design, Synthesis, In Vitro and In Vivo Evaluation of Dipeptidyl Boronic Acid Proteasome Inhibitors and Mechanism Studies," *Bioorganic & Medicinal Chemistry Letters.* vol. 24, pp. 2576-2588 (2016).
Shi, J et al. "Design, Synthesis and Docking Studies of Novel Dipeptidyl Boronic Acid Proteasome Inhibitors Constructed from αα- and αβ-Amino Acids," *Bioorganic & Medicinal Chemistry Letters.* vol. 26, pp. 1958-1962 (2016).
Written Opinion (form PCT/ISA/237) dated Aug. 27, 2019 in connection with PCT International Application No. PCT/CN2019/088506.

* cited by examiner

*Primary Examiner* — Golam M Shameem
(74) *Attorney, Agent, or Firm* — Gary J. Gershik

(57) ABSTRACT

Provided are a peptide borate ester compound or a pharmaceutically acceptable salt thereof, a preparation method therefor, and pharmaceutical use thereof. The peptide borate ester compound or pharmaceutically acceptable salt thereof has a structure as shown in Formula (I), and is useful in the preparation of proteasome inhibitors to treat solid tumors and hematoma.

8 Claims, 1 Drawing Sheet

SYNTHESIS OF PEPTIDE BORATE ESTER COMPOUND AND USE THEREOF

CROSS-REFERENCE TO RELATED APPLICATIONS

This application is a § 371 national stage of PCT International Application No. PCT/CN2019/088506, filed May 27, 2019, claiming priority of Chinese Patent Application No. 201810524104.0, filed May 28, 2018, the contents of each of which are hereby incorporated by reference herein.

BACKGROUND

Technical Field

The present invention relates to the technical field of drug synthesis, and particularly to a method for preparing a series of novel peptide borate ester compounds and use thereof in pharmacodynamics.

Related Art

At present, cancers are one of the major diseases that endanger human health. Although the existing treatments for cancers have achieved great progress in operative treatment, chemotherapy, and radiotherapy, cancers still cannot be cured radically. The currently marketed anti-cancer drugs have certain therapeutic effects, but they suffer from serious side effects. Therefore, in-depth discussion and research on how to study targeting new anticancer drugs starting from effective tumor targets has become a top priority for medical workers.

The Ubiquitin-Proteasome Pathway (UPP) is a main pathway for the degradation of intracellular protein systems, which participates in many physiologically important cellular processes, including signal transduction, immune response, unfolded protein response and cell cycle progress. This pathway is greatly associated with the onset of cardiovascular and cerebrovascular diseases, cancers, and neurodegenerative diseases. Using some effective inhibitors to inhibit the excessive degradation of important proteins in this pathway will provide new ideas for the treatment of the aforementioned diseases. For this new target, the first proteasome inhibitor bortezomib (PS-341) was approved by the FDA in 2003 for the treatment of recurrent myeloma. In 2004, the drug was approved to be marketed in the European Union for the treatment of multiple myeloma. In September 2005, the drug was introduced by Xi'an Janssen, and marked initially in Guangzhou, China. In 2005, the drug won the "PrixGalien" award, which is considered as the Nobel Prize in the pharmaceutical industry, in France, Netherland and Belgium. On Jul. 11, 2007, it was approved by the FDA for the treatment of relapsed or refractory mantle cell lymphoma (MCL), becoming the only drug approved by the FDA for the treatment of MCL. Velcade was approved by the FDA for subcutaneous administration, which not only makes the absorption of Velcade easier, but also greatly improves the patient's tolerance to Velcade and reduces the side effects.

In 2014, Velcade's sales reached US$3.069 billion and became one of the top 20 best-selling anti-tumor drugs in the world. The price of Velcade in the Chinese market is about 13,000 yuan per 3.5 mg, and the cost for one course of treatment is about 40,000 yuan. Such a high expense is a very heavy economic burden for many patients. Moreover, current clinical data shows that this drug also has more side effects, such as fatigue, nausea, diarrhea, and neuropathy. Therefore, how to develop a potent proteasome inhibitor drug with low price and low toxic and side effects is a problem that urgently need to solved at present.

For this confirmed target, a series of peptide borate ester compounds with novel structure are designed as proteasome inhibitors.

SUMMARY

An object of the present invention is to synthesize a series of novel peptide borate ester compounds with a new structure and proteasome inhibitory function that can be taken orally. As 20S proteasome inhibitors, they can effectively block the proliferation of tumor cells and induce tumor cell apoptosis, thus being useful in the prevention and treatment of various human and animal diseases such as malignant tumors.

Another object of the present invention is to provide a pharmaceutical composition comprising a pharmaceutical carrier and a peptide borate ester compound of the present invention, optionally combined with one or more other therapeutic agents simultaneously, separately or sequentially.

Another object of the present invention is to provide use of the peptide borate ester compound in the preparation of proteasome inhibitors.

Another object of the present invention is to provide use of the peptide borate ester compound in the preparation of anti-tumor drugs. The tumors mentioned in the present invention include solid tumors, selected from non-small cell lung cancer, small cell lung cancer, lung adenocarcinoma, lung squamous cell carcinoma, pancreatic cancer, breast cancer, prostate cancer, liver cancer, skin cancer, epithelial cell carcinoma, gastrointestinal stromal tumor, or nasopharyngeal carcinoma; and hematoma, selected from leukemia, multiple myeloma, mantle cell lymphoma or histiocytic lymphoma.

Another object of the present invention is to provide a method for preparing the peptide borate ester compound.

The objects of the present invention can be achieved by the following solutions:

A peptide borate ester compound or a pharmaceutically acceptable salt thereof has a structure as shown in Formula I:

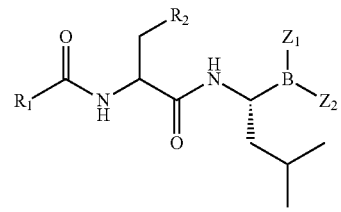

where $R_1$ is selected from $C_{1-10}$ alkyl, $C_{1-10}$ alkoxy, $C_{1-10}$ alkoxy$C_{1-10}$ alkyl, $C_{3-6}$ cycloalkyl, phenyl, naphthyl, tetrahydronaphthyl, 2,5-dichlorophenyl or heterocyclyl, which is optionally substituted with $C_{1-14}$ alkyl, $C_{1-14}$ alkoxy, $C_{1-4}$ cycloalkyl, halo or $C_{1-4}$ haloalkyl; and $R_1$ is preferably $C_{1-10}$ alkyl, $C_{1-10}$ alkoxy, $C_{1-10}$ alkoxymethyl, $C_{1-10}$ alkoxyethyl, $C_{3-6}$ cycloalkyl, phenyl, 2,5-dichlorophenyl, pyrazinyl, pyridyl, naphthyl, tetrahydronaphthyl, oxazolyl or isoxazolyl, which is optionally substituted with $C_{1-14}$ alkyl, $C_{1-14}$ alkoxy, halo or $C_{1-4}$ haloalkyl;

further, $R_1$ is preferably

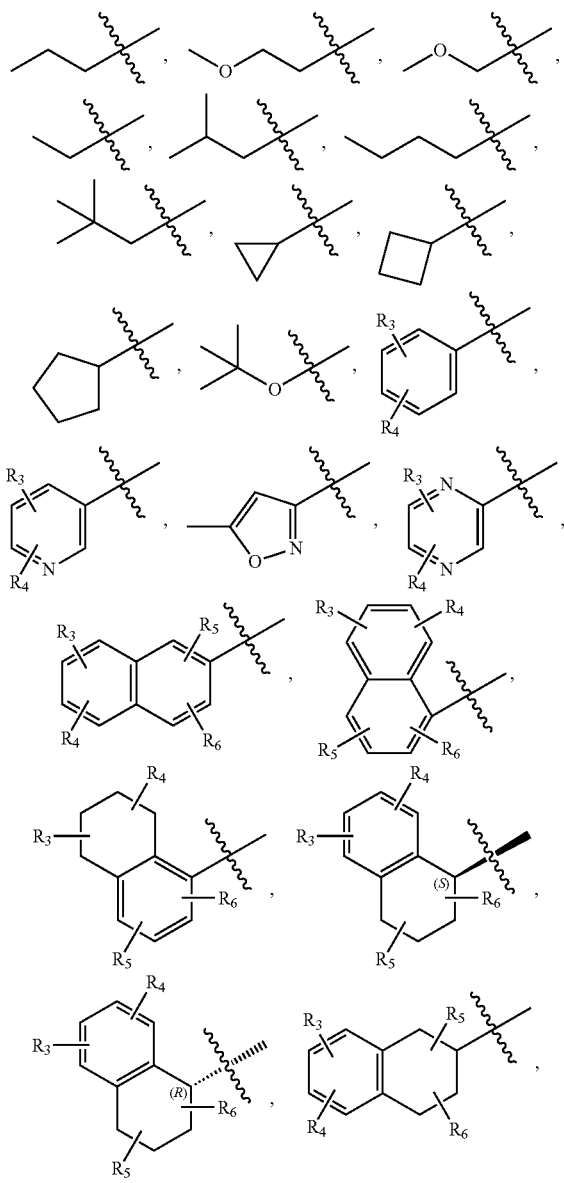

in which $R_3$, $R_4$, $R_5$ and $R_6$ are independently selected from hydrogen, methyl, methoxy, ethyl, ethoxy, chloro, bromo, fluoro, or trifluoromethyl;

R2 is selected from H, phenyl, methoxy, methylthio, cyclohexyl, or 2,3-dihydro-1,4-benzodioxole, which is optionally substituted with one or more $C_{1-4}$ alkyl, $C_{1-4}$ alkoxy, nitro, halo, or trifluoromethyl;

$R_2$ is selected from H, phenyl, methoxy, methylthio, cyclohexyl, or 2,3-dihydro-1,4-benzodioxole, which is optionally substituted with one or more $C_{1-4}$ alkyl, $C_{1-4}$ alkoxy, nitro, halo, or trifluoromethyl;

B, $Z_1$ and $Z_2$, form a heterocyclyl group containing N, S or O together, or B, together with $Z_1$ and $Z_2$, forms a group bearing an O containing heterocyclyl group, where the oxygen atom is attached to the boron atom; preferably, B, $Z_1$ and $Z_2$ form a borate-α-pinanediol ester together, or B, together with $Z_1$ and $Z_2$, forms a borate, where the oxygen atom is attached to the boron atom; and further preferably, B, $Z_1$ and $Z_2$ form a borate-α-pinanediol ester together, or B, $Z_1$ and $Z_2$ form a diethanolamine borate, a citrate borate, a tartrate borate, a malate borate, an α-hydroxyglutarate borate, and other prodrugs such as glucose borate formed with the ortho-hydroxyl structure of glucose together.

In the present invention, the term "optionally substituted with . . . " with reference to $R_1$ and $R_2$ means that $R_1$ and $R_2$ may be unsubstituted or substituted with these groups, that is, they are not limited to the situation where they are substituted with the listed groups, but also include the situation where they are not substituted with the listed groups. This expression is similar to the expression "$R_1$ is substituted or unsubstituted $C_{1-10}$ alkyl, $C_{3-6}$ cycloalkyl or heterocycloalkyl, phenyl, naphthyl or indolyl, where the substituent is $C_{1-4}$ alkyl, $C_{1-4}$ alkoxy, cyano, hydroxyl, mercapto, amino or halo". Here, the scope defined by term substituted or unsubstituted doesn't narrowly include $C_{1-10}$ alkyl, but also expands to all the groups mentioned, including substituted or unsubstituted $C_{3-6}$ cycloalkyl or heterocycloalkyl, substituted or unsubstituted benzyl, substituted or unsubstituted naphthylmethyl, substituted or unsubstituted indolylmethyl, where the substituent is $C_{1-4}$ alkyl, $C_{1-4}$ alkoxy, cyano, hydroxyl, mercapto, amino or halo.

The term "alkyl" is used to indicate a saturated hydrocarbon group, the $C_{1-10}$ alkyl refers to a saturated hydrocarbon group containing 1 to 10 carbon atoms, and the $C_{1-4}$ alkyl refers to a saturated hydrocarbon group containing 1 to 4 carbon atoms.

The term "cycloalkyl" refers to non-aromatic carbocyclic groups, including cyclized alkyl groups. Cycloalkyl can include bicyclic or polycyclic ring systems. Examples of cycloalkyl include cyclopropyl, cyclobutyl, cyclopentyl, cyclohexyl, and cycloheptyl, and the $C_{3-6}$ cycloalkyl refers to a cycloalkyl group containing 3 to 6 carbon atoms.

The term "benzyl" refers to phenylmethyl, and the substituted benzyl refers to the substitution of at least one hydrogen atom on the benzene ring of the benzyl group with a non-hydrogen moiety. The substituent to the benzyl group may be halo, —CN, —OH, —SH, —NH$_2$, a linear or branched $C_{1-6}$ alkyl, or a substituted linear or branched $C_{1-6}$ alkyl.

The term "heterocycloalkyl" refers to non-aromatic heterocarbocyclic groups, including cyclized alkyl groups, in which one or more ring-forming carbon atoms are replaced by a heteroatom such as O, N or S atom. The heterocycloalkyl preferably has 3, 4, 5, 6 or 7 ring-forming atoms.

The term "heterocyclyl" refers to cyclic groups containing a heteroatom such as O, N or S, including aromatic heterocyclyl groups or non-aromatic heterocyclyl groups, such as furyl, thiophenyl, pyrrolyl, thiazolyl, imidazolyl, pyridinyl, pyridazinyl, pyrimidinyl, pyrazinyl, quinolinyl, isoquinolinyl, indolyl, benzofuryl, purinyl, acridinyl, oxazolyl, and isooxazolyl.

"1-Naphthylmethyl" refers to

"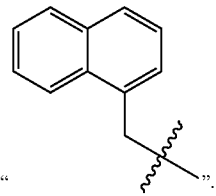 [SMILES: *Cc1cccc2ccccc12]".

"2-Naphthylmethyl" refers to

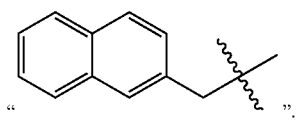 [SMILES: *Cc1ccc2ccccc2c1]

"Indolylmethyl" refers to

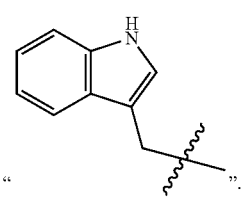 [SMILES: *Cc1c[nH]c2ccccc12]

"2,3-dihydro-1,4-benzodioxole" refers to

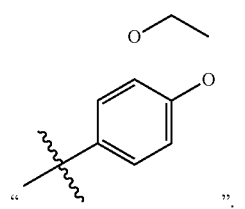

"Tetrahydronaphthyl" refers to

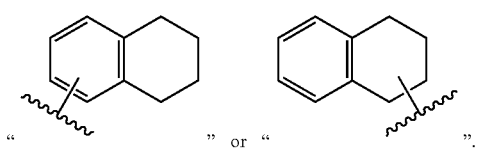

"Oxazolyl" refers to

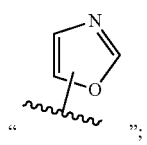

and "isoxazolyl" refers to

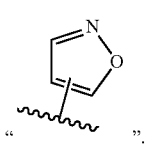

"Diethanolamine borate" refers to

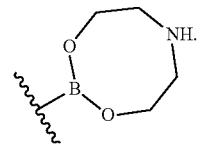 [SMILES: *B1OCCNCCO1]

"Citrate borate" refers to

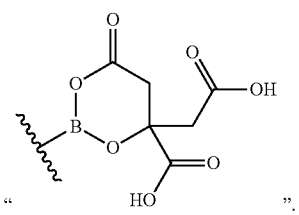 [SMILES: *B1OC(=O)CC(CC(=O)O)(C(=O)O)O1]

"Tartrate borate" refers to

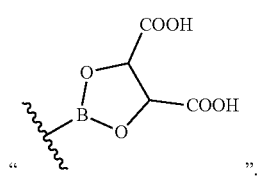 [SMILES: *B1OC(C(=O)O)C(C(=O)O)O1]

Please replace the paragraph on page 7 at lines 1-7 of the specification with the following amended paragraph:

"Malate borate" refers to

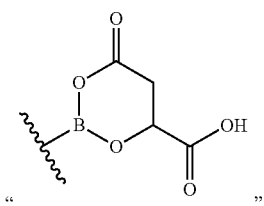 [SMILES: *B1OC(=O)CC(C(=O)O)O1]

"Alpha-hydroxy-glutarate borate" refers to

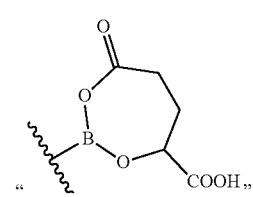 [SMILES: *B1OC(=O)CCC(C(=O)O)O1]

"Glucose borate" refers to

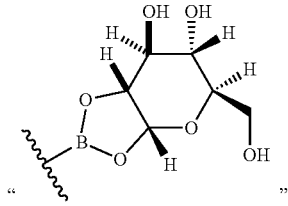 [SMILES: *B1O[C@H]2O[C@H](CO)[C@@H](O)[C@H](O)[C@H]2O1]

"

"

"Alkoxy" refers to the —O-alkyl group, having generally 1 to 10 carbo atoms. Examples of alkoxy include methoxy, ethoxy, propoxy (e.g., n-propoxy and isopropoxy), and t-butoxy, etc.

"Aryl" refers to an aromatic carbocyclic group, including monocyclic or polycyclic aromatic hydrocarbon groups such as phenyl, naphthyl, anthryl, phenanthryl and the like.

"Aryloxy" refers to —O-aryl where the definition of aryl is as described above. The most preferred example of aryloxy is phenoxy.

"Halo" includes fluoro, chloro, bromo and iodo.

The compound of the present invention or a pharmaceutically acceptable salt thereof, is selected from:

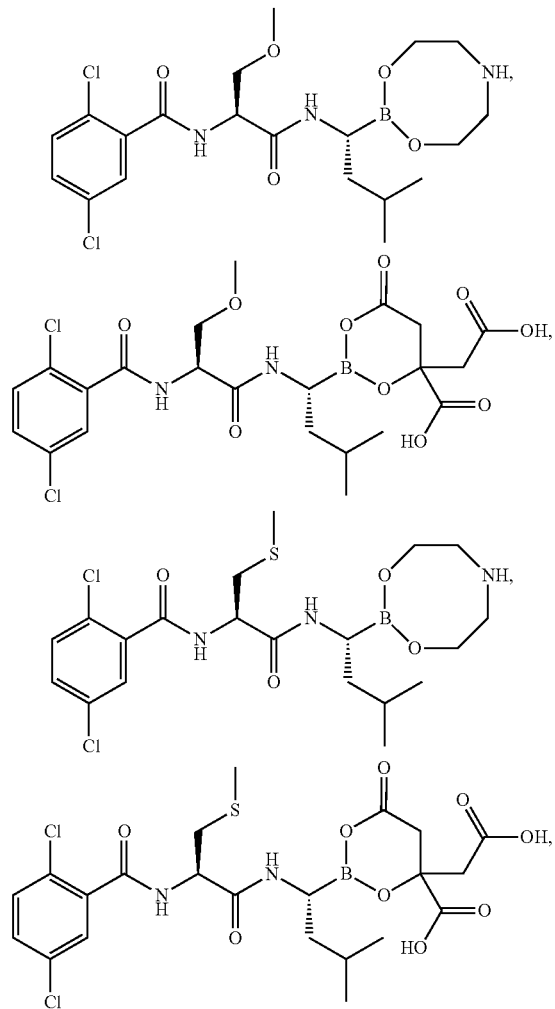

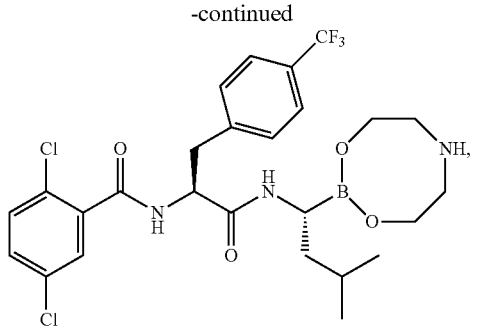

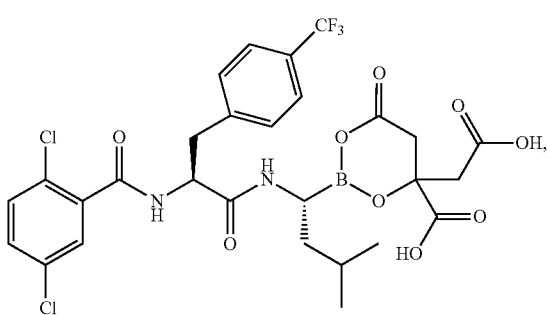

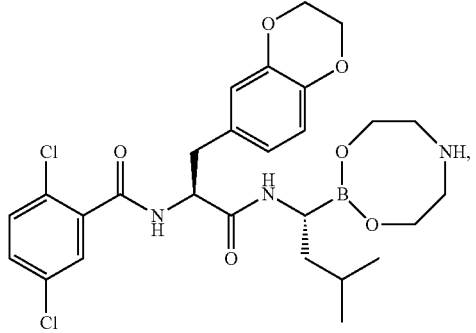

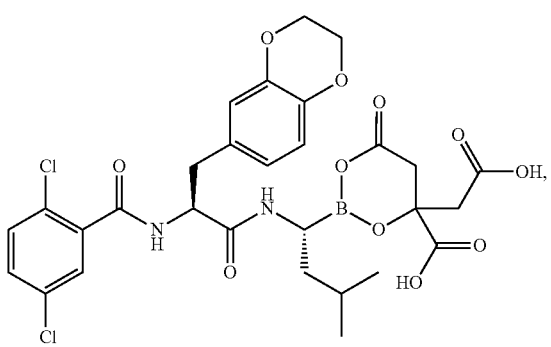

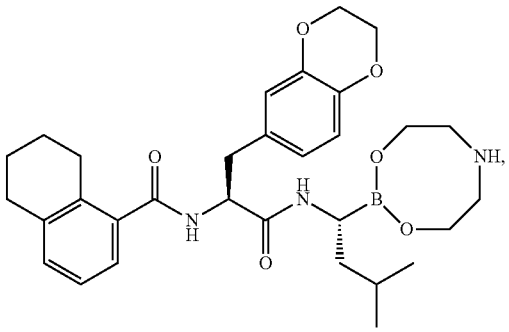

-continued
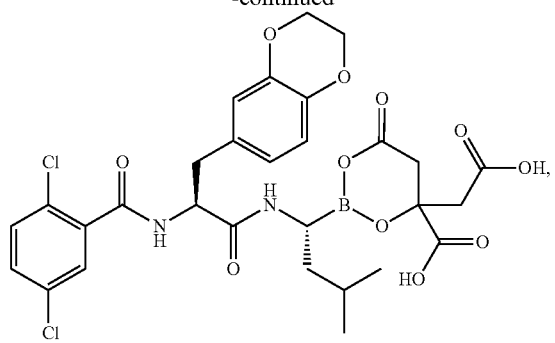
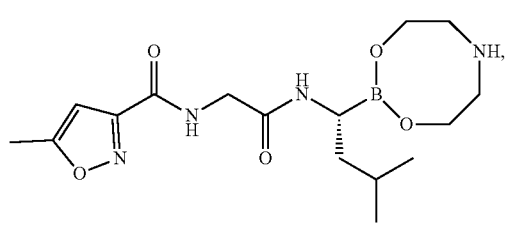
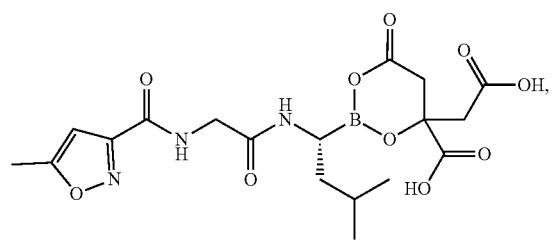
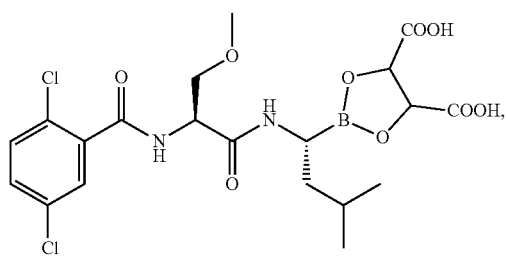
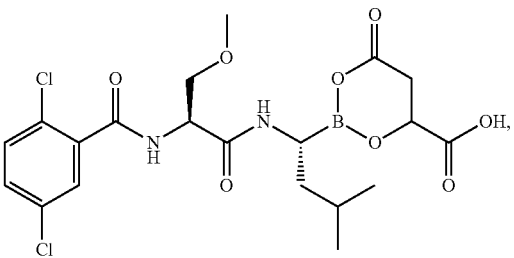
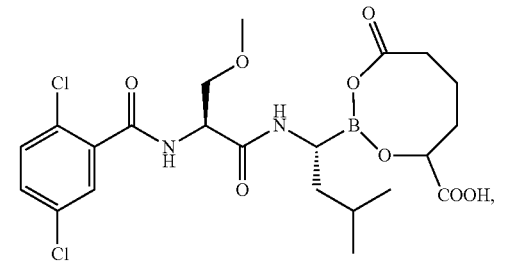
-continued
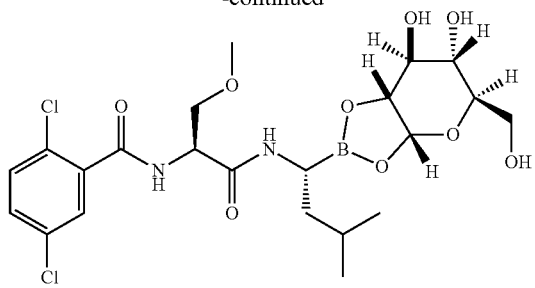
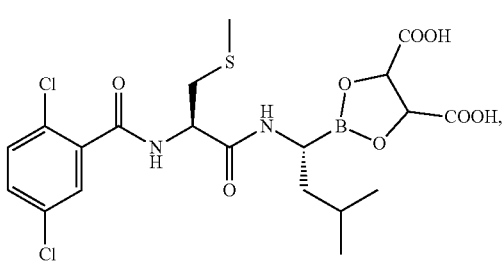
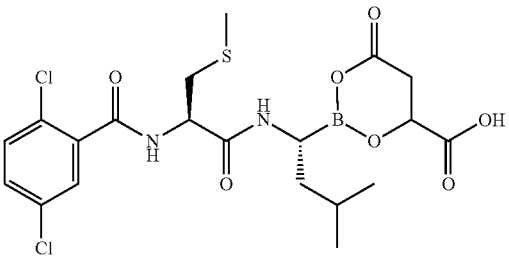
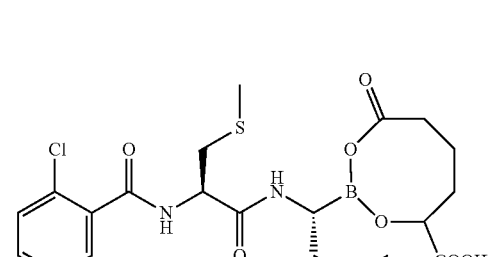
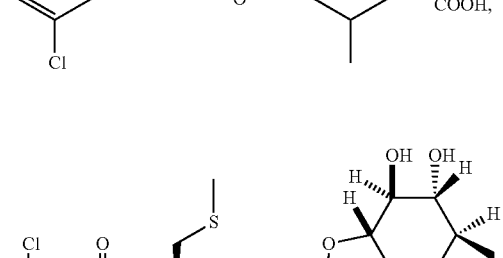
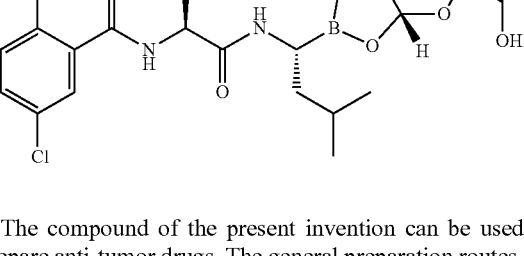
The compound of the present invention can be used to prepare anti-tumor drugs. The general preparation routes are as follows:

Route I
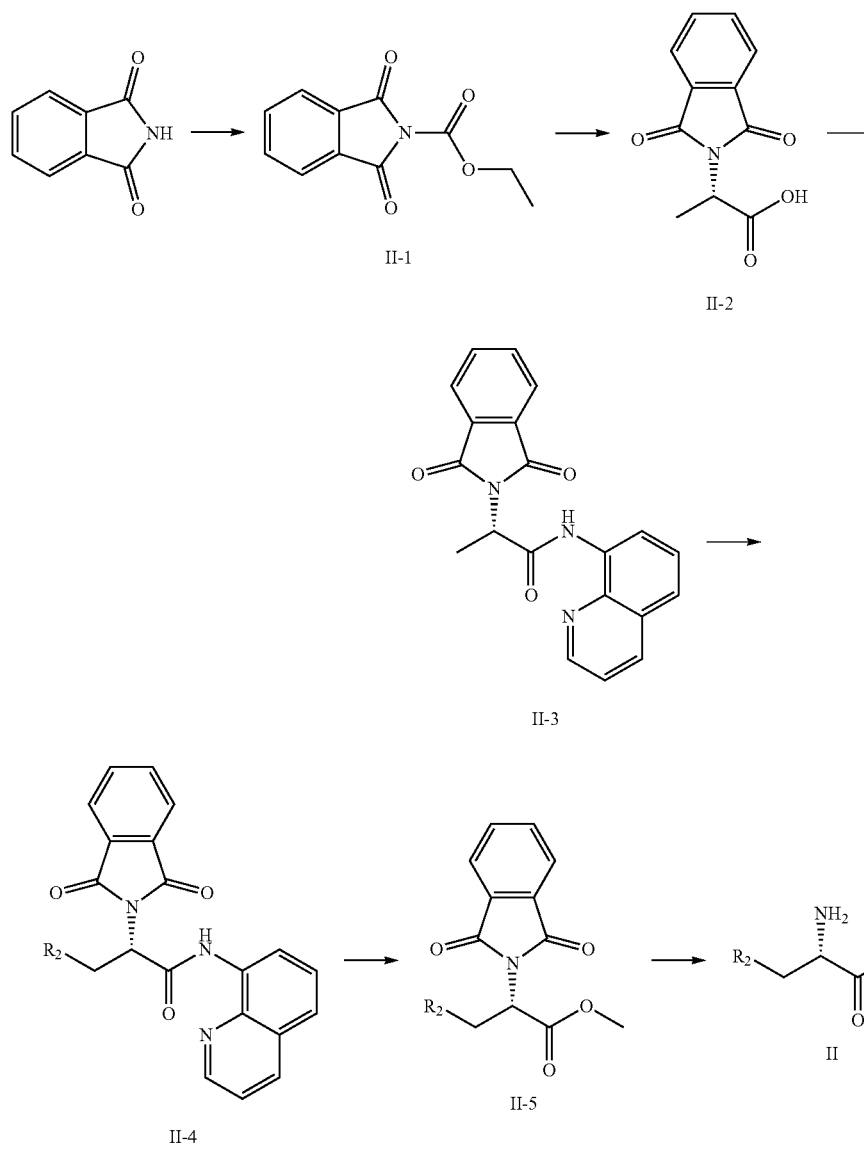
Route II
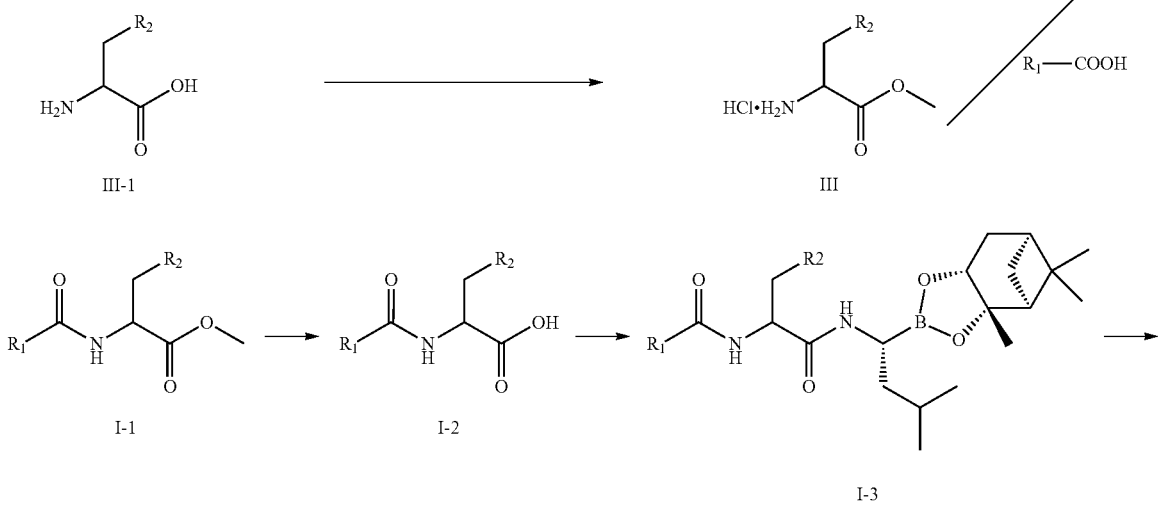

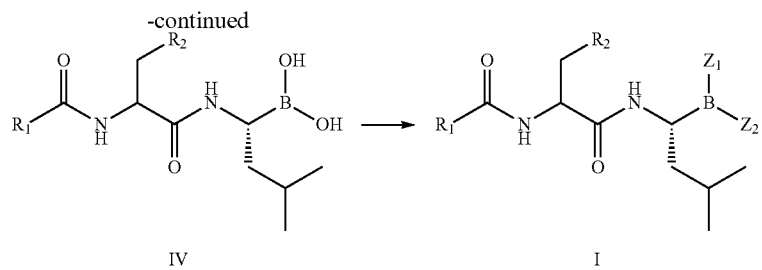

In the reaction formula, the groups $R_1$, $R_2$, $Z_1$ and $Z_2$ are as described above. Route I includes reacting phthalimide with ethyl chloroacetate to produce a compound of Formula (II-1), reacting the compound of Formula (II-1) with alanine to produce a compound of Formula (II-2), reacting the compound of Formula (II-2) with 8-aminoquinoline to produce a compound of Formula (II-3), reacting the compound of Formula (II-3) with an aryl iodide to produce a compound of Formula (II-4), reacting the compound of Formula (II-4) in the presence of boron trifluoride diethyl etherate to produce a compound of Formula (II-5), and reacting the compound of Formula (II-5) in the presence of ethylene diamine to produce a compound of Formula (II). Route II comprises reacting the compound of Formula (III-1) with methanol in the presence of $SOCl_2$ to produce a compound of Formula (III). The compound of Formula (II) in Route I or the compound of Formula (III) in route II is respectively reacted with $R_1$—COOH in the presence of a peptide condensing agent to produce a compound of Formula (I-1). The compound of Formula (I-1) is saponified and then acidified to produce a compound of Formula (I-2). The compound of Formula (I-2) is condensed with an amino hydrochloride or a trifluoroacetate of a borate ester in the presence of a peptide condensing agent to produce a compound of Formula (I-3). Then, the compound of Formula (I-3) reacts under an acidic condition to produce a compound of Formula (IV). Finally, the compound of Formula (IV) reacts in the presence of hot ethyl acetate to produce a compound of Formula (I).

In the reaction formula, the groups $R_1$, $R_2$, $Z_1$ and $Z_2$ are as described above.

The method for preparing the compound of the present invention is described in further detail below:

1. The method for preparing Compound II includes the following steps:

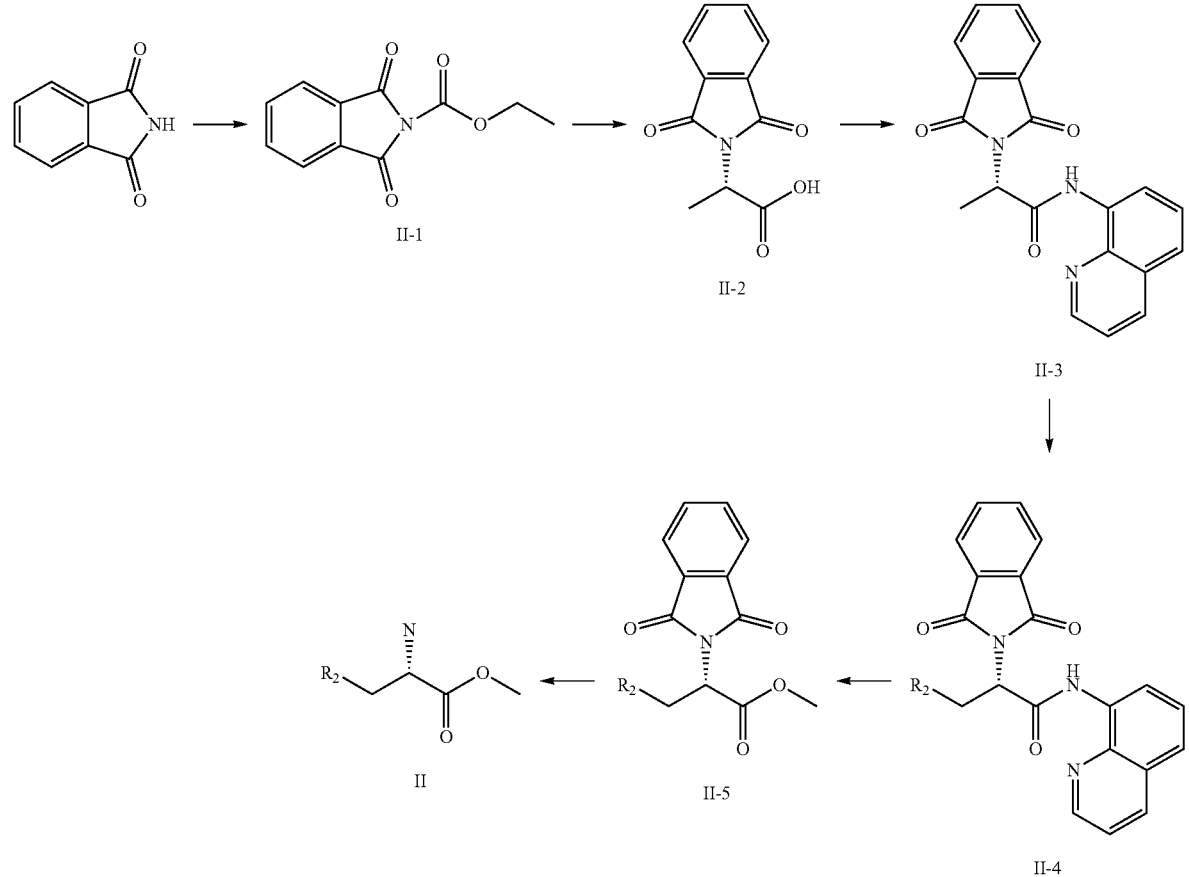

1) reacting phthalimide with ethyl chloroacetate in the presence of triethylamine to obtain a compound having a structure of Formula (II-1);

2) reacting the compound having a structure of Formula (II-1) with alanine in the presence of Na$_2$CO$_3$ and H$_2$O to produce a compound having a structure of Formula (II-2);

3) reacting the compound having a structure of Formula (II-2) in the presence of SOCl$_2$ to produce acyl chloride, and then reacting with 8-aminoquinoline under a basic condition to produce a compound of Formula (II-3);

4) reacting the compound having a structure of Formula (II-3) with an aryl iodide in the presence of palladium and silver tetrafluoroborate to produce a compound of Formula (II-4);

5) reacting the compound having a structure of Formula (II-4) with methanol in the presence of boron trifluoride etherate to produce a compound of Formula (II-5); and 6) reacting the compound having a structure of Formula (II-5) with methanol in the presence of ethylene diamine to produce a compound of Formula (II).

2. The method for preparing Compound (III) includes the following steps:

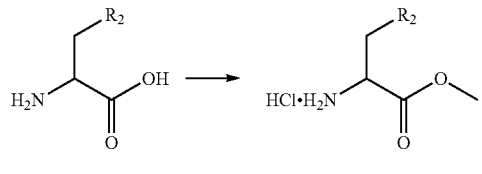

reacting an amino acid having a structure of Formula (III-1) with methanol in the presence of SOCl$_2$ to produce a compound of Formula (III).

3. The method for preparing (I) includes the following steps:

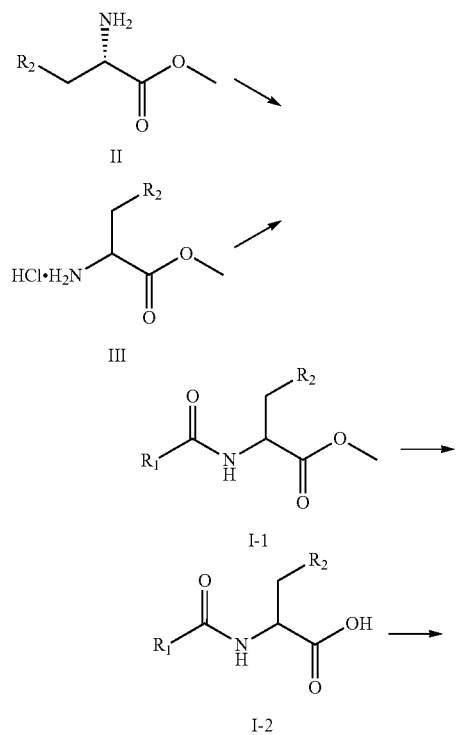

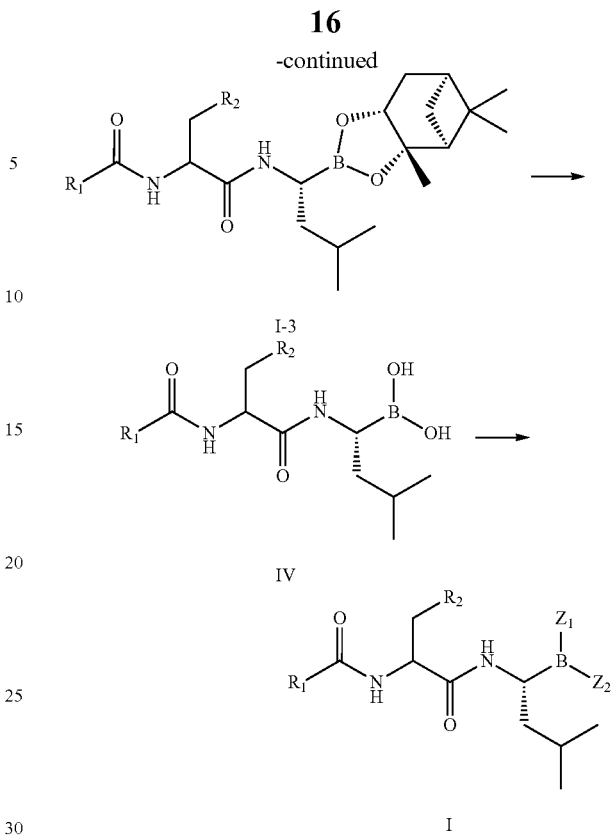

1) reacting the compound of Formula (II) or Formula (III) with R$_1$—COOH in the presence of a peptide condensing agent to produce a compound of Formula (I-1);

2) saponifying the compound having a structure of Formula (I-1) to produce a sodium salt thereof, and then reacting under an acidic condition to produce a compound of Formula (I-2);

3) condensing the compound of Formula (I-2) with an amino hydrochloride or a trifluoroacetate of a borate ester in the presence of a peptide condensing agent to produce a compound of Formula (I-3);

4) reacting the compound of Formula (I-3) in the presence of isobutylboric acid to produce a compound of Formula (IV); and 5) reacting the compound of Formula (IV) in the presence of boiling ethyl acetate to produce a compound of Formula (I).

The common peptide condensing agent in the above reactions is N,N-dicyclohexyl-carbodiimide (DCC), 1-(3-dimethylaminopropyl)-3-ethylcarbodiimide hydrochloride (EDC.HCl), 1-hydroxybenzotriazole (HOBt) or isobutyl chloroformate.

In the reaction formula, the groups R$_1$, R$_2$, Z$_1$ and Z$_2$ are as described above.

Experiments have confirmed that the compound of the present invention has good proteasome inhibitory activity and anti-tumor activity, and some compounds exhibit good proteasome inhibitory activity and anti-tumor effect at the nanomolar level, and are of application value in preparing proteasome inhibitors or anti-tumor drugs. The peptide borate ester compound of the present invention has better pharmacokinetic behaviors than peptide boric acid compounds.

Moreover, the preparation method of the compound designed in the present invention has high yield and simple process, and is suitable for industrial production.

DETAILED DESCRIPTION

Section I. Synthesis of Compounds

Figure 1:
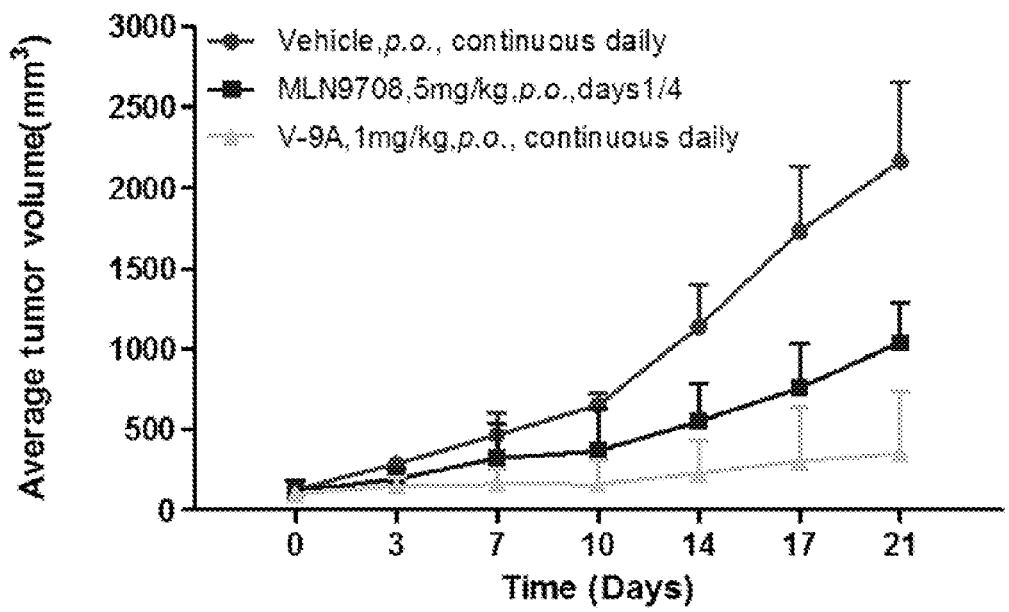
FIG. 1 shows the growth trend of ARH-77 xenograft tumors after administration of various compounds.

The preparation of the compound of the present invention can be implemented according to the following process:

I. Production of Compound (II)

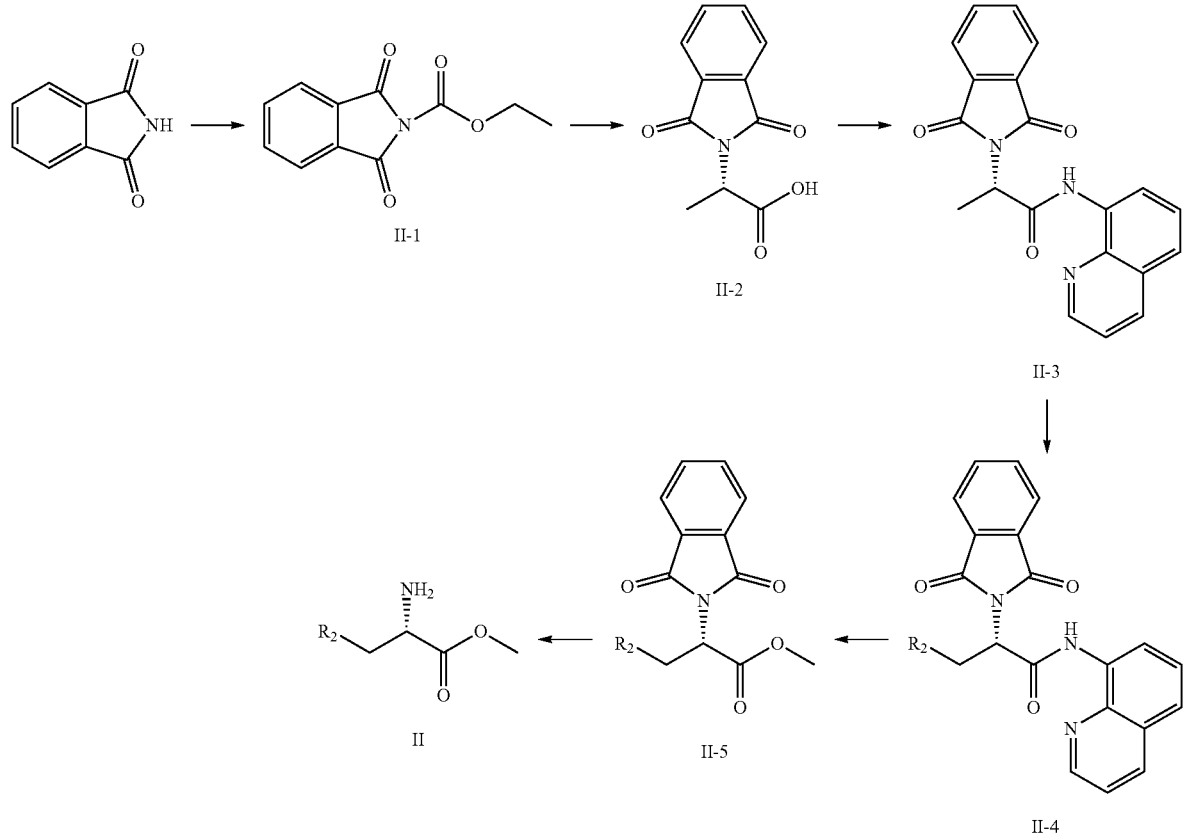

1. Production of N-Ethyl Acetate Phthalimide II-1

Phthalimide is dissolved in DMF, triethylamine is added, and then ethyl chloroacetate is added dropwise to the reaction system at 0° C., slowly heated to room temperature and reacted for 2 hrs. The reaction solution is poured into ice water, and filtered. The filter cake is washed with ice water, and dried under vacuum to obtain a pure compound (Formula II-1).

2. Production of N-phthaloyl Protected Alanine II-2

Compound II-1 and L-alanine are dissolved in $H_2O$, and then $Na_2CO_3$ is added and reacted for 2 hrs. The reaction solution is adjusted to pH 2 with 1N HCl, filtered, and dried under vacuum to obtain a pure compound (Formula II-2).

3. Production of Compound II-3

Compound II-2 is dissolved in $CH_2Cl_2$, and then $SOCl_2$ is added, condensed and refluxed for 6 hrs. The solvent is removed by evaporation under reduced pressure. 8-aminoquinoline and DIPEA are dissolved in $CH_2Cl_2$, and acyl chloride dissolved in $CH_2Cl_2$ is added dropwise at −20° C., slowly heated to room temperature and reacted overnight. The solvent is removed by evaporation under reduced pressure, and the residue is separated by column chromatography to obtain Compound II-3.

4. Production of Compound II-4

Compound II-3 is dissolved in tert-butanol, and then palladium acetate, silver tetrafluoroborate and an alkyl iodide are added, condensed and refluxed for 24 hrs. The reaction solution is warmed to room temperature, and diluted with $CHCl_2$. Triethylamine is added and reacted for 3 hrs. The reaction solution is passed through diatomaceous earth, the solvent is removed by evaporated under reduced pressure, and the residue is separated by column chromatography to obtain Compound II-4.

5. Production of Compound II-5

Compound II-4 is dissolved in MeOH in a thick-walled pressure flask, a boron trifluoride etherate solution is added dropwise, and reacted overnight at 100° C. Triethylamine is added and stirred, and the solvent is removed by evaporation under reduced pressure. The residue is dissolved in CH$_2$Cl$_2$, then washed respectively with an acid (10% hydrochloric acid), an alkaline (5% sodium bicarbonate) and saturated brine, and dried over a desiccant (anhydrous sodium sulfate and anhydrous magnesium sulfate). The desiccant is filtered off, the solvent is evaporated off under reduced pressure, and the residue is separate by column chromatography to obtain Compound II-5.

6. Production of Compound II

Compound II-5 is dissolved in MeOH, and then ethylene diamine is added, and reacted for 5 hrs under condensation and reflux at 70° C. After filtering, the solvent is removed from the filtrate by evaporation under reduced pressure, and the residue is separate by column chromatography to obtain Compound II.

II. Production of Compound (III)

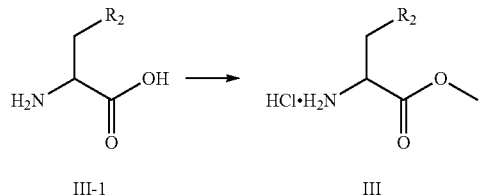

III-1    III

Compound III-1 is dissolved in MeOH, and then SOCl$_2$ is added dropwise in an ice-salt bath and then warmed to room temperature overnight. After the solvent is removed by evaporation under reduced pressure, Compound III is obtained.

III. Production of Compound (I)

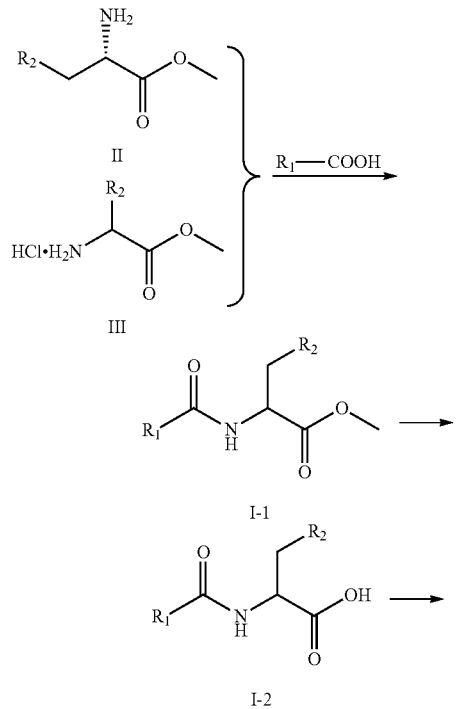

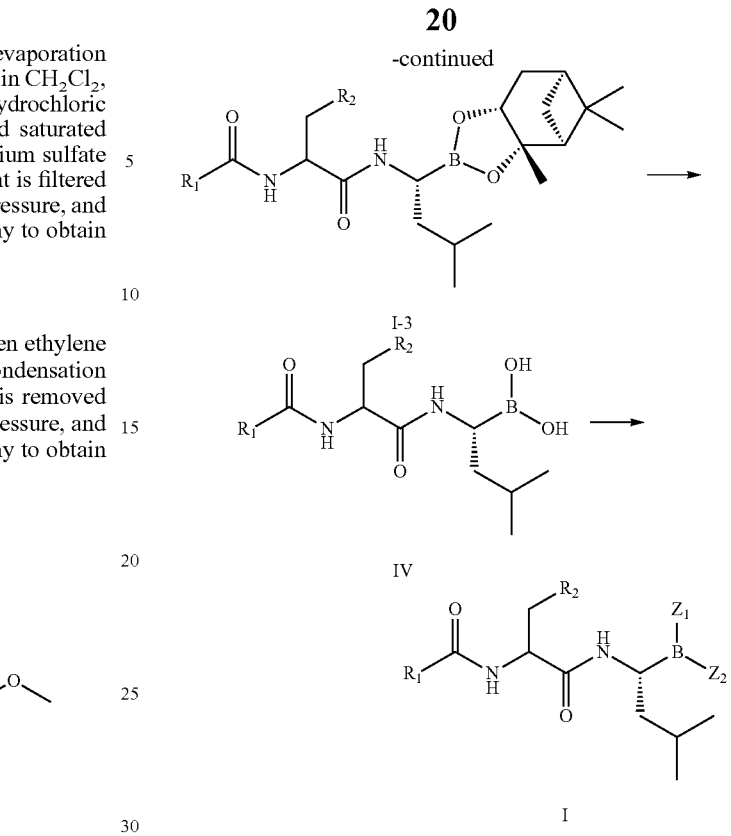

1. Production of Compound I-1

R$_1$—COOH is dissolved in CH$_2$Cl$_2$, and then 1-hydroxybenzotriazole (HOBt) is added, and reacted for 10 min at −5° C. Then, a peptide condensing agent (EDC.HCl) is added, and reacted for 20 min. Compound II or III is added, and then N,N-diisopropylethylamine (DIPEA) is added after 10 min, reacted for half an hour, and then stirred overnight at room temperature. The reaction solution is washed respectively with an acid (10% hydrochloric acid), an alkaline (5% sodium bicarbonate) and saturated brine, and dried over a desiccant (anhydrous sodium sulfate and anhydrous magnesium sulfate). The desiccant is filtered off, the solvent is evaporated off under reduced pressure, and the residue is separate by column chromatography to obtain Compound I-1.

2. Production of Compound I-2

Compound I-1 is dissolved in MeOH, and then LiOH.H$_2$O and H$_2$O are added, and reacted for 3 hrs. MeOH is removed by evaporation under reduced pressure. The remaining solution is adjusted to pH 2 with 1N HCl, extracted with ethyl acetate, and separated. After the solvent is removed by evaporation under reduced pressure, Compound I-2 is obtained.

3. Production of Compound I-3

Compound I-2 is dissolved in CH$_2$Cl$_2$, and then 1-hydroxybenzotriazole (HOBt) is added, and reacted for 10 min at −5° C. A peptide condensing agent (EDC.HCl) is added, and reacted for 20 min. An amino hydrochloride or a trifluoroacetate of a borate ester is added, and then N,N-diisopropylethylamine (DIPEA) is added after 10 min, reacted for half an hour, and then stirred overnight at room temperature. The reaction solution is washed respectively with an acid (10% hydrochloric acid), an alkaline (5% sodium bicarbonate) and saturated brine, and dried over a desiccant (anhydrous sodium sulfate and anhydrous magnesium sulfate). The desiccant is filtered off, the solvent is evaporated off under reduced pressure, and the residue is separate by column chromatography to obtain Compound I-3.

4. Production of Compound IV

Compound I-3 is dissolved in MeOH, and then isobutylboric acid, n-hexane and 1N HCl are added and reacted overnight. After separation, the n-hexane phase is extracted twice with MeOH, and then the methanol phase is washed once with n-hexane. Methanol is removed by evaporation under reduced pressure, and the aqueous phase is extracted twice with CH$_2$Cl$_2$. The organic phase is washed with saturated brine until the aqueous phase is neutral. The solvent is removed by evaporation under reduced pressure, and the residue is separated by column chromatography to obtain Compound IV.

5. Production of Compound I

An amine or acid containing a diol is dissolved in ethyl acetate at 74° C., and Compound IV is added, cooled to 60° C., reacted for 3 hrs, then cooled to 25° C. and reacted overnight. After filtering and drying under vacuum, a pure compound (Formula I) is obtained.

Hereinafter, the preparation process of the compound of the present invention is described by means of the synthesis of specific compounds:

I. Production of Compounds of Formula (II)

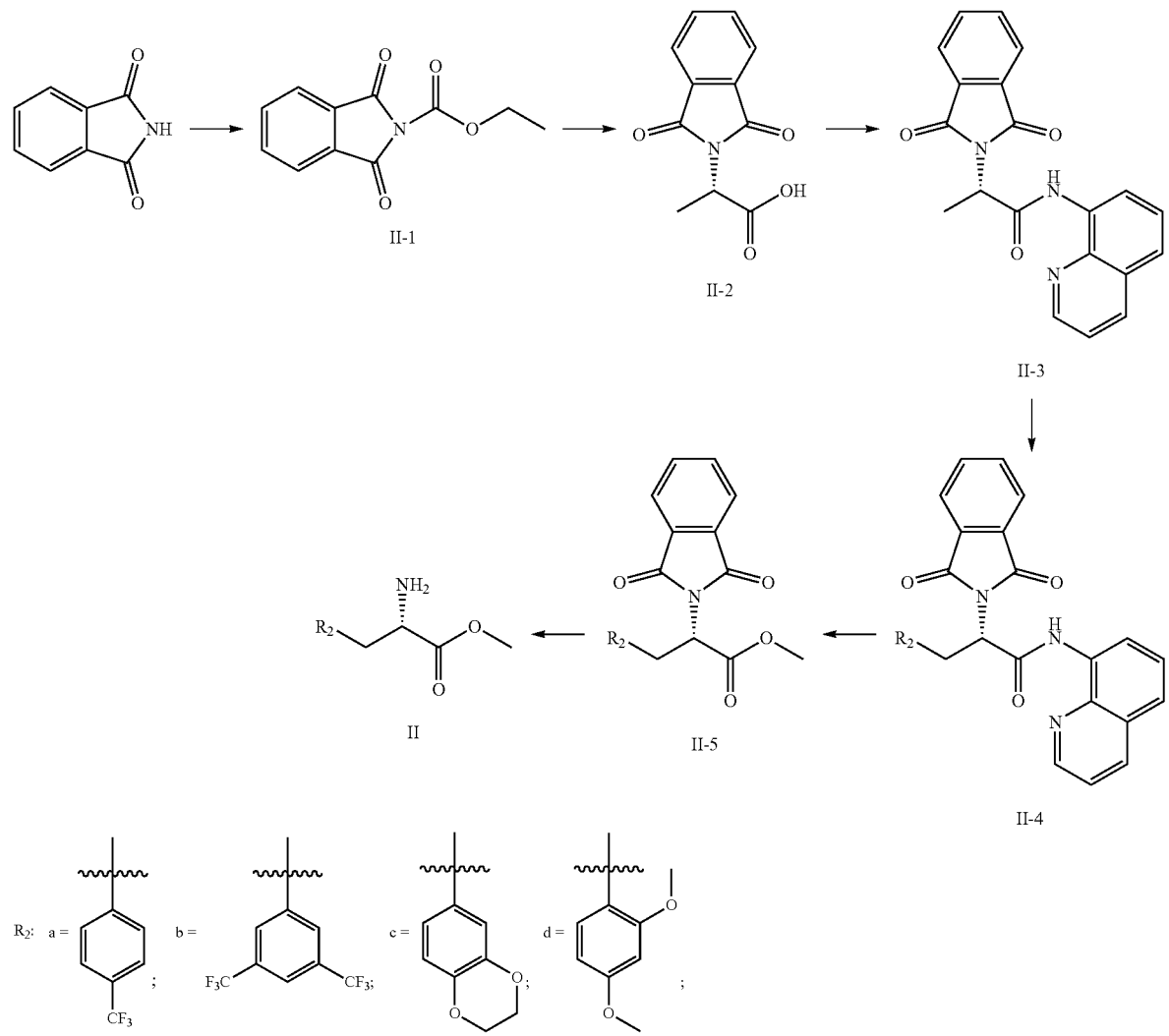

1. Production of N-ethyl Acetate Phthalimide (Compound II-1)

Phthalimide (7.36 g, 50 mmol) was dissolved in DMF (25 mL), triethylamine (9 mL, 65 mmol) was added, and then ethyl chloroacetate (5.7 mL, 60 mmol) was added dropwise to the reaction system at 0° C., slowly heated to room temperature and reacted for 2 hrs until the reaction was completed as indicated by TLC. The reaction solution was poured into ice water, and filtered. The filter cake was washed with ice water, and dried under vacuum to obtain pure N-ethyl acetate phthalimide (8.67 g, yield 79.1%. mp 81.4-83.6° C.). $^1$H NMR (400 MHz, CDCl$_3$) δ 1.44 (—CH$_3$, Hz, 3H), 4.48 (—CH$_2$, q, 7.1 Hz, 2H), 7.80-7.85 (-Ph, m, 2H), 7.93-7.99 (-Ph, m, 2H). MS (ESI): m/z 220.1 [M+H]$^+$.

2. Production of N-phthaloyl Protected Alanine (Compound II-2)

Compound II-1 (21.9 g, 100 mmol) and L-alanine (8.9 g, 10 mmol) were dissolved in H$_2$O (100 mL), and then Na$_2$CO$_3$ (10.6 g, 100 mmol) was added and reacted for 2 hrs until the reaction was completed as indicated by TLC. The reaction solution was adjusted to pH 2 with 1N HCl, filtered, and dried under vacuum to obtain a pure compound (Formula II-2) (17.4 g, yield 79.3%, mp 145.8-146.6° C.). $^1$H NMR (400 MHz, CDCl$_3$) δ 1.71 (—CH$_3$, d, 7.4 Hz, 3H), 5.02 (—CH, q, J=7.4 Hz, 1H), 7.69-7.75 (-Ph, m, 2H), 7.82-7.88 (-Ph, m, 2H). MS (ESI): m/z218.2 [M−H]$^-$.

3. Production of (S)-2-(phthalimido)-N-(8-quinolinyl)propionamide (Compound II-3)

Compound II-2 (17.37 g, 79.25 mmol) was dissolved in CH$_2$Cl$_2$ (80 mL), and then SOCl$_2$ (29 mL, 396.25 mmol) was added, condensed and refluxed for 6 hrs. The solvent was removed by evaporation under reduced pressure. 8-Aminoquinoline (11.4 g, 79.25 mmol) and DIPEA (20.5 g, 158.5 mmol) were dissolved in CH$_2$Cl$_2$ (103 mL), and acyl chloride (31 mL) dissolved in CH$_2$Cl$_2$ was added dropwise at −20° C., then slowly heated to room temperature and reacted overnight until the reaction was completed as indicated by TLC. The solvent was removed by evaporation under reduced pressure, and the residue was separated by column chromatography to obtain Compound II-3 (21.2 g, yield 77.42%. mp 180.0-181.9° C.). H NMR (400 MHz, CDCl$_3$) δ 1.98 (—CH$_3$, d, 7.3 Hz, 3H), 5.27 (—CH, q, J=7.5 Hz, 1H), 7.42 (-Ph, dd, J$_1$=4.2 Hz, J$_2$=8.3 Hz, 1H), 7.51 (-Ph, s, 1H), 7.53 (-Py, d, J=9.0 Hz, 1H), 7.65-7.85 (-Ph, m, 2H), 7.90 (-Ph, dt, J$_1$=3.6 Hz, J$_2$=7.1 Hz, 2H), 8.15 (-Py, d, J=8.3 Hz, 1H), 8.69 (-Ph, d, 4.2 Hz, 1H), 8.73 (-Py, dd. J$_1$=4.7 Hz, J$_2$=8.9 Hz, 1H), 10.33 (—CONH, s, 1H). MS(ESI): m/z346.0 [M+H]$^+$.

4. Production of (S)-methyl 2-amino-3-(4-(trifluoromethyl) phenyl)propionate (II-4a)

(1) Production of (S)-2-(phthalimido)-N-(8-quinolinyl)-3-(4-(trifluoromethyl) phenyl)propionamide (II-4a)

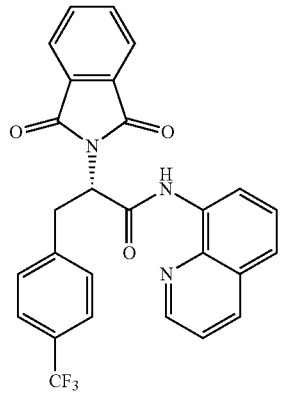 [SMILES: O=C(Nc1cccc2cccnc12)[C@H](Cc1ccc(C(F)(F)F)cc1)N1C(=O)c2ccccc2C1=O]

Compound II-3 (5.2 g, 15 mol) was dissolved in tert-butanol (105 mL), and then palladium acetate (331 mg, 1.5 mmol), silver tetrafluoroborate (3.65 g, 18.75 mmol) and 4-iodobenzotrifluoride (6.12 g, 22.5 mmol) were added, condensed and refluxed for 24 his at 85° C., until the reaction was completed as indicated by TLC. The reaction solution was warmed to room temperature, and diluted with CH$_2$Cl$_2$ (100 mL). Triethylamine (10 mL) was added and stirred for 3 hrs. The reaction solution was passed through diatomaceous earth, the solvent was removed by evaporated under reduced pressure, and the residue was separated by column chromatography to obtain a solid product (5.3 g, yield 72.1%, mp 124.0-125.5° C.). $^1$H NMR (400 MHz, CDCl$_3$) δ 3.77-3.95 (—CH$_2$, m, 2H), 5.47 (—CH, dd, J$_1$=6.9 Hz, J$_2$=9.7 Hz, 1H), 7.39 (-Ph, dd, J$_1$=4.3 Hz, J$_1$=8.3 Hz, 1H), 7.42 (-Ph, d, 8.1 Hz, 2H), 7.49 (-Ph, d, J=8.2 Hz, 2H), 7.51 (-Ph, s, 1H), 7.53 (-Py, t, J=5.5 Hz, 1H), 7.68-7.78 (-Ph, m, 2H), 7.78-7.91 (-Ph, m, 2H), 8.12 (-Py, dt, J$_1$=7.1 Hz, J$_2$=14.1 Hz, 1H), 8.58 (-Ph, dd, J$_1$=1.5 Hz, J$_2$=4.2 Hz, 1H), 8.67-8.79 (-Py, m, 1H), 10.28 (—CONH, s, 1H). MS (ESI): m/z487.1 [M−H]$^-$.

Other similar compounds can be prepared through the above steps.

II-4b was synthesized with II-3 and 1-iodo-3,5-bis(trifluoromethyl)benzene following the method of Example (1); II-4c was synthesized with II-3 and 6-iodo-1,4-benzodioxine following the method of Example (1); and II-4d was synthesized with II-3 and 2,4-dimethoxyiodobenzene following the method of Example (1).

The specific compound synthesized and their properties are shown in a table below.

| No. | Structure | Chemical name and analytical data |
|---|---|---|
| II-4b | 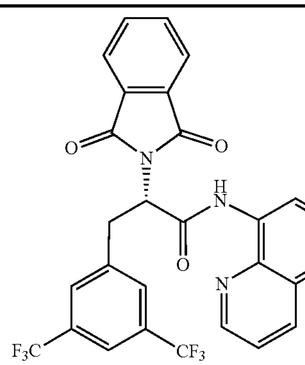 | (S)-3-(3,5-bis(trifluoromethyl) phenyl)-2-(phthalimido)-N-(8-quinolinyl)propionamide Yield 74.0%, mp: 121.1-123.8° C. $^1$H NMR (400 MHz, CDCl$_3$) δ 3.87 (—CH$_2$, dd, J$_1$ = 10.7 Hz, J$_2$ = 14.0 Hz, 1H), 3.96 (—CH$_2$, dd, J$_1$ = 5.9 Hz, J$_2$ = 14.3 Hz, 1H), 5.41 (—CH, dd, J$_1$ = 6.0 Hz, J$_2$ = 10.4 Hz, 1H), 7.39 (—Ph, dd, J$_1$ = 4.2 Hz, J$_2$ = 8,2 Hz, 1H), 7.47-7.59 (—Ph, m, 2H), 7.69 (—Py, s, 1H), 7.73 (—Ph, s, 2H), 7,76 (—Ph, dd, J$_1$ = 3.2 Hz, J$_2$ = 5.3 Hz, 2H), 7.86 (—Ph, dd, J$_1$ = 3.1 Hz, J$_2$ = 5.1 Hz, 2H), 8.13 (—Py, d, J = 8.2 Hz, 1H), 8.57 (—Ph, d, J = 3.8 Hz, 1H), 8.72 (—Py, dd, J$_1$ = 2.7 Hz, J$_2$ = 5.8 Hz, 1H), 10.27 (—CONH, s, 1H). MS (ESI) m/z 558.2 [M + H]$^+$. |

| No. | Structure | Chemical name and analytical data |
|---|---|---|
| II-4c | 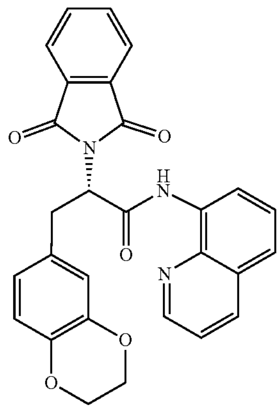 [SMILES: O=C(Nc1cccc2cccnc12)[C@H](Cc1ccc2c(c1)OCCO2)N1C(=O)c2ccccc2C1=O] | (S)-3-(3,4-benzodioxinyl)-2-(phthalimido)-N-(8-quinolinyl)propionamide<br>Yield 66.7%, mp 178.3-179.9° C. $^1$H NMR (400 MHz, CDCl$_3$) δ 3.54-3.81 (—CH$_2$, m, 2H), 4.06-4.26 (—CH$_2$, m, 4H), 5.38 (—CH, dd, J$_1$ = 6.6 Hz, J$_2$ = 9.9 Hz, 1H), 6.74 (—Ph, dt, J$_1$ = 5.0 Hz, J$_2$ = 16.7 Hz, 2H), 6.83 (—Ph, d, J = 1.7 Hz, 1H), 7.40 (—Py, dd, J$_1$ = 4.2 Hz, J$_2$ = 8.3 Hz, 1H), 7.45-7.56 (—Ph, m, 2H), 7.65-7.79 (—Ph, m, 2H), 7.80-7.90 (—Ph, m, 2H), 8.12 (—Py, dd, J$_1$ = 1.5 Hz, J$_2$ = 8.3 Hz, 1H), 8.63 (—Ph, dd, J$_1$ = 1.5 Hz, J$_2$ = 4.2 Hz, 1H), 8.68-8.78 (—Py, m, 1H), 10.29 (—CONH, s, 1H). MS (ESI) m/z 477.9 [M − H]$^-$. |
| II-4d | 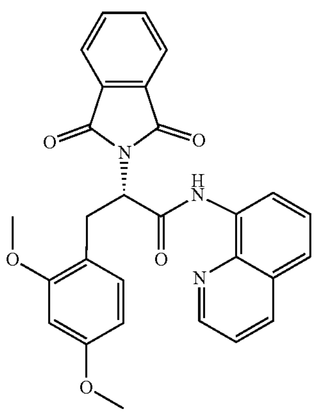 [SMILES: COc1ccc(C[C@@H](C(=O)Nc2cccc3cccnc23)N2C(=O)c3ccccc3C2=O)c(OC)c1] | (S)-3-(2,4-dimethoxyphenyl)-2-(phthalimido)-N-(8-quinolinyl)propionamide<br>Yield 75.46%. mp 89.2-90.3° C. $^1$H NMR (400 MHz, CDCl$_3$) δ 3.69 (—CH$_2$, dd, J$_1$ = 10.4 Hz, J$_2$ = 13.8 Hz, 1H), 3.74 (—CH$_3$, s, 3H), 3.79 (—CH$_2$, dd, J$_1$ = 5.1 Hz, J$_2$ = 13.8 Hz, 1H), 3.86 (—CH$_3$, s, 3H), 5.57 (—Ph, dd, J$_1$ = 5.1 Hz, J$_2$ = 10.3 Hz, 1H), 6.28 (—Ph, dd, J$_1$ = 2.3 Hz, J$_2$ = 8.2 Hz, 1H), 6.44 (—Ph, d, J = 2.1 Hz, 1H), 7.03 (—Ph, d, 8.2 Hz, 1H), 7.43 (—Py, dd, J$_1$ = 4.2 Hz, J$_2$ = 8.3 Hz, 1H), 7.49-7.58 (—Ph, m, 2H), 7.72 (—Ph, dd, J$_1$ = 3.1 Hz, J$_2$ = 5.4 Hz, 2H), 7.84 (—Ph, dt, J$_1$ = :3.5 Hz, J$_2$ = 7.1 Hz, 2H), 8.16 (—Py, d, 8.2 Hz, 1H), 8.70 (—Ph, d, J = 4.2 Hz, 1H), 8.78 (—Py, dd, J$_1$ = 2.3 Hz, J$_2$ = 6.5 Hz, 1H), 10.37 (—CONH, s, 1H). MS (ESI) m/z 480.0 [M − H]$^-$. |

(2) Production of (S)-methyl 2-(phthalimido)-3-(4-(trifluoromethyl) phenyl)propionate (II-5a)

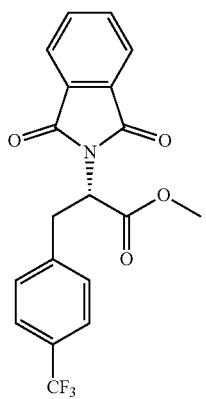 [SMILES: COC(=O)[C@H](Cc1ccc(C(F)(F)F)cc1)N1C(=O)c2ccccc2C1=O]

Compound II-5a (2 g, 4.1 mmol) was dissolved in MeOH (94 mL) in a thick-walled pressure flask, a boron trifluoride etherate solution (5.2 mL, 40.9 mmol) was slowly added dropwise, and reacted overnight at 100° C. until the reaction was completed as indicated by TLC. Triethylamine (8.6 mL, 61.3 mmol) was added and stirred for a period of time. The solvent was removed by evaporation under reduced pressure. The residue was dissolved in CH$_2$Cl$_2$ (30 mL), then washed respectively with an acid (10% hydrochloric acid), an alkaline (5% sodium bicarbonate) and saturated brine, and dried over a desiccant (anhydrous sodium sulfate and anhydrous magnesium sulfate). The desiccant is filtered off, the solvent is evaporated off under reduced pressure, and the residue is separate by column chromatography to obtain a product as an oil (1.3 g, yield 83.2%). $^1$H NMR (400 MHz, CDCl$_3$) δ 3.55-3.71 (—CH$_2$, m, 2H), 3.78 (—CH$_3$, s, 3H), 5.18 (—CH, dd, J$_1$=5.8 Hz, J$_2$=10.7 Hz, 1H), 7.30 (-Ph, d, J=8.0 Hz, 2H), 7.46 (-Ph, d, J=8.0 Hz, 2H), 7.67-7.75 (-Ph, m, 2H), 7.79 (-Ph, dt, J$_1$=3.6 Hz, J$_2$=7.1 Hz, 2H). MS (ESI): m/z 378.3 [M+H]$^+$.

Other similar compounds can be prepared through the above steps.

II-5b was synthesized with II-4b following the method of Example (2); II-5c was synthesized with II-4c following the method of Example (2); and II-5d was synthesized with II-4d following the method of Example (2).

The specific compound synthesized and their properties are shown in a table below.

| No. | Structure | Chemical name and analytical data |
|---|---|---|
| II-5b | 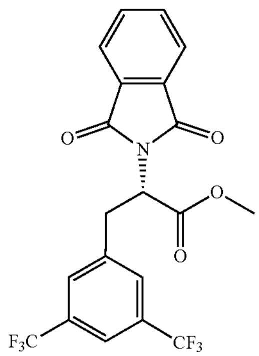 [SMILES: COC(=O)[C@H](Cc1cc(C(F)(F)F)cc(C(F)(F)F)c1)N1C(=O)c2ccccc2C1=O] | (S)-methyl 3-(3,5-bis(triflitioromethyl) phenyl)-2-(phthalimido)propionate<br>Yield 79.8%, $^1$H NMR (400 MHz, CDCl$_3$) δ 3.57-3.68 (—CH$_2$, m, 1H), 3,73 (—CH$_2$, dd, J$_1$ = 5.4 Hz, J$_2$ = 14.5 Hz, 1H), 3.79 (—CH$_3$, s, 3H), 5.14 (—CH, dd, J$_1$ = 5.4 Hz, J$_2$ = 10.6 Hz, 1H), 7.63 (—Ph, s, 2H), 7.67 (—Ph, s, 1H), 7.70-7.77 (—Ph, m, 2H), 7.81 (—Ph, d, J = 3.2 Hz, 2H). MS (ESI): m/z 446.1 [M + H]$^+$. |
| II-5c | 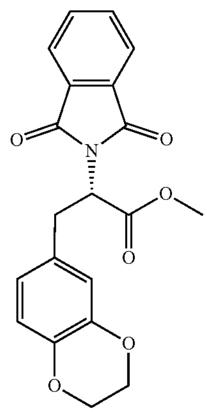 [SMILES: COC(=O)[C@H](Cc1ccc2c(c1)OCCO2)N1C(=O)c2ccccc2C1=O] | (S)-methyl 3-(3,4-benzodioxinyl)-2-(phthalimido)propionate<br>Yield 65.3%. $^1$H NMR (400 MHz, CDCl$_3$) δ 3.35-3.55 (—CH$_2$, m, 2H), 3.77 (—CH$_3$, s, 3H), 4.17 (—CH$_2$, d, J = 7.0 Hz, 4H), 5.04 (—CH, dd, J$_1$ = 5.4 Hz, J$_2$ = 11.0 Hz, 1H), 6.60 (—Ph, d, J = 8.2 Hz, 1H), 6.66 (—Ph, d, J = 8.5 Hz, 1H), 6.68 (—Ph, s, 1H), 7,71 (—Ph, d, J = 3.6 Hz, 2H), 7.80 (—Ph, d, J = 3.4 Hz, 2H). MS (ESI): m/z 368.4 [M + H]$^+$. |
| II-5d | 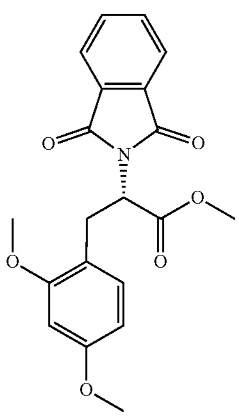 [SMILES: COC(=O)[C@H](Cc1ccc(OC)cc1OC)N1C(=O)c2ccccc2C1=O] | (S)-methyl 3-(2,4-dimethoxy phenyl)-2-(phthalimido)propionate<br>Yield 75.2%. $^1$H NMR (400 MHz, CDCl$_3$) δ 3.36 (—CH$_2$, dd, J$_1$ = 11.4 Hz, J$_2$ = 13.9 Hz, 1H), 3.55 (—CH$_2$, dt, J$_1$ = 6.3 :Hz, J$_2$ = 12.5 Hz, 1H), 3.69 (—CH$_3$, s, 3H), 3.72 (—CH$_3$, s, 3H), 3.77 (—CH$_3$, s, 3H), 5,30-5.37 (—CH, m, 1H), 6.22 (—Ph, dd, J$_1$ = 2.4 Hz, J$_2$ = 8.2 Hz, 1H), 6.33 (—Ph, d, J = 2.3 Hz, 1H), 6.89 (—Ph, d, J = 8.2 Hz, 1H), 7.65-7.71 (—Ph, m, 2H), 7.74-7.80 (—Ph, m, 2H). MS (ESI): m/z 370.4 [M + H]$^+$. |

(3) Production of (S)-methyl 2-amino-3-(4-(trifluoromethyl) phenyl)propionate (IIa)

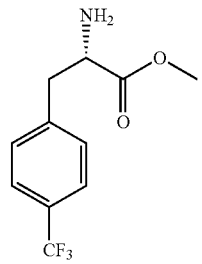 [SMILES: COC(=O)[C@@H](N)Cc1ccc(C(F)(F)F)cc1]

Compound II-5a (745 mg, 1.9 mmol) was dissolved in MeOH (19 mL), and then ethylene diamine (297 mg, 4.9 mmol) was added, and reacted for 5 hrs under condensation and reflux at 70° C., until the reaction was completed as indicated by TLC. After filtering, the solvent was removed from the filtrate by evaporation under reduced pressure, and the residue was separate by column chromatography to obtain the target compound as an oil (311 mg, yield 62.4%).
$^1$H NMR (400 MHz, DMSO) δ 2.84 (—CH$_2$, dd, J$_1$=7.7 Hz, J$_2$=13.3 Hz, 1H), 2.95 (—CH$_2$, dt, J$_1$=9.5 Hz, J$_2$=19.0 Hz, 1H), 3.59 (—CH$_3$, s, 3H), 3.61 (—CH, d, J=6.9 Hz, 1H), 7.40 (-Ph, t, 11.9 Hz, 2H), 7.59 (-Ph, t, 21.6 Hz, 2H). MS (ESI):w/z 248.1 [M+H]$^+$.

Other similar compounds can be prepared through the above steps.

IIb was synthesized with II-5b following the method of Example (3); IIc was synthesized with II-5c following the method of Example (3); and IId was synthesized with II-5d following the method of Example (3).

The specific compound synthesized and their properties are shown in a table below.

| No. | Structure | Chemical name and analytical data |
|---|---|---|
| IIb | 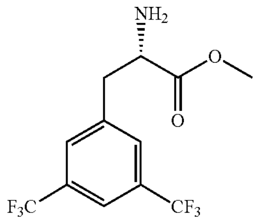 [SMILES: COC(=O)[C@@H](N)Cc1cc(C(F)(F)F)cc(C(F)(F)F)c1] | (S)-methyl 2-amino-3-(3,5-bis(trifluoromethyl) phenyl)propionate<br>Yield 80%. $^1$H NMR (400 MHz, CDCl$_3$) δ 2.99 (—CH$_2$, dd, $J_1$ = 7.9 Hz, $J_2$ = 13.6 Hz, 1H), 3.18 (—CH$_2$, dd, $J_1$ = 4.9 Hz, $J_2$ = 13.7 Hz, 1H), 3.72 (—CH$_3$, s, 3H), 3.73-3.78 (—CH, m, 1H), 7.65 (—Ph, d, 21.5 Hz, 2H), 7.76 (—Ph, s, 1H). MS (ESI): m/z 316.2 |
| IIc | 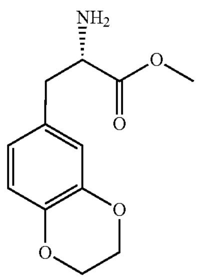 [SMILES: COC(=O)[C@@H](N)Cc1ccc2c(c1)OCCO2] | (S)-methyl 2-amino-3-(3,4-benzodioxinyl)propionate<br>Yield 64.9%. $^1$H NMR (400 MHz, CDCl$_3$) δ 2.74 (—CH$_2$, dd, $J_1$ = 7.9 Hz, $J_2$ = 13.6 Hz, 1H), 2,98 (—CH$_2$, dd, $J_1$ = 5.0 Hz, $J_2$ = 13.6 Hz, 1H), :3.67 (—CH, dd, $J_1$ = 5.0 Hz, $J_2$ = 7.9 Hz, 1H), 3.72 (—CH$_3$, s, 3H), 4.18-4.26 (—CH$_2$, m, 4H), 6.64 (—Ph, dd, $J_1$ = 2.0 Hz, $J_2$ = 8.2 Hz, 1H), 6.69 (—Ph, d, J = 2.0 Hz, 1H), 6.78 (—Ph, d, J = 8.2 Hz, 1H). MS (ESI): m/z 238.2 [M.+ H]$^+$. |
| IId | 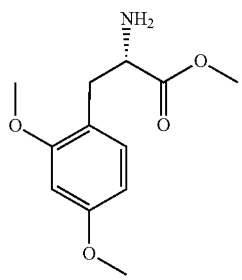 [SMILES: COC(=O)[C@@H](N)Cc1ccc(OC)cc1OC] | (S)-methyl 2-amino-3-(2,4-dimethoxy phenyl)propionate<br>Yield 48.6%. $^1$H NMR (400 MHz, CDCl$_3$) δ 2.71 (—CH$_2$, dd, $J_1$ = 8.1 Hz, $J_2$ = 13.4 Hz, 1H), 2.98 (—CH$_2$, dd, $J_1$ = 5.5 Hz, $J_2$ = 13.4 Hz, IH), 3.63 (—CH$_3$, s, 3H), 3.69 (—CH dd, $J_1$ = 5.5 Hz, $J_2$ = 8.1 Hz, 1H), 3.73 (—CH$_3$, s, 6H), 6.36 (—Ph, dt, $J_1$ = 2.4 Hz, $J_2$ = 8.1 Hz, 2H), 6.93-6.98 (—Ph, m, 1H). MS (ESI): m/z 240.1 [M + H]$^+$, calcd: 239.1. |

II. Production of Compounds of Formula (III)

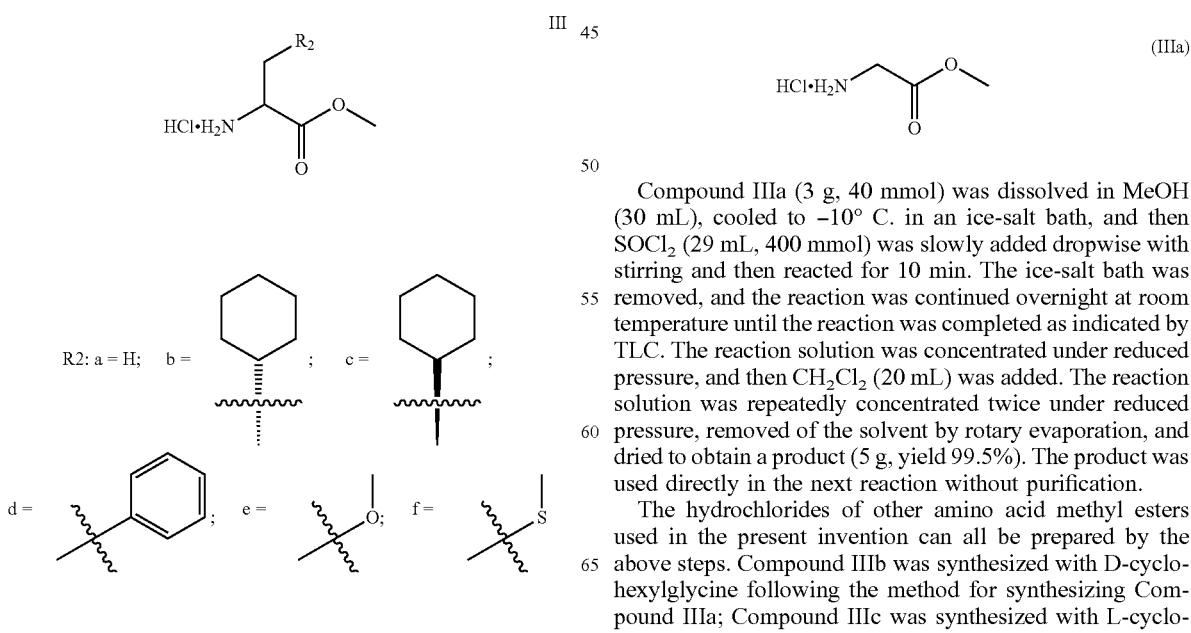

1. Preparation of Glycine Methyl Ester Hydrochloride (IIIa)

Compound IIIa (3 g, 40 mmol) was dissolved in MeOH (30 mL), cooled to −10° C. in an ice-salt bath, and then SOCl$_2$ (29 mL, 400 mmol) was slowly added dropwise with stirring and then reacted for 10 min. The ice-salt bath was removed, and the reaction was continued overnight at room temperature until the reaction was completed as indicated by TLC. The reaction solution was concentrated under reduced pressure, and then CH$_2$Cl$_2$ (20 mL) was added. The reaction solution was repeatedly concentrated twice under reduced pressure, removed of the solvent by rotary evaporation, and dried to obtain a product (5 g, yield 99.5%). The product was used directly in the next reaction without purification.

The hydrochlorides of other amino acid methyl esters used in the present invention can all be prepared by the above steps. Compound IIIb was synthesized with D-cyclohexylglycine following the method for synthesizing Compound IIIa; Compound IIIc was synthesized with L-cyclohexylglycine following the method for synthesizing Compound IIIa; and Compound IIId was synthesized with alanine following the method for synthesizing Compound IIIa.

The specific compound synthesized and their properties are shown in a table below.

| No. | Structure | Chemical name |
|---|---|---|
| IIIb | 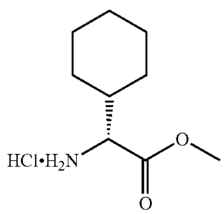 | D-cyclohexylglycine methyl ester hydrochloride |
| IIIc | 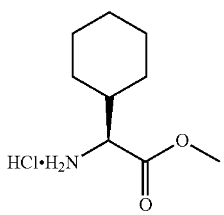 | L-cyclohexylglycine methyl ester hydrochloride |
| IIId | 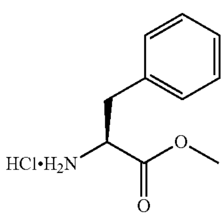 | L-phenylalanine methyl ester hydrochloride |

2. Production of L-O-Methylserine Methyl Ester Hydrochloride (IIIe)

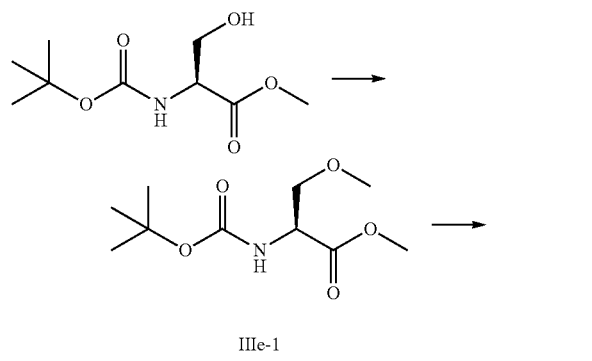

IIIe-1

IIIe (1) Production of BOC-L-O-Methylserine Methyl Ester (IIIe-1)

BOC-L-serine methyl ester (5 g, 22.8 mmol) was dissolved in acetone (110 mL), and then methyl iodide (32 mL, 524 mmol) and silver oxide (8.2 g, 35.4 mmol) were added, condensed and refluxed overnight at 59° C. in the dark until the reaction was completed as indicated by TLC. After filtering, the solvent was removed by evaporation under reduced pressure, and the residue was separated by column chromatography to obtain the target compound as an oil (1.8 g, yield 34.5%). $^1$H NMR (400 MHz, CDCl$_3$) δ 1.43 (—CH$_3$, s, 9H), 3.32 (—CH$_3$, s, 3H), 3.57 (—CH$_2$, dd, J$_1$=3.4 Hz, J$_2$=9.4 Hz, 1H), 3.74 (—CH$_3$, d, 6.3 Hz, 3H), 3.78 (—CH$_2$, dd, J$_1$=3.1 Hz, J$_2$=9.4 Hz, 1H), 4.35-4.44 (—CH, m, 1H), 5.28-5.44 (—CONH, m, 1H). MS (ESI): m/z 234.2 [M+H]$^+$.

(2) Production of L-O-Methylserine Methyl Ester Hydrochloride (IIIe)

Compound IIIe-1 (496 mg, 2.1 mmol) was dissolved in ethyl acetate (2.5 mL), and then a HCl solution (5.2 mL, 21.2 mmol) in ethyl acetate was added dropwise in an ice bath, and reacted for 2 hrs at room temperature until the reaction was completed as indicated by TLC. After filtering, the filter cake was dried under vacuum to obtain a pure product (351 mg, yield 97.5%). $^1$H NMR (400 MHz, CDCl$_3$) δ 3.41 (—CH$_3$, s, 3H), 3.83 (—CH$_3$, s, 3H). 3.95 (—CH$_2$, dd, J$_1$=3.6 Hz, J$_2$=10.4 Hz, 1H), 4.03 (—CH$_2$, dd, J$_1$=2.6 Hz, J$_2$=10.3 Hz, 1H), 4.45 (—CH, s, 1H), 8.70 (—NH$_3^+$, s, 3H).

3. Production of S-methyl-L-cysteine Methyl Ester Hydrochloride (IIIf)

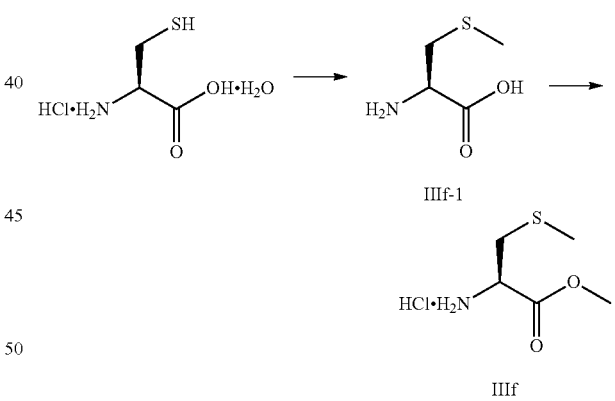

IIIf-1

IIIf (1) Production of S-methyl-L-cysteine (IIIf-1)

L-cysteine hydrochloride monohydrate (3.1 g, 17.5 mmol) was dissolved in MeOH (45 mL), and a 30% sodium methoxide solution (11.2 g, 62 mmol) in methanol was added dropwise in an ice bath. After reaction for 1 h, iodomethane (0.9 mL, 13 mmol) was added dropwise, warmed to room temperature, and reacted for 2 hrs until the reaction was completed as indicated by TLC. The reaction solution was adjusted to pH 5 with 10N HCl, added with ether (40 mL) and stirred for 10 min. After filtering, the filter cake was washed with ether (60 mL), and dried under vacuum, to obtain a crude product (4.715 g).

33

(2) Production of methyl-L-cysteine Methyl Ester Hydrochloride (IIIf)

S-methyl-L-cysteine (4.715 g, 34.9 mmol) was dissolved in MeOH (25 mL), and cooled to −10° C. in an ice-salt bath. SOCl$_2$ (25 mL, 348.8 mmol) was slowly added dropwise with stirring, and then reacted for 10 min. The ice-salt bath was removed, and the reaction was continued overnight at room temperature until the reaction was completed as indicated by TLC. After filtering, the filter cake was washed with CH$_2$Cl$_2$, and dried under vacuum, to obtain pure S-methyl-L-cysteine methyl ester hydrochloride (3.1 g, yield 95.4%). $^1$H NMR (400 MHz, D$_2$O) δ 4.44 (—CH, dd, J=7.7 Hz, 4.6 Hz, 1H), 3.90 (—CH$_3$, s, 3H), 3.23 (—CH$_2$, dd, J=15.1 Hz, 4.6 Hz, 1H), 3.14-3.07 (—CH$_2$, m, 1H), 2.18 (—CH$_3$, s, 3H).

III. Production of Compounds of Formula (I)

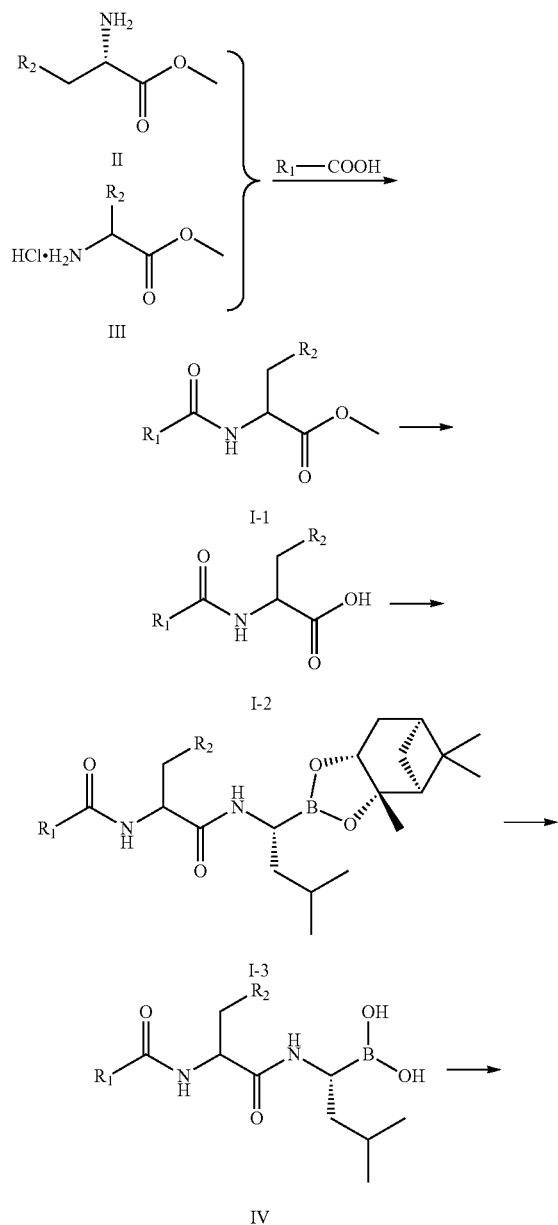

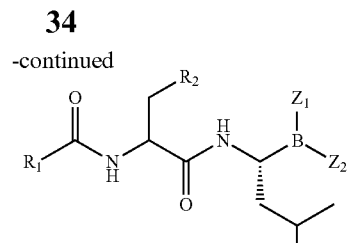

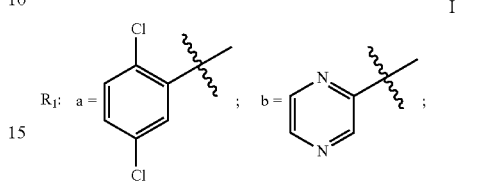

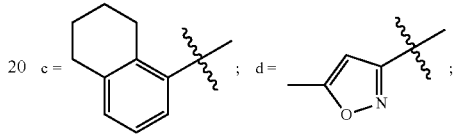

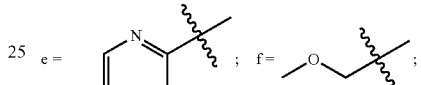

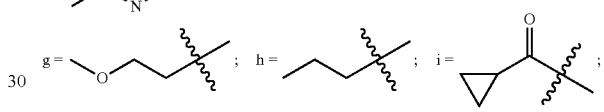

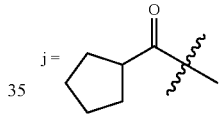

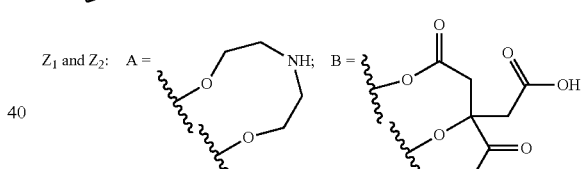

1. Production of (S)—N-(2,5-dichlorobenzoyl)-3-(4-trifluoromethyl phenyl)alanine Methyl Ester (I-1a)

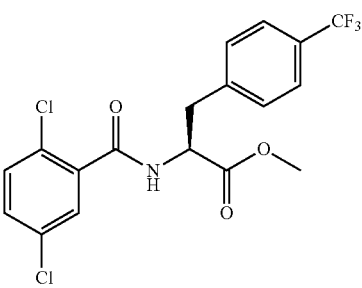 [SMILES: COC(=O)[C@H](Cc1ccc(C(F)(F)F)cc1)NC(=O)c1cc(Cl)ccc1Cl]

2,5-dichlorobenzoic acid (90 mg, 0.47 mmol) and HOBt (92 mg, 0.71 mmol) were dissolved in CH$_2$Cl$_2$ (8 mL), and reacted at −10° C. for 10 min. EDC.HCl (135 mg, 0.7 mmol) was added and reacted for 30 min. Compound IIa (116 mg, 0.47 mmol) was added and reacted for 10 min. The DIPEA (151 mg, 1.17 mmol) was added, reacted for 20 min, heated to room temperature and reacted overnight until the reaction was completed as indicated by TLC. The reaction solution was respectively washed with 10% hydrochloric acid solution (10 mL), 5% NaHCO$_3$ solution (10 mL) and saturated brine (2×10 mL). The CH$_2$Cl$_2$ layer was dried over Na$_2$SO$_4$, filtered, and removed of the solvent by evaporation under reduced pressure to obtain a compound as an oil (166 mg, yield 84.3%). The product was used directly in the next reaction without purification.

In view of the high yield of the product obtained by the condensation method with EDC.HCl, other amino acid methyl esters with an unprotected amino group used in the present invention could be prepared by the condensation method with EDC.HCl as described in Example 1, and all methyl esters were used directly in the next reaction without purification.

Compound I-1b was synthesized with 2,5-dichlorobenzoic acid and IIb following the condensation method with EDC.HCl; Compound I-1c was synthesized with 2,5-dichlorobenzoic acid and IIe following the condensation method with EDC.HCl; and Compound I-1d was synthesized with 2,5-dichlorobenzoic acid and IId following the condensation method with EDC.HCl.

(1) Production of (S)—N-(2,5-dichlorobenzoyl) glycine Methyl Ester (I-1e)

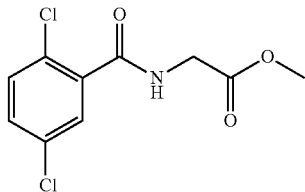 [SMILES: COC(=O)CNC(=O)c1cc(Cl)ccc1Cl]

2,5-dichlorobenzoic acid (7.6 g, 40 mmol) and HOBt (8.1 g, 40 mmol) were dissolved in CH$_2$Cl$_2$ (200 mL), and reacted at −10° C. for 10 min. EDC.HCl (11.5 g, 60 mmol) was added and reacted for 30 min. Compound IIIa (5 g, 40 mmol) was added and reacted for 10 min. The DIPEA (18.1 g, 140 mmol) was added, reacted for 20 min, heated to room temperature and reacted overnight until the reaction was completed as indicated by TLC.

The reaction solution was respectively washed with 10% hydrochloric acid solution (200 mL), 5% NaHCO$_3$ solution (200 mL) and saturated brine (2×200 mL). The CH$_2$Cl$_2$ layer was dried over Na$_2$SO$_4$, filtered, and removed of the solvent by evaporation under reduced pressure to obtain a compound as an oil (9.32 g, yield 88.9%). The product was used directly in the next reaction without purification.

Compound I-1f was synthesized with 2,5-dichlorobenzoic acid and IIIb following the condensation method with EDC.HCl; Compound I-1g was synthesized with 2,5-dichlorobenzoic acid and IIIc following the condensation method with EDC.HCl; Compound I-1h was synthesized with 2,5-dichlorobenzoic acid and IIIe following the condensation method with EDC.HCl; Compound I-1i was synthesized with 2,5-dichlorobenzoic acid and IIIf following the condensation method with EDC.HCl; Compound I-1j was synthesized with 2-pyrazinecarboxylic acid and IIa following the condensation method with EDC.HCl; Compound I-1k was synthesized with 2-pyrazinecarboxylic acid and IIc following the condensation method with EDC.HCl; Compound I-1l was synthesized with 5,6,7,8-tetrahydro-1-Naphthalenecarboxylic acid and IIe following the condensation method with EDC-HCl; and Compound I-1m was synthesized with 5-methylisoxazol-3-carboxylic acid and IIIa following the condensation method with EDC.HCl. Compound I-1n was synthesized with 5-methyl-2-pyrazinecarboxylic acid and IIId following the condensation method with EDC.HCl.

Other amino acid methyl esters with a protected amino group used in the present invention could be prepared by the condensation method with EDC.HCl as described in Example (1), and all methyl esters were used directly in the next reaction without purification.

(2) Production of(S)—N-(methoxyacetyl)phenylalanine Methyl Ester (I-1o)

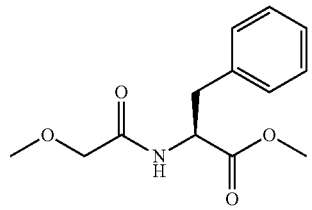

Methoxyacetic acid (280 mg, 3.13 mmol) was dissolved in CH$_2$Cl$_2$ (6 mL), and SOCl$_2$ (0.25 mL, 3.45 mmd) was added dropwise at −10° C. Then, the temperature was raised to room temperature and the reaction was continued for 2 hrs. The methoxyacetyl chloride solution was directly used in the next step. IIId (0.67 g, 3.13 mmol) was dissolved in CH$_2$Cl$_2$ (3 mL), triethylamine (1.58 g, 15.65 mmol) was added, and the methoxyacetyl chloride solution was added dropwise and reacted overnight until the reaction was completed as indicated by TLC. The reaction solution was washed with water, dried over Na$_2$SO$_4$, and separated by column chromatography to obtain the target compound as an oil (0.69 g, yield 87.3%).

Compound I-1p was synthesized with 3-methoxypropanoic acid and IIId following the condensation method with acyl chloride; Compound I-1q was synthesized with butanoic acid and IIId following the condensation method with acyl chloride; Compound I-1r was synthesized with cyclopropylcarboxylic acid and IIId following the condensation method with acyl chloride; and Compound I-1s was synthesized with cyclopentylcarboxylic acid and IIId following the condensation method with acyl chloride.

Other amino acid methyl esters with a protected amino group used in the present invention could be prepared from an alkylcarboxylic acid by the condensation method as described in Example (2), and all methyl esters were used directly in the next reaction without purification.

The specific compound synthesized and their properties are shown in a table below.

| No. | Structure | Chemical name |
|---|---|---|
| I-1b | 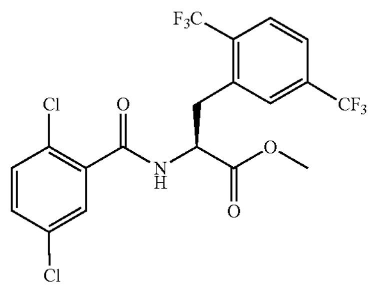 [SMILES: COC(=O)[C@H](Cc1cc(C(F)(F)F)ccc1C(F)(F)F)NC(=O)c1cc(Cl)ccc1Cl] | (S)-N-(2,5-dichlorobenzoyl)-3-(3,5-bis(trifluoromethyl)phenyl)alanine methyl ester |
| I-1c | 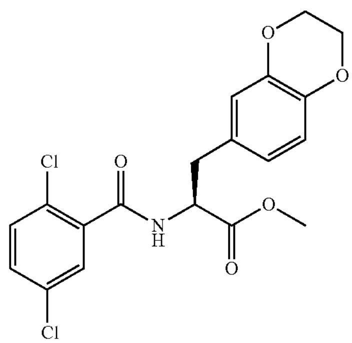 [SMILES: COC(=O)[C@H](Cc1ccc2c(c1)OCCO2)NC(=O)c1cc(Cl)ccc1Cl] | (S)-N-(2,5-dichlorobenzoyl)-3-(2,3-dihydro-1,4-benzodioxol-6-yl)alanine methyl ester |
| I-1d | 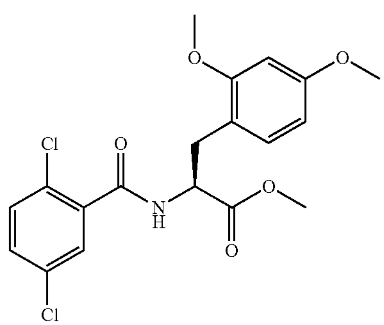 [SMILES: COC(=O)[C@H](Cc1ccc(OC)cc1OC)NC(=O)c1cc(Cl)ccc1Cl] | (S)-N-(2,5-dichlorobenzoyl)-3-(2,4-dimethoxyphenyl)alanine methyl ester |
| I-1f | 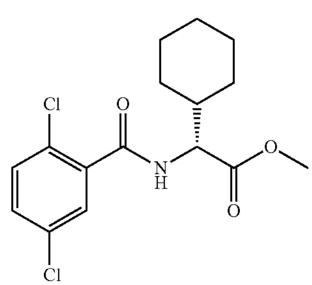 [SMILES: COC(=O)[C@H](NC(=O)c1cc(Cl)ccc1Cl)C1CCCCC1] | (R)-N-(2,5-dichlorobenzoyl)-2-cyclohexylglycine methyl ester |
| I-1g | 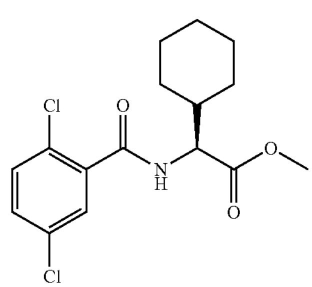 [SMILES: COC(=O)[C@@H](NC(=O)c1cc(Cl)ccc1Cl)C1CCCCC1] | (S)-N-(2,5-dichlorobenzoyl)-2-cyclohexylglycine methyl ester |

-continued

| No. | Structure | Chemical name |
|---|---|---|
| I-1h | 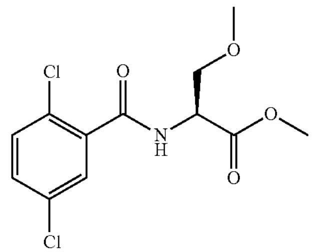 [SMILES: COC[C@H](NC(=O)c1cc(Cl)ccc1Cl)C(=O)OC] | (S)-N-(2,5-dichlorobenzoyl)-3-methoxyalanine methyl ester |
| I-1i | 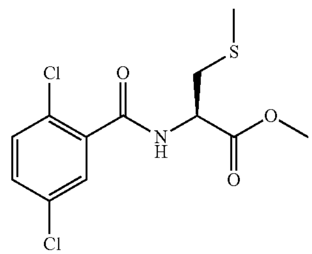 [SMILES: COC(=O)[C@H](CSC)NC(=O)c1cc(Cl)ccc1Cl] | (S)-N-(2,5-dichlorobenzoyl)-3-methylmercaptoalanine methyl ester |
| I-1j | 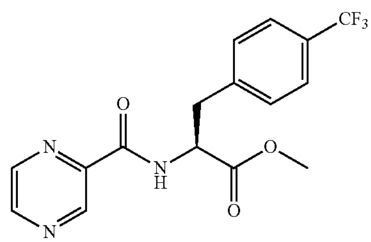 [SMILES: COC(=O)[C@H](Cc1ccc(C(F)(F)F)cc1)NC(=O)c1cnccn1] | (S)-N-(pyrazinylformyl)-3-(4-trifluoromethyl phenyl)alanine methyl ester |
| I-1k | 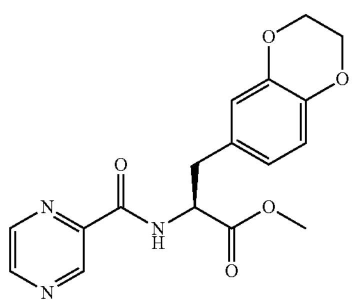 [SMILES: COC(=O)[C@H](Cc1ccc2c(c1)OCCO2)NC(=O)c1cnccn1] | (S)-N-(pyrazinylformyl)-3-(2,3-dihydro-1,4-benzodioxol-6-yl)alanine methyl ester |
| I-1l | 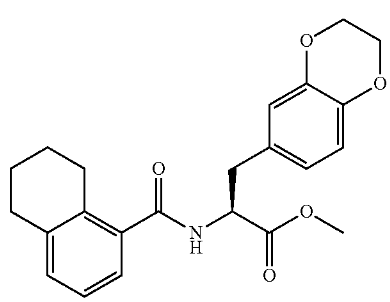 [SMILES: COC(=O)[C@H](Cc1ccc2c(c1)OCCO2)NC(=O)c1cccc2c1CCCC2] | (S)-N-(5,6,7,8-tetrahydro-1-naphthoyl)-3-(2,3-dihydro-1,4-benzodioxol-6-yl)alanine methyl ester |
| I-1m | 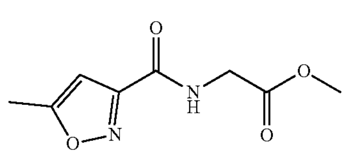 | N-(5-methylisoxazol-3-formyl)glycine methyl ester |

-continued

| No. | Structure | Chemical name |
|---|---|---|
| I-1n | 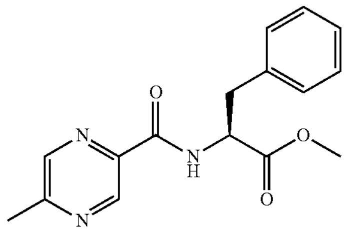 [SMILES: COC(=O)[C@H](Cc1ccccc1)NC(=O)c1cnc(C)cn1] | (S)-N-(5-methyl-2-pyrazinylformyl)phenylalanine methyl ester |
| I-1p | 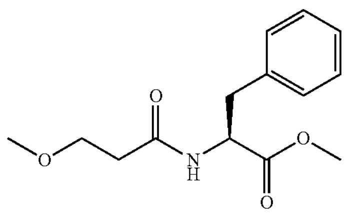 [SMILES: COCCC(=O)N[C@@H](Cc1ccccc1)C(=O)OC] | (S)-N-(3-methoxypropionyl)phenylalanine methyl ester |
| I-1q | 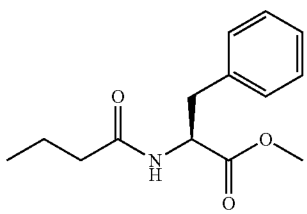 | (S)-N-(butanoyl)phenylalanine methyl ester |
| I-1r | 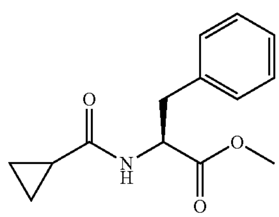 [SMILES: COC(=O)[C@H](Cc1ccccc1)NC(=O)C1CC1] | (S)-N-(cyclopropyl)phenylalanine methyl ester |
| I-1s | 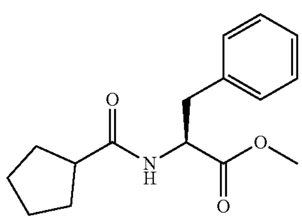 [SMILES: COC(=O)[C@H](Cc1ccccc1)NC(=O)C1CCCC1] | (S)-N-(cyclopentyl)phenylalanine methyl ester |

2. Production of (S)—N-(2,5-dichlorobenzyl)-3-(4-trifluoromethyl phenyl)alanine (I-2a)

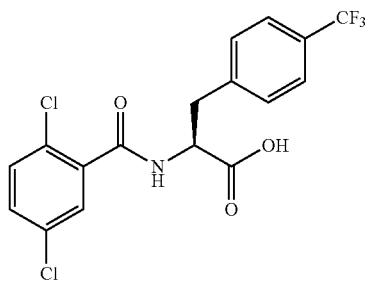 [SMILES: O=C(N[C@@H](Cc1ccc(C(F)(F)F)cc1)C(=O)O)c1cc(Cl)ccc1Cl]

Compound I-1a (129 mg, 0.31 mmol) was dissolved in MeOH (2.5 mL), and then LiOH.H$_2$O (39 mg, 0.92 mmol) and H$_2$O (0.8 mL) were added and reacted for 2 hrs, until the reaction was completed as indicated by TLC. The organic phase was rotary dried, and the aqueous phase was extracted with diethyl ether (2×1 mL). Hydrochloric acid was added dropwise to the aqueous phase to a pH of 2-3, and a large amount of white solid was produced. After extraction with ethyl acetate and removal of the solvent by evaporation under reduced pressure, a white product was obtained (106 mg, yield 86.0%, mp 185.1-186.9° C.). $^1$H NMR (400 MHz, DMSO) δ 3.02 (—CH$_2$, dd, J$_1$=10.6 Hz, J$_2$=13.8 Hz, 1H), 3.30 (—CH$_2$, dd, J$_1$=4.6 Hz, J$_2$=13.9 Hz, 1H), 4.68 (—CH, ddd, J$_1$=4.7 Hz, J$_2$=8.4 Hz, J$_3$=10.4 Hz, 1H), 7.15 (-Ph, d, 1.8 Hz, 1H), 7.49 (-Ph, t, 4.9 Hz, 2H), 7.52 (-Ph, d, 6.0 Hz, 2H), 7.66 (-Ph, d, J=8.1 Hz, 2H), 8.90 (—CONH, d, J=8.2 Hz, 1H), 13.12 (—COOH, s, 1H). MS (ESI): m/z 403.9 [M−H]$^−$.

Other amino acids with a protected amino group used in the present invention could be prepared by the method as described in Example 2.

Compound I-2b was synthesized with I-1b by the method as described in Example 2; Compound I-2c was synthesized with I-1c by the method as described in Example 2; Compound I-2d was synthesized with I-1d by the method as described in Example 2; Compound I-2e was synthesized with I-1e by the method as described in Example 2; Compound I-2f was synthesized with I-1f by the method as described in Example 2; Compound I-2g was synthesized with I-1g by the method as described in Example 2; Compound I-2h was synthesized with I-1h by the method as described in Example 2; Compound I-2i was synthesized with I-1i by the method as described in Example 2; Compound I-2j was synthesized with I-1j by the method as described in Example 2; Compound I-2k was synthesized with I-1k by the method as described in Example 2; Compound I-2l was synthesized with I-1l by the method as described in Example 2; Compound I-2m was synthesized with I-1m by the method as described in Example 2; Compound I-2n was synthesized with I-1n by the method as described in Example 2; Compound I-2o was synthesized with I-1o by the method as described in Example 2; Compound I-2p was synthesized with I-1p by the method as described in Example 2; Compound I-2q was synthesized with I-1q by the method as described in Example 2; Compound I-2r was synthesized with I-1r by the method as described in Example 2; and Compound I-2s was synthesized with I-1s by the method as described in Example 2.

The specific compound synthesized and their properties are shown in a table below.

| No. | Structure | Chemical name and analytical data |
|---|---|---|
| I-2b | 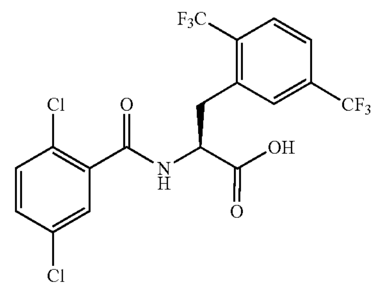 [SMILES: O=C(N[C@@H](Cc1cc(C(F)(F)F)ccc1C(F)(F)F)C(=O)O)c1cc(Cl)ccc1Cl] | (S)-N-(2,5-dichlorobenzoyl)-3-(3,5-bis(trifluoromethyl)phenyl)alanine<br>Yield 97.6%, mp 195.4-196.5° C. $^1$H NMR (400 MHz, DMSO) δ 2.99-3.20 (—CH$_2$, m, 1H), 3.44 (—CH$_2$, dd, J$_1$ = 4.0 Hz, J$_2$ = 13.8 Hz, 1H), 4.61-4.95 (—CH, m, 1H), 7.14 (—Ph, s, 1H), 7.39-7.65 (—Ph, m, 2H), 7.73-8.31 (—Ph, m, 3H), 8.97 (—CONH, d, J = 8.4 Hz, 1H), 13.07 (—COOH, s, 1H). MS (ESI): m/z 471.8 [M − H]$^-$. |
| I-2c | 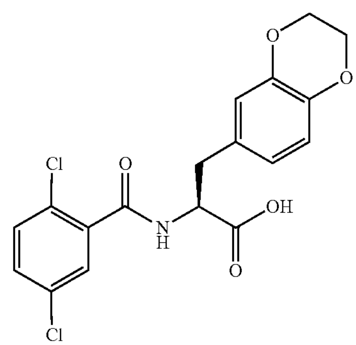 [SMILES: O=C(N[C@@H](Cc1ccc2c(c1)OCCO2)C(=O)O)c1cc(Cl)ccc1Cl] | (S)-N-(2,5-dichlorobenzoyl)-3-(2,3-dihydro-1,4-benzodioxol-6-yl)alanine<br>Yield 98.6%, mp 194.8-196.6° C. $^1$H NMR (400 MHz, DMSO) δ 2.80 (—CH$_2$, dd, J$_1$ = 10.4 Hz, J$_2$ = 13.8 Hz, 1H), 3.06 (—CH$_2$, dd, J$_1$ = 4.6 Hz, J$_2$ = 13.9 Hz, 1H), 4.20 (—CH$_2$, s, 4H), 4.51 (—CH, ddd, J$_1$ = 4.6 Hz, J$_2$ = 8.4 Hz, J$_1$J$_3$ = 10.2 Hz, 1H), 6.73 (—Ph, dd, J$_1$ = 1.8 Hz, J$_2$ = 8.3 Hz, 1H), 6.76 (—Ph, d, 8.1 Hz, 1H), 6.78 (—Ph, d, J = 1.7 Hz, 1H), 7.15-7.22 (—Ph, m, 1H), 7.47-7.57 (—Ph, m, 2H), 8.84 (—CONH, d, J = 8.2 Hz, 1H), 12.94 (—COOH, s, 1H). MS (ESI): m/z 393.8 [M − H]$^-$. |
| I-2d | 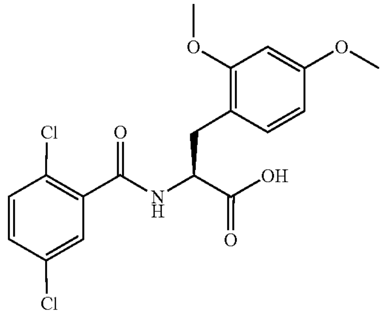 [SMILES: COc1ccc(C[C@H](NC(=O)c2cc(Cl)ccc2Cl)C(=O)O)c(OC)c1] | (S)-N-(2,5-dichlorobenzoyl)-3-(2,4-dimethoxyphenyl)alanine<br>Yield 82.6%, mp 183.4-185.5° C. $^1$H NMR (400 MHz, DMSO) δ 2.72 (—CH$_2$, dt, J$_1$ = 11.8 Hz, J$_2$ = 2:3.6 Hz, 1H), 3.14 (—CH$_2$, dd, J$_1$ = 4.7 Hz, J$_2$ = 13.5 Hz, 1H), 3.73 (—CH$_3$, s, 3H), 3.78 (—CH$_3$, s, 3H), 4.59 (—CH, td, J$_1$ = 4.9 Hz, J$_2$ = 9.6 Hz, 1H), 6.43 (—Ph, dd, J$_1$ = 2.2 Hz, J$_2$ = 8.3 Hz, 1H), 6.53 (—Ph, d, J = 2.1 Hz, 1H), 7.08 (—Ph, d, J = 8.3 Hz, 1H), 7.14 (—Ph, s, 1H), 7.43-7.57 (—Ph, m, 2H), 8.74 (—CONH, d, 8.3 Hz, 1H), 12.83 (—COOH, s, 1H). MS (ESI): m/z 395.9 [M − H]$^-$. |
| I-2e | 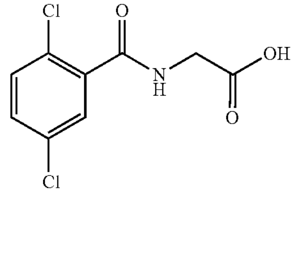 [SMILES: O=C(O)CNC(=O)c1cc(Cl)ccc1Cl] | (S)-N-(2,5-dichlorobenzoyl)glycine<br>Yield 96.9%. mp 169.3-170.8. $^1$H NMR (400 MHz, DMSO) δ 3.91 (—CH$_2$, d, J = 6.0 Hz, 2H), 7.48 (—CONH, d,J = 8.7 Hz, 1H), 7.55 (—Ph, d, J = 1.3 Hz, 2H), 8.89 (—Ph, t, J = 5.9 Hz, 1H), 12.71 (—COOH, s, 1H). MS (ESI): m/z 246.1 [M − H]$^-$. |

-continued

| No. | Structure | Chemical name and analytical data |
|---|---|---|
| I-2f | 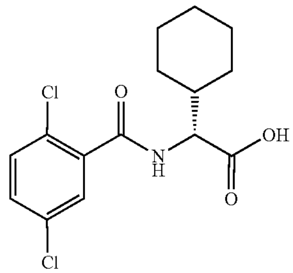 [SMILES: O=C(N[C@@H](C(=O)O)C1CCCCC1)c1cc(Cl)ccc1Cl] | (R)-N-(2,5-dichlorobenzoyl)-2-cyclohexylglycine<br>Yield 87.5%, mp: 155.2-156.1° C. $^1$H NMR (400 MHz, CDCl$_3$) δ 1.09-1.31 (—CH$_2$, m, 5H), 1.78 (—CH$_2$, dt, J$_1$ = 12.4 Hz, J$_2$ = 25.9 Hz, 5H), 2,01 (—CH, ddd, J$_1$ = 4,4 Hz, J$_2$ = 8.2 Hz, J$_3$ = 11 Hz 1H) 4.80 (—CH, dd, J$_1$ = 4.8 Hz, J$_2$ = 8.6 Hz, 1H), 6.85 (—CONH, d, J = 8.5 Hz, 1H), 7.34-7.40 (—Ph, m, 2H), 7.67-7.73 (—Ph, m, 1H). MS (ESI): m/z 328.2 [M − H]$^-$. |
| I-2g | 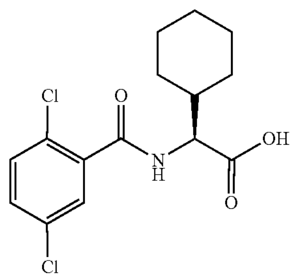 [SMILES: O=C(N[C@H](C(=O)O)C1CCCCC1)c1cc(Cl)ccc1Cl] | (S)-N-(2,5-diehlorobenzoyl)-2-cyclohexylglycine<br>Yield 95.5%, mp: 158,7-160.7° C. $^1$H NMR (400 MHz, CDCl$_3$) δ 1.10-1.29 (—CH$_2$, m, 5H), 1.76 (—CH$_2$, dt, J$_1$ = 12.9 Hz, J$_2$ = 28.1 Hz, 5H), 1.99 (—CH, ddd, J$_1$ = 4.1 Hz, J$_2$ = 7.7 Hz, J$_3$ = 11.6 Hz, 1H), 4.78 (—CH, dd, J$_1$ = 4.8 Hz, J$_2$ = 8.5 Hz, 1H), 6.80 (—CONH, d, J = 8.5 Hz, 1H), 7.34 (—Ph, t, J = 5.0 Hz, 2H), 7.67 (—Ph, dd. J$_1$ = 4.3 Hz, J$_2$ = 5.8 Hz, 1H). MS (ESI): m/z 328.3 [M − H]$^-$. |
| I-2h | 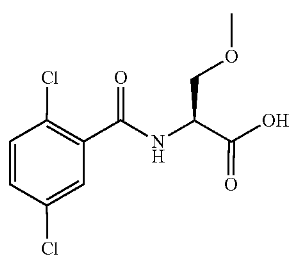 [SMILES: COC[C@H](NC(=O)c1cc(Cl)ccc1Cl)C(=O)O] | (S)-N-(2,5-dichlorobenzoyl)-3-methoxyalanine<br>Yield 40.8%, mp 161.5-162.1° C. $^1$H NMR (400 MHz, DMSO) δ 3.28 (—CH$_3$, s, 3H), 3.63 (—CH$_2$, dd, J$_1$ = 4.2 Hz, J$_2$ = 10.0 Hz, 1H), 3.71 (—CH$_2$, dd, J$_1$ = 6.2 Hz, J$_2$ = 9.9 Hz, 1H), 4.59 (—CH, ddd, J$_1$ = 4.2 Hz, J$_2$ = 6.2 Hz, J$_3$ = 7.8 Hz, 1H), 7.39-7.46 (—Ph, m, 1H), 7.49-7.59 (—Ph, m, 2H), 8.92 (—CONH, d, J = 7.9 Hz, 1H). MS (ESI): m/z 290.1 [M − H]$^-$. |
| I-2i | 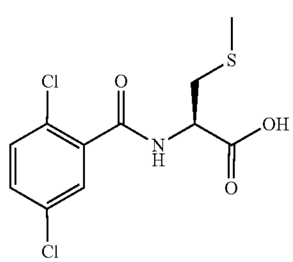 | (R)-N-(2,5-dichlorobenzoyl)-3-methylmercaptoalanine<br>Yield 96.5%, mp 139.1-140.7° C. $^1$H NMR (400 MHz, DMSO) δ 2.12 (—CH$_3$, s, 3H), 2.76-2.85 (—CH$_2$, m, 1H), 2.91-3.01 (—CH$_2$, m, 1H), 4.56 (—CH, td, J$_1$ = 4.9 Hz, J$_2$ = 9.0 Hz, 1H), 7.45 (—Ph, t, J = 1.4 Hz, 1H), 7.54 (—Ph, dd, J$_1$ = 1.4 Hz, J$_2$ = 7.2 Hz, 2H), 8.95 (—CONH, d, J = 8.1 Hz, 1H), 12.96 (—COOH, s, 1H). MS (ESI): m/z 306.1 [M − H]$^-$. |
| I-2j | 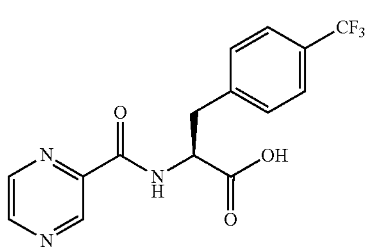 [SMILES: O=C(N[C@@H](Cc1ccc(C(F)(F)F)cc1)C(=O)O)c1cnccn1] | (S)-N-(pyrazinylformyl)-3-(4-trifluoromethyl phenyl)alanine<br>Yield 99.64%. mp 104.8-106.3° C. $^1$H NMR (400 MHz, DMSO) δ 3.1 (—CH$_2$, s, 1H), 3.33-3.47 (—CH$_2$, m, 1H), 4.78 (—CH, td, J$_1$ = 5.4 Hz, J$_2$ = 8.5 Hz, 1H), 7.48 (—Ph, d, J = 8.1 Hz, 2H), 7.61 (—Ph, d, J = 8.2 Hz, 2H), 8.70-8.77 (—Pyz, m, 1H), 8.88 (—Pyz, d, J = 2.5 Hz, 1H), 9.04 (—CONH, d, J = 8.3 Hz, 1H), 9.13 (—Pyz, d, J = 1.3 Hz, 1H), 13.13 (—COOH, s, 1H). MS(ESI): m/z 338.2 [M − H]$^-$. |

| No. | Structure | Chemical name and analytical data |
|---|---|---|
| I-2k | 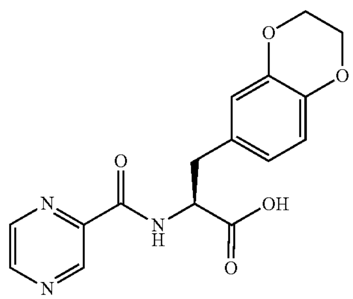 [SMILES: O=C(N[C@@H](Cc1ccc2c(c1)OCCO2)C(=O)O)c1cnccn1] | (S)-N-(pyrazinylforrayl)-3-(2,3-dihydro-1,4-benzodioxol-6-yl)alanine<br>Yield 95.7%, mp 176.3-178.1° C. $^1$H NMR (400 MHz, DMSO) δ 3.00-3.16 (—CH$_2$, m, 2H), 4.09-4.25 (—CH$_2$, m, 4H), 4.63 (—CH, dd, J$_1$ = 7.1 Hz, J$_2$ = 13.9 Hz, 1H), 6.66 (—Ph, dd, J$_1$ = 1.9 Hz, J$_2$ = 8.3 Hz, 1H), 6.71 (—Ph, dd, J$_1$ = 5.1 Hz, J$_2$ = 6.7 Hz, 2H), 8.75 (—Pyz, dd, J$_1$ = 1.5 Hz, J$_2$ = 2.4 Hz, 1H), 8.84 (—CONH, d, J = 8.1 Hz, 1H), 8.89 (—Pyz, d, 2.5 Hz, 1H), 9.15 (—Pyz, d, 1.4 Hz, 1H), 13.10 (—COOH, s, 1H). MS (ESI): m/z 328.2 [M − H]$^-$. |
| I-2l | 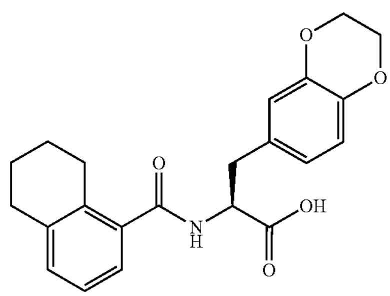 [SMILES: O=C(N[C@@H](Cc1ccc2c(c1)OCCO2)C(=O)O)c1cccc2c1CCCC2] | (S)-N-(5,6,7,8-tetrahydro-1-naphthoyl)-3-(2,3-dihydro-1,4-benzodioxol-6-yl)alanine<br>Yield 99.3%, mp 190.9-192.3° C. $^1$H NMR (400 MHz, DMSO) δ 1.54-1.72, (—CH$_2$, m, 4H), 2.26-2.58 (—CH$_2$, m, 2H), 2.71 (—CH$_2$, t, J = 6.1 Hz, 2H), 2.78 (—CH$_2$, dd, J$_1$ = 10.6 Hz, J$_2$ = 13.7 Hz, 1H), 3.04 (—CH$_2$, dd, J$_1$ = 4.2 Hz, J$_2$ = 13.7 Hz, 1H), 4.19 (—CH$_2$, s, 4H), 4.42-4.54 (—CH, m, 1H), 6.71 (—Ph, d, 8.3 Hz, 1H), 6.75 (—Ph, d, J = 8.2 Hz, 1H), 6.77 (—Ph, s, 1H), 6.93 (—Ph, dd, J$_1$ = 4.3 Hz, J$_2$ = 8.4 Hz, 1H), 7.04-7.13 (—Ph, m, 2H), 8.29 (CONH, d, J = 7.9 Hz, 1H), 12.91 (—COOH, s, 1H). MS (ESI): m/z 380.2 [M − H]$^-$. |
| I-2m | 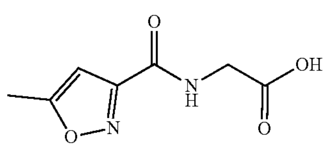 | N-(5-methylisoxazol-3-formyl)glycine<br>Yield 90.8%, mp 128.5-130.1° C. $^1$H NMR (400 MHz, DMSO) δ 2.46 (—CH$_3$, d, J = 3.1 Hz, 3H), 3.89 (—CH$_2$, d, J = 6.0 Hz, 2H), 6.56 (—CH, d, J = 4.3 Hz, 1H), 8.90 —CONH, t, J = 5.8 Hz, 1H), 12.79 (—COOH, s, 1H). MS (ESI): m/z 183.2 [M − H]$^-$. |
| I-2n | 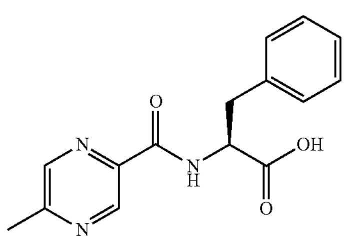 | (S)-N-(5-methyl-2-pyrazinylformyl)phenylalanine<br>Yield 85.2%, mp 208.2-209.6° C. $^1$H NMR(400 MHz, DMSO) δ 2.43-2.51 (—CH$_3$, m, 3H), 3.21-3.23 (—CH$_2$, m, 2H), 4.71-4.77 (—CH, m, 1H), 7.18-7.24 (—Ph, m, 5H), 8.62 (—Pyz, s, 1H), 8.77 (—CONH, d, J = 8.2 Hz, 1H), 9.00 (—Pyz, s, 1H). MS (ESI): m/z 316.4 [M − H]$^-$. |
| I-2o | 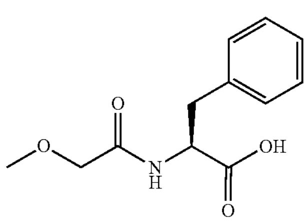 [SMILES: COCC(=O)N[C@@H](Cc1ccccc1)C(=O)O] | (S)-N-(methoxyacetyl)phenylalanine<br>Yield 74.4%, mp 82.8-83.9° C. $^1$H NMR (400 MHz, CDCl$_3$) δ 3.13 (—CH2, dd J1 = 6.6 Hz, J$_2$ = 14.0 Hz, 1H), 3.25 (—CH$_2$, dd, J$_1$ = 5.5 Hz, J$_2$ = 14.0 Hz, 1H), 3.32 (—CH$_3$, s, 3H), 3.89 (—CH$_2$, s, 2H), 4.90 (—CH, dd, J$_1$ = 6.4 Hz, J$_2$ = 13.7 Hz, 1H), 7.01 (—CONH., d, J = 7.9 Hz, 1H), 7.18 (—PH, d, 6.8 Hz, 2H), 7.23-7.32 (—Ph, m, 3H), 7.66 (—COOH, s, 1H). MS (ESI): m/z 236.22 [M − H]$^-$. |
| I-2p | 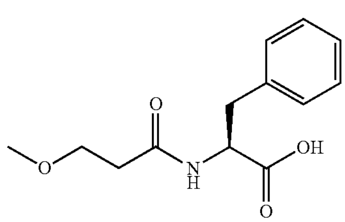 [SMILES: COCCC(=O)N[C@@H](Cc1ccccc1)C(=O)O] | (S)-N-(3-methoxypropionyl)phenylalanine<br>Yield 70.8%, mp 62.8-64.7° C. $^1$H NMR (400 MHz, CDCl$_3$) δ 2.44 (—CH$_2$, t, J = 5.7 Hz, 2H), 3.12 (—CH$_2$, qd, J$_1$ = 5.8 Hz, J$_2$ = 13.9 Hz, 2H), 3.27 (—CH$_3$, s, 3H), 3.56 (—PhCH$_2$, dt, J$_1$ = 2.8 Hz, J$_2$ = 10.3 Hz, 2H), 3.71 (—CH$_3$, s, 3H), 4.84-4.91 (—CH, m, 1H), 6,74 (—CONH, d, J = 6.7 Hz, 1H), 7.11 (—Ph, d, J = 6.8 Hz, 2H), 7.24-7.31 (—Ph, m, 3H). MS (ESI): m/z 250.17 [M − H]$^-$. |

| No. | Structure | Chemical name and analytical data |
|---|---|---|
| I-2q | 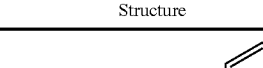 | (S)-N-(butanoyl)phenylalanine<br>Yield 95.6%, mp 113.3-114.7° C. $^1$H NMR (400 MHz, CDCl$_3$) δ 0.90 (—CH$_3$, t, J = 7.2 Hz, 3H), 1.61 (—CH$_2$, dd, J = 14.2, 7.0 Hz, 2H), 2.17 (—CH$_2$, t, J = 6.8 Hz, 2H), 3.04-3.35 (PhCH$_2$, m, 2H), 4.89 (—COOH, s, 1H), 5.90 (—CONH, s, 1H), 7.17 (—Ph, d, J = 6.7 Hz, 2H), 7.30 (—Ph, dd, J = 12.8, 5.9 Hz, 3H). MS (ESI): m/z 234.18 [M − H]$^−$. |

3. Production of (S)—N-(2,5-dichlorobenzoyl)-3-(4-trifluoromethyl phenyl)propionamido-D-leucine borate-(+)-α-pinanediol ester (I-3a)

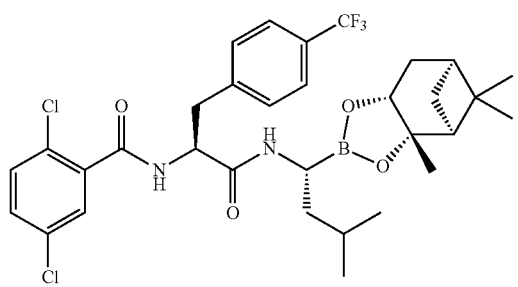 [SMILES: CC(C)C[C@H](NC(=O)[C@H](Cc1ccc(C(F)(F)F)cc1)NC(=O)c1cc(Cl)ccc1Cl)B1O[C@@H]2C[C@@H]3C[C@@H](C3(C)C)[C@]2(C)O1]

Compound I-2a (340 mg, 0.84 mmol) and HOBt (218 g, 1.67 mmol) were dissolved in CH$_2$Cl$_2$ (18 mL), and reacted at −10° C. for 10 min. EDC.HCl (321 mg, 1.67 mmol) was added and reacted for 30 min. (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate (317 mg, 0.84 mmol) was added and reacted for 10 min. Then DIPEA (433 mg, 3.35 mmol) was added, reacted for 20 min, heated to room temperature and then reacted overnight until the reaction was completed as indicated by TLC. The reaction solution was respectively washed with 10% hydrochloric acid solution (20 mL), 5% NaHCO$_3$ solution (20 mL) and saturated brine (2×20 mL). The CH$_2$Cl$_2$ layer was dried over Na$_2$SO$_4$, filtered, removed of the solvent by evaporation under reduced pressure, and separated by column chromatography to obtain a compound as an oil (480 mg, yield 87.6%). $^1$H NMR (400 MHz, CDCl$_3$) δ 0.82 (—CH$_3$, s, 3H), 0.85 (—CH$_3$, s, 6H), 1.16 (—CH$_2$, dd, J$_1$=7.8 Hz J$_2$=10.8 Hz, 1H), 1.28 (—CH$_3$, s, 3H), 1.32 (—CH$_2$, d, 14.3 Hz, 1H), 1.39 (—CH$_3$, s, 3H), 1.41-1.52 (—CH, m, 1H), 1.63 (—CH, s, 1H), 1.81 (—CH$_2$, dd J$_1$=2.8 Hz, J$_2$=14.5 Hz, 1H), 1.90 (—CH$_2$, d, 2.4 Hz, 1H), 1.98-2.05 (—CH, m, 1H), 2.12-2.23 (—CH$_2$, m, 1H), 2.25-2.38 (—CH$_2$, m, 1H), 3.19 (—CH, dd, J$_1$=8.5 Hz, J$_2$=13.7 Hz, 1H), 3.23-3.31 (—CH$_2$, m, 2H), 4.21-4.34 (—CH, m, 1H), 4.75-4.94 (—CH, m, 1H), 5.90 (—CONH dd, J$_1$=5.6 Hz, J$_2$=22.2 Hz, 1H), 6.94 (—CONH, d, 7.7 Hz, 1H), 7.29-7.36 (-Ph, m, 2H), 7.41 (-Ph, dd. J$_1$=4.2 Hz, J$_2$=7.8 Hz, 2H), 7.51 (-Ph, s, 1H), 7.55 (-Ph, dd, J$_1$=3.7 Hz, J$_2$=8.0 Hz, 2H). MS (ESI): m/z 653.2 [M+H]$^+$.

Other amino acids with a protected amino group used in the present invention could be prepared by the method as described in Example 3.

Compound I-3b was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and 1-2b following the condensation method with EDC.HCl; Compound I-3c was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and I-2c following the condensation method with EDC.HCl; Compound I-3d was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and 1-2d following the condensation method with EDC.HCl; Compound I-3e was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and 1-26 following the condensation method with EDC.HCl; Compound I-3f was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and 1-2f following the condensation method with EDC.HCl; Compound I-3g was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and 1-2g following the condensation method with EDC.HCl; Compound I-3h was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and 1-2h following the condensation method with EDC.HCl; Compound I-3i was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and I-2i following the condensation method with EDC.HCl; Compound I-3j was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and 1-2j following the condensation method with EDC.HCl; Compound I-3k was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and 1-2k following the condensation method with EDC.HCl; Compound I-3l was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and I-2l following the condensation method with EDC.HCl; Compound I-3m was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and 1-2m following the condensation method with EDC.HCl; Compound I-3n was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and I-2n following the condensation method with EDC.HCl; Compound I-3o was synthesized with (aR,3aS,4S,6S,7aR)-hexahydro-3a,8,8-trimethyl-alpha-(2-methylpropyl)-4,6-methano-1,3,2-benzodioxaborolane-2-methylamine 2,2,2-trifluoroacetate and 1-2o following the condensation method with EDC.HCl; Compound I-3p was synthesized with (aR,3aS,4S,6S,7aR)-hexahydro-3a,8,8-trimethyl-alpha-(2-methylpropyl)-4,6-methano-1,3,2-benzodioxaborolane-2-methyl-amine 2,2,2-trifluoroacetate and I-2p following the condensation method with EDC.HCl, and Compound I-3q was synthesized with (aR,3aS,4S,6S,7aR)-hexahydro-3a8,8-trimethyl-alpha-(2-methylpropyl)-4,6-methano-1,3,2-benzodioxaborolane-2-methylamine 2,2,2-trifluoroacetate and I-2q following the condensation method with EDC.HCl.

The specific compound synthesized and their properties are shown in a table below.

| No. | Structure | Chemical name and analytical data |
|---|---|---|
| I-3b | 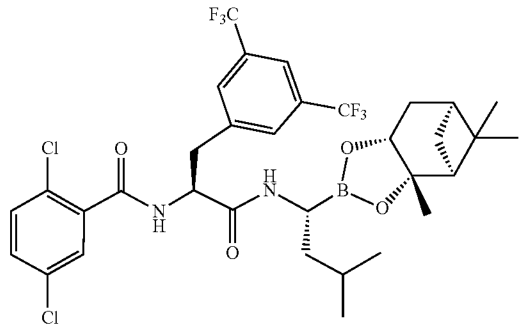 [SMILES: CC(C)C[C@H](NC(=O)[C@H](Cc1cc(C(F)(F)F)cc(C(F)(F)F)c1)NC(=O)c1cc(Cl)ccc1Cl)B1O[C@@H]2C[C@@H]3C[C@@H](C3(C)C)[C@]2(C)O1] | (S)-N-(2,5-dichlorobenzoyl)-3-(3,5-bis(trifluoromethyl)phenyl)propionamido-D-leucine borate-(+)-α-pinanediol ester Yield 76.7%, $^1$H NMR (400 MHz, CDCl$_3$) δ 0.83 (—CH$_3$, s, 3H), 0.86 (—CH$_3$, s, 6H), 1.13 (—CH$_2$, d, J = 10.8 Hz, 1H), 1.23 (—CH$_2$, d, J = 20.0 Hz, 1H), 1.28 (—CH$_3$, s, 3H), 1.39 (—CH$_3$, s, 3H), 1.50 (—CH, ddd, J$_1$ = 6.6 Hz, J$_2$ = 13.8 Hz, J$_3$ = 27.3 Hz, 1H), 1.62 (—CH, s, 1H), 1.79 (—CH$_2$, d, J = 14.6 Hz, 1H), 1.86-1.94 (—CH$_2$, m, 1H), 1.97-2.06 (—CH, m, 1H), 2.11-2.24 (—CH$_2$, m, 1H), 2.32 (—CH$_2$, ddd, J$_1$ = 3.0 Hz, J$_2$ = 7.4 Hz, J$_3$ = 11.3 Hz, 1H), 3.23-3.29 (—CH, m, 1H), 3.29-3.39 (—CH$_2$, m, 2H), 4.20-4.33 (—CH, m, 1H), 4.88 (—CH, dq, J$_1$ = 7.7 Hz, J$_2$ = 13.5 Hz, 1H), 5.96 (—CONH, dd, J$_1$ = 6.1 Hz, J$_2$ = 24.3 Hz, 1H), 6.99 (—CONH, dd, J$_1$ = 4.7 Hz, J$_2$ = 7.6 Hz, 1H), 7.30-7.37 (—Ph, m, 2H), 7.49-7.57 (—Ph, m, 1H), 7.77 (—Ph, d, J = 5.2 Hz, 3H). MS (ESI): m/z 721.3 [M + H]$^+$. |
| I-3c | 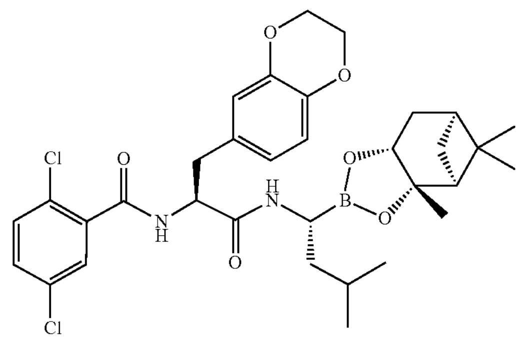 [SMILES: CC(C)C[C@H](NC(=O)[C@H](Cc1ccc2c(c1)OCCO2)NC(=O)c1cc(Cl)ccc1Cl)B1O[C@@H]2C[C@@H]3C[C@@H](C3(C)C)[C@]2(C)O1] | (S)-N-(2,5-dichlorobenzoyl)-3-(2,3-dihydro-1,4-benzodioxol-6-yl)propionamido-D-leucine borate-(+)-α-pinanediol ester Yield 90.6%. $^1$H NMR (400 MHz, CDCl$_3$) δ 0.83 (—CH$_3$, s, 3H), 0.87 (—CH$_3$, s, 6H), 1.21 (—CH$_2$, dd, J$_1$ = 10.5 Hz, J$_2$ = 21.3 Hz, 2H), 1.28 (—CH$_3$, s, 3H), 1.41 (—CH$_3$, s, 3H), 1.43-1.54 (—CH, m, 1H), 1.61 (—CH, d, J = 44.5 Hz, 1H), 1.86 (—CH$_2$, dddd, J$_1$ = 3.3 Hz, J$_2$ = 6.1 Hz, J$_3$ = 9.3 Hz, J$_4$ = 14.5 Hz, 2H), 1.98-2.07 (—CH, m, 1H), 2.12-2.25 (—CH$_2$, m, 1H), 2.27-2.39 (—CH$_2$, m, 1H), 2.91-3.08 (—CH, m, 1H), 3.08-3.28 (—CH$_2$, m, 2H), 4.23 (—CH$_2$, s, 4H), 4.30 (CH, ddd, J$_1$ = 1.9 Hz, J = 8.8 Hz, J$_3$ = 13.7 Hz, 1H), 4.70-4.80 (—CH, m, 1H), 5.91 (—CONH, dd, J$_1$ = 5.2 Hz, J$_2$ = 60.5 Hz, 1H), 6.74 (—Ph, dd, J$_1$ = 1.7 Hz, J$_2$ = 8.2 Hz, 1H), 6.78 (—Ph, d, J = 3.4 Hz, 1H), 6.80 (—Ph, dd, J$_1$ = 2.7 Hz, J$_2$ = 4.6 Hz, 1H), 6.86 (—CONH, t, J = 7.6 Hz, 1H), 7.28-7.34 (—Ph, m, 2H), 7.46-7.55 (—Ph, m, 1H). MS (ESI): m/z 643.3 [M + H]$^+$. |
| I-3d | 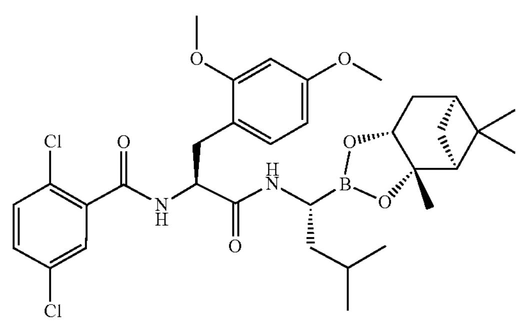 [SMILES: COc1ccc(C[C@H](NC(=O)c2cc(Cl)ccc2Cl)C(=O)N[C@@H](CC(C)C)B2O[C@@H]3C[C@@H]4C[C@@H](C4(C)C)[C@]3(C)O2)c(OC)c1] | (S)-N-(2,5-dichlorobenzoyl)-3-(2,4-dimethoxy phenyl)propionamido-D-leucine borate-(+)-α-pinanediol ester Yield 68.6%. $^1$H NMR (400 MHz, CDCl$_3$) δ 0.84 (—CH$_3$, s, 3H), 0.87 (—CH$_3$, s, 6H), 1.22 (—CH$_2$, d, 3.2 Hz, 1H), 1.28 (—CH$_3$, s, 3H), 1.32-1.39 (—CH$_2$, m, 1H), 1.40 (—CH$_3$, s, 3H), 1.47-1.59 (—CH, m, 1H), 1.60-1.70 (—CH, m, 1H), 1.79-1.87 (—CH$_2$, m, 1H), 1.91 (—CH$_2$, d, J = 13.3 Hz, 1H), 2.01-2.05 (—CH, m, 1H), 2.19 (—CH$_2$, dt, J$_1$ = 7.2 Hz, J$_2$ = 11.2 Hz, 1H), 2.27-2.39 (—CH$_2$, m, 1H), 2.99-3.11 (—CH, m, 1H), 3.18 (—CH$_2$, dt, J$_1$ = 7.7 Hz, J$_2$ = 14.6 Hz, 2H), 3.76 (—CH$_3$, s, 3H) 3.81 (—CH$_3$, s, 3H), 4.25-4.34 (—CH, m, 1H), 4.70-4.83 (—CH, m, 1H), 6.25-6.54 (—Ph, m, 3H), 7.01 (—CONH, d, J = 7.1 Hz, 1H), 7.11 (—CONH, dd, J$_1$ = 5.4 Hz, J$_2$ = 8.9 Hz, 1H), 7.33 (—Ph, dd, J$_1$ = 8.9 Hz, J$_2$ = 10.3 Hz, 3H). MS (ESI): m/z 645.4 [M + H]$^+$. |

| No. | Structure | Chemical name and analytical data |
|---|---|---|
| I-3e | 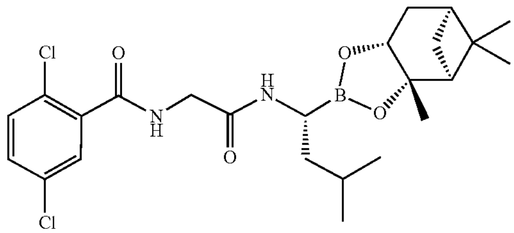 [SMILES: CC(C)C[C@H](NC(=O)CNC(=O)c1cc(Cl)ccc1Cl)B1O[C@@H]2C[C@@H]3C[C@@H](C3(C)C)[C@]2(C)O1] | N-(2,5-dichlorobenzoyl)acetamido-D-leucine borate-(+)-α-pinanediol ester<br>Yield 78.0%. $^1$H NMR (400 MHz, CDCl$_3$) δ 0.83 (—CH$_3$, s, 3H), 0.91 (—CH$_3$, s, 6H), 1.19 (—CH$_2$, d, J = 10.8 Hz, 1H), 1.24 (—CH$_2$, d, J = 7.1 Hz, 1H), 1.27(—CH$_3$, s, 3H), 1.38 (—CH$_3$, s, 3H), 1.59-1.69 (—CH, m, 1H), 1.70 (—CH, s, 1H), 1.77-1.85 (—CH$_2$, m, 1H), 1.86-1.92 (—CH$_2$, m, 1H), 1.96-2.01 (—CH, m, 1H), 2.11-2.21 (—CH$_2$, m, 1H), 2.25-2.36 (—CH$_2$, m, 1H), 3.31 (—CH, dd, J$_1$ = 6.2 Hz, J$_2$ = 14.5 Hz, 1H), 4.15 (—CH$_2$, d, J = 5.3 Hz, 2H), 4.28 (—CH, dt, J$_1$ = 6.3 Hz, J$_2$ = 12.5 Hz, 1H), 6.39 (—CONH, d, J = 5.1 Hz, 1H), 7.24 (—CONH, d, J = 4.6 Hz, 1H), 7.34 (—Ph, d, J = 1.4 Hz, 2H), 7.58-7.65 (—Ph, m, 1H). MS (ESI): m/z 495.3 [M + H]$^+$. |
| I-3f | 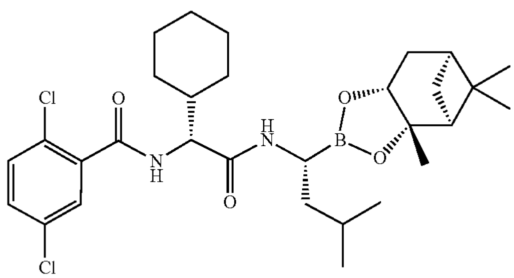 | (R)-N-(2,5-dichlorobenzoyl)-2-cyclohexylacetamido-D-leucine borate-(+)-α-pinanediol ester<br>Yield 60.6%. $^1$H NMR (400 MHz, CDCl$_3$) δ 0.83 (—CH$_3$, s, 3H), 0.90 (—CH$_3$, s, 6H), 1.02-1.23 (—CH$_2$, m, 5H), 1.27 (—CH$_3$, s, 3H), 1.30-1.35 (—CH, m, 1H), 1.37 (—CH$_3$, s, 3H), 1.41-1.46 (—CH, m, 1H), 1.46-1.52 (—CH$_2$, m, 1H), 1.62-1.66 (—CH, m, 1H), 1.71-1.84 (m, 5H), 1.86 (—CH$_2$, dd, J$_1$ = 3.3 Hz, J$_2$ = 5.4 Hz, 2H), 1.89 (—CH, dd, J$_1$ = 2.6 Hz, J$_2$ = 5.4 Hz, 1H), 2.02 (—CH, t, J = 5.5 Hz, 1H), 2.13-2.20 (—CH$_2$, m, 1H), 2.28-2.38 (—CH$_2$, m, 1H), 3.21 (—CH, dt, J$_1$ = 5.9 Hz, J$_2$ = 9.2 Hz, 1H), 4.30 (—CH, dd, J$_1$ = 2.0 Hz, J$_2$ = 8.8 Hz, 1H), 4.46 (—CH, dd, J$_1$ = 1.1 Hz, J$_2$ = 8.6 Hz, 1H), 6.32 (—CONH, d, J = 5.5 Hz, 1H), 6.82 (—CONH, d, J = 8.8 Hz, 1H), 7.31-7.33 (—Ph, m, 2H), 7.55 (—Ph, dd, J$_1$ = 1.1 Hz, J$_2$ = 1.7 Hz, 1H). MS (ESI): m/z 511.4 [M + H]$^+$. |
| I-3g | 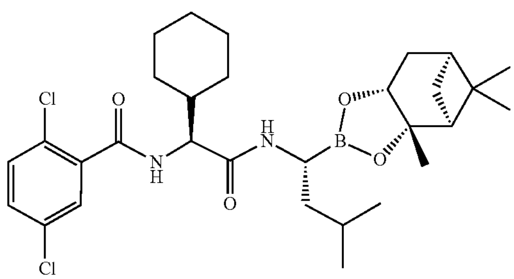 | (S)-N-(2,5-dichlorobenzoyl)-2-cyclohexylacetamido-D-leucine borate-(+)-α-pinanediol ester<br>Yield 73.1%. $^1$H NMR(400 MHz, CDCl$_3$) δ 0.85 (—CH$_3$, s, 3H), 0.89 (—CH$_3$, m, 6H), 1.00-1.23 (—CH$_2$, m, 5H), 1.27 (—CH$_3$, s, 3H), 1.28-1.34 (—CH, m, 1H), 1.37 (—CH$_3$, s, 3H), 1.43-1.51 (—CH$_2$, m, 1H), 1.52-1.63 (—CH$_2$, m, 1H), 1.65 (—CH, d, J = 5.7 Hz, 1H), 1.77 (—CH$_2$, d, J = 11.0 Hz, 5H), 1.83 —CH$_2$, d, J = 11.1 Hz, 2H), 1.88 (—CH, s, 1H), 2.00 (—CH, dd, J$_1$ = 5.8 Hz, J$_2$ = 11.2 Hz, 1H), 2.16 (—CH$_2$, dt, J = 5.1 Hz, J$_1$J$_2$ = 10.7 Hz, 1H), 2.26-2.36 (—CH$_2$, m, 1H), 3.15-3.27 (—CH, m, 1H), 4.29 (—CH, dd, J$_1$ = 1.8 Hz, J$_2$ = 8.7 Hz, 1H), 4.47-4.54 (—CH, m, 1H), 6.42-6.58 (—CONH, m, 1H), 6.96 (—CONH, ddd, J$_1$ = 9.0 Hz, J$_2$ = 16.0 Hz, J$_3$ = 22.4 Hz, 1H), 7.32 (—Ph, s, 2H), 7.55 (—Ph, d, J = 1.6 Hz, 1H). MS (ESI): m/z 511.4 [M + H]$^+$. |
| I-3h | 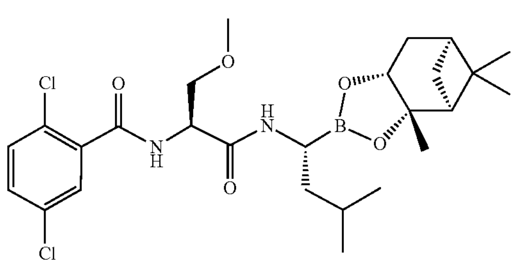 | (S)-N-(2,5-dichlorobenzoyl)-3-methoxypropionamido-D-leucine borate-(+)-α-pinanediol ester<br>Yield 80.8%. $^1$H NMR (400 MHz, CDCl$_3$) δ 0.84 (—CH$_3$, s, 3H), 0.92 (—CH$_3$, s, 3H), 1.17-1.27 (—CH$_2$, m, 2H), 1.29 (—CH$_3$, s, 3H), 1.38 (—CH$_3$, s, 3H), s, 3H), 1.46-1.52 (—CH, m, 1H), 1.57-1.68 (—CH, m, 1H), 1.79-195 (—CH$_2$, m, 2H), 2.02 (—CH, ddd, J$_1$ = 4.7 Hz, J$_2$ = 10.0 Hz, J$_3$ = 15.1 Hz, 1H), 2.14-2.23 (—CH$_2$, m, 1H), 2.28-2.37 (—CH$_2$, m, 1H), 3.27-3.37 (—CH$_2$, m, 1H), 3.41 (—CH$_3$, s, 3H), 3.50 (—CH$_2$, ddd, J$_1$ = 5.6 Hz, J$_2$ = 9.6 Hz, J$_3$ = 16.9 Hz, 1H), 3.92 (—CH, dt, J$_1$ = 4.0 Hz, J$_2$ = 9.0 Hz, 1H), 4.26-4.35 (—CH, m, 1H), 4.68 (—CH, dddd, J$_1$ = 3.9 Hz, J$_2$ = |

| No. | Structure | Chemical name and analytical data |
|---|---|---|
| | | 7.1 Hz, J$_3$ = 10.8 Hz, J$_4$ = 18.0 Hz, 1H), 6.41-6.74 (—CONH, m, 1H), 7.11-7.23 (—CONH, m, 1H), 7.30-7.37 (—Ph, m, 2H), 7.64 (—Plv d, J = 7.4 Hz, 1H). MS (ESI): m/z 539.4 [M + H]$^+$. |
| I-3i | 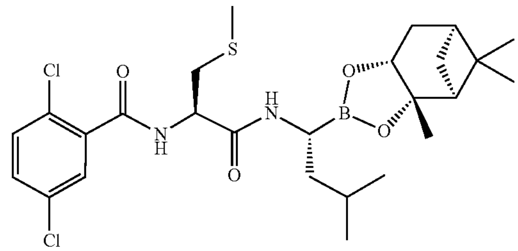 | (R)-N-(2,5-dichlorobenzoyl)-3-methylmercaptopropionamido-D-leucine borate-(+)-α-pinanediol ester<br>Yield 71.3%. $^1$H NMR(400 MHz, CDCl$_3$) δ 0.82 (—CH$_3$, s, 3H), 0.92 (—CH$_3$, s, 3H), 1.23 (—CH$_2$, dd, J$_1$ = 5.9 Hz, J$_2$ = 10.2 Hz, 2H), 1.28 (—CH$_3$, s, 3H), 1.38 (—CH$_3$, s, 3H), 1.46 (—CH, ddd, J$_1$ = 4.6 Hz, J$_2$ = 6.9 Hz, J$_3$ = 15.2 Hz, 1H), 1.80-1.87 (—CH$_2$, m, 1H), 1.90 (—CH$_2$, dd, J$_1$ = 5.6 Hz, J$_2$ = 8.2 Hz, 1H), 2.00-2.06 (—CH$_2$, m, 2H), 2.13-2.21 (—CH, m, 1H), 2.23 (—CH$_3$, s, 3H), 2.32 (—CH, dt, J$_1$ = 7.8 Hz, J$_2$ = 18.5 Hz, 1H), 2.85 (—CH$_2$, ddd, J$_1$ = 2.2 Hz, J$_2$ = 7.9 Hz, J$_3$ = 14.0 Hz, 1H), 3.05 (—CH$_2$, dt, J$_1$ = 4.6 Hz, J$_2$ = 14.0 Hz, 1H), 3.27-3.42 (—CH, m, 1H), 4.31 (—CH, ddd, J$_1$ = 2.0 Hz, J$_2$ = 4.1 Hz, J$_3$ = 8.7 Hz, 1H), 4.65-4.76 (—CH, m, 1H), 6.64 (—CONH, dd, J$_1$ = 5.9 Hz, J$_2$ = 30.5 Hz, 1H), 7.21-7.30 (—CONH, m, 1H), 7.35 (—Ph, t, J = 1.5 Hz, 2H), 7.63 (—Ph, s, 1H). MS (ESI): m/z 555.2 [M + H]$^+$. |
| I-3j | 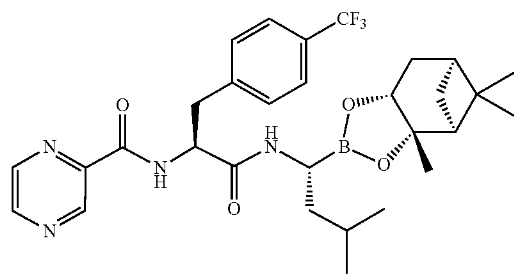 [SMILES: CC(C)C[C@H](NC(=O)[C@H](Cc1ccc(C(F)(F)F)cc1)NC(=O)c1cnccn1)B1O[C@@H]2C[C@@H]3C[C@@H](C3(C)C)[C@]2(C)O1] | (S)-N-(pyrazinylformyl)-3-(4-trifluoromethyl phenyl)propionamido-D-leucine borate-(+)-α-pinanediol ester<br>Yield 82.79%. $^1$H NMR (400 MHz, CDCl$_3$) δ 0.80 (—CH$_3$, s, 3H), 0.83 (—CH$_3$, s, 6H), 1.17 (—CH, dd, J$_1$ = 10.9 Hz, J$_2$ = 17.6 Hz, 1H), 1.24 (—CH$_2$, s, 2H), 1.27 (—CH$_3$, s, 3H), 1.38 (—CH$_3$, s, 3H), 1.75 (—CH, s, 1H), 1.86 (—CH$_2$, ddd, J$_1$ = 2.8 Hz, J$_2$ = 5.8 Hz, J$_3$ = 11.1 Hz, 1H), 1.90-1.96 (—CH$_2$, m, 1H), 2.01 (—CH, dd, J$_1$ = 1.5 Hz, J$_2$ = 12.7 Hz, 1H), 2.15 (—CH$_2$, ddd, J$_1$ = 5.2 Hz, J$_2$ = 10.0 Hz, J$_3$ = 10.9 Hz, 1H), 2.25-2.37 (—CH$_2$, m, 1H), 3.15-3.23 (—CH$_2$, m, 2H), 3.23-3.27 (—CH, m, 1H), 4.27 (—CH, ddd, J$_1$ = 1.8 Hz, J$_2$ = 8.7 Hz, J$_3$ = 15.0 Hz, 1H), 4.77-4.91 (—CH, m, 1H), 6.03 (—CONH, dd, J$_1$ = 5.7 Hz, J$_2$ = 11.5 Hz, 1H), 7.40 (—Ph, d, J = 8.0 Hz, 2H), 7.52 (—Ph, t, 7.3 Hz, 2H), 8.40 (—CONH, dd, J$_1$ = 4.5 Hz, J$_2$ = 8.2 Hz, 1H), 8.50-8.57 (—Pyz, m, 1H), 8.76 (—Pyz, d, J = 2.3 Hz, 1H), 9.29-9.36 (—Pyz, m, 1H). MS (ESI): m/z 587.4 [M + H]$^+$. |
| I-3k | 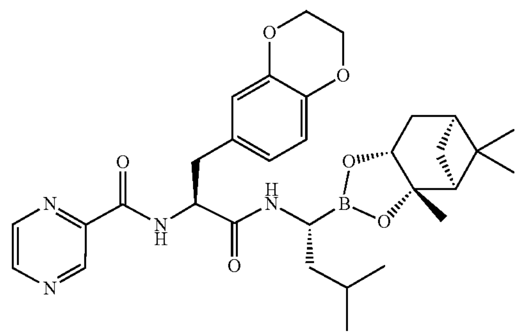 [SMILES: CC(C)C[C@H](NC(=O)[C@H](Cc1ccc2c(c1)OCCO2)NC(=O)c1cnccn1)B1O[C@@H]2C[C@@H]3C[C@@H](C3(C)C)[C@]2(C)O1] | (S)-N-(pyrazinylformyl)-3-(2,3-dihydro-1,4-benzodioxol-6-yl)propionamido-D-leucine borate-(+)-α-pinanediol ester<br>Yield 84.7%. $^1$H NMR (400 MHz, CDCl$_3$) δ 0.82 (s, 3H). 0.85 (s, 6H), 0.93 (—CH, s, 1H), 1.22 (—CH$_2$, d, J = 10.8 Hz, 1H), 1.28 (—CH$_3$, s, 3H), 1.40 (—CH$_3$, s, 3H), 1.46 (—CH$_2$, dd, J$_1$ = 6.8 Hz, J$_2$ = 13.2 Hz, 1H), 1.66 (—CH, s, 1H), 1.79-1.93 (—CH$_2$, m, 2H), 2.02 (—CH, dd, J$_1$ = 7.3 Hz, J$_2$ = 12.6 Hz, 1H), 2.14-2.23 (—CH$_2$, m, 1H), 2.27-2.38 (—CH$_2$, m, 1H), 2.96-3.07 (—CH, m, 1H), 3.07-3.26 (—CH$_2$, m, 2H), 4.21 (—CH$_2$, s, 4H), 4.24-4.37 (—CH, m, 1H), 4.74 (—CH, dd, J$_1$ = 7.8 Hz, J$_2$ = 14.3 Hz, 1H), 5.90 (—CONH, dd, J$_1$ = 5.1 Hz, J$_2$ = 39.8 Hz, 1H), 6.71-6.85 (—Ph, m, 3H), 8.38 (—CONH, dd, J$_1$ = 8.3 Hz, J$_2$ = 14.3 Hz, 1H), 8.54 (—Pyz, d, J = 5.1 Hz, 1H), 8.74 (—Pyz, d, J = 2.2 Hz, 1H), 9.35 (—Pyz, s, 1H). MS (ESI): m/z 575.3 [M − H]$^−$. |

| No. | Structure | Chemical name and analytical data |
|---|---|---|
| I-3l | 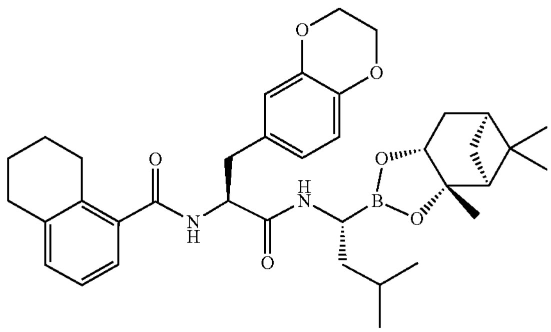 [SMILES: CC(C)C[C@H](NC(=O)[C@H](Cc1ccc2c(c1)OCCO2)NC(=O)c1cccc2c1CCCC2)B1O[C@@H]2C[C@@H]3C[C@@H](C3(C)C)[C@]2(C)O1] | (S)-N-(5,6,7,8-tetrahydro-1-naphthoyl)-3-(2,3-dihydro-1,4-benzodioxol-6-yl)propionamido-D-leucine borate-(+)-α-pinanediol ester<br>Yield 85.5%. $^1$H NMR (400 MHz, CDCl$_3$) δ 0.84 (—CH$_3$, s, 3H), 0.89 (—CH$_3$, s, 6H), 1.25 (—CH$_2$, d, J = 2.6 Hz, 1H), 1.27 (—CH$_3$, s, 3H), 1.34 (—CH$_2$, dt, J$_1$ = 4.6 Hz, J$_2$ = 11.2 Hz, 1H), 1.43 (—CH$_3$, s, 3H), 1.52 (—CH, dt, J$_1$ = 1.3 Hz, J$_2$ = 13.6 Hz, 1H), 1.59-1.67 (—CH, m, 1H), 1.74 (—CH$_2$, s, 4H), 1.80-1.96 (—CH$_2$, m, 2H), 1.98-2.06 (—CH, m, 1H), 2.12-2.25 (—CH$_2$, m, 1H), 2.26-2.38 (—CH$_2$, m, 1H), 2.72 (—CH$_2$, ddd, J$_1$ = 7.3 Hz, J$_2$ = 13.8 Hz, J$_3$ = 24.1 Hz, 4H), 2.93-3.11 (—CH$_2$, m, 2H), 3.14-3.23 (—CH, m, 1H), 4.22 (—CH$_2$, s, 4H), 4.30 (—CH, ddd, J$_1$ = 4.6 Hz, J$_2$ = 9.1 Hz, J$_3$ = 16.2 Hz, 1H), 4.66-4.83 (—CH, m, 1H), 6.12 (—CONH, dd, J$_1$ = 5.3 Hz, J$_2$ = 49.1 Hz, 1H), 6.27-6.42 (—CONH, m, 1H), 6.70-6.76 (—Ph, m, 1H), 6.76-6.83 (—Ph, m, 2H), 6.99-7.14 (—Ph, m, 3H). MS (ESI): m/z 627.3 [M − H]$^-$. |
| I-3m | 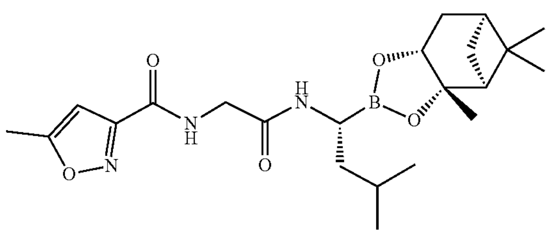 | N-(5-methylisoxazol-3-formyl)acetamido-D-leucine borate-(+)-α-pinanediol ester<br>Yield 57.9%. $^1$H NMR (400 MHz, CDCl$_3$) δ 0.83 (—CH$_3$, s, 3H), 0.89 (—CH$_3$, s, 3H), 0.91 (—CH$_3$, s, 3H), 1.27 (—CH$_3$, s, 3H), 1.39 (—CH$_3$, s, 3H), 1.46 (—CH$_2$, dd, J$_1$ = 6.9 Hz, J$_2$ = 13.8 Hz, 2H), 1.63 (—CH, dp, J$_1$ = 6.1 Hz, J$_2$ =13.3 Hz, 1H), 1.75-1.86 (—CH$_2$, m, 2H), 1.87-1.93 (—CH, m, 1H), 1.99-2.05 (—CH, m, 1H), 2.18 (—CH$_2$, ddd, J$_1$ = 4.4 Hz, J$_2$ = 6.2 Hz, J$_3$ = 10.7 Hz, 1H), 2.27-2.36 (—CH$_2$, m, 1H), 2.47 (—CH$_3$, s, 3H), 3.28 (—CH, dd, J$_1$ = 12 Hz, J$_2$ = 13.4 Hz, 1H), 4.10 (—CH$_2$, d, J = 5.5 Hz, 2H), 4.30 (—CH, dd, J$_1$ = 1.7 Hz, J$_2$ = 8.8 Hz, 1H), 6.20 (—CH, d, J = 4.8 Hz, 1H), 6.42 (—CONH, s, 1H), 7.46 (—CONH, s, 1H). MS (ESI): m/z 432.3 [M + H]$^+$. |
| I-3n | 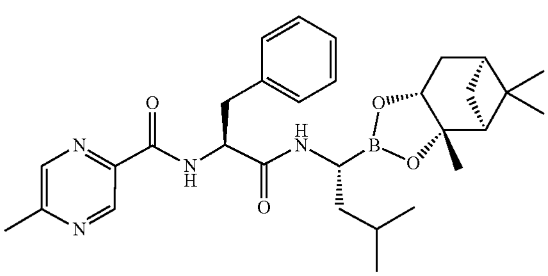 | (S)-N-(5-methyl-2-pyrazinylformyl)phenylpropionamido-D-leucine borate-(+)-α-pinanediol ester<br>Yield 79.1%. $^1$H NMR (400 MHz, CDCl$_3$) δ 0.82 (—CH$_3$, s, 3H), 0.84 (—CH$_3$, s, 6H), 1.28 (—CH$_3$, s, 3H), 1.34 (—CH$_2$, d, 4.9 Hz, 2H), 1.39 (—CH$_3$, s, 3H), 1.41-1.46 (—CH, m, 1H), 1.87 (—CH$_2$, d, J = 20.0 Hz, 2H), 1.96-2.08 (—CH$_2$, m, 2H), 2.18 (—CH, d, J = 10.7 Hz, 1H), 2.28-2.37 (—CH, m, 1H), 2.64 (—CH$_3$, s, 3H), 3.10-3.19 (—CH$_2$, m, 2H), 3.19-3.27 (—CH, m, 1H), 4.30 (—CH, d, J = 8.8 Hz, 1H), 4.79 (—CH, dd, J$_1$ = 7.0 Hz, J$_2$ = 14.4 Hz, 1H), 5.89 (—CONH, dd, J$_1$ = 4.6 Hz, J$_2$ = 62.7 Hz, 1H), 7.22 (—Ph, d, J = 4.3 Hz, 1H), 7.28 (—Ph, d, J = 3.8 Hz, 4H), 8.24-8.35 (—CONH, m, 1H), 8.37 (—Pyz, s, 1H), 9.20 (—Pyz, s, 1H). MS (ESI): m/z 533.3 [M + H]$^+$. |
| I-3o | 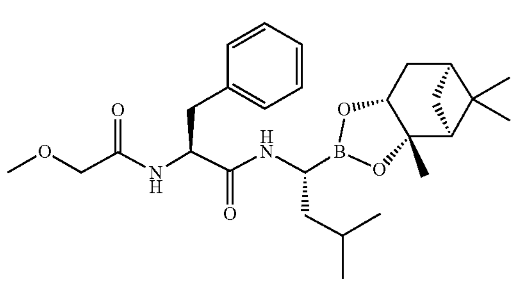 | (S)-N-(methoxyacetyl)phenylpropionamido-D-leucine borate-(+)-α-pinanediol ester<br>Yield 83.8%. $^1$H NMR (400 MHz, CDCl$_3$) δ 0.82 (—CH$_3$, s, 3H), 0.84 (—CH$_3$, d, 3.1 Hz, 6H), 1.28 (—CH$_3$, s, 3H), 1.34 (—CH$_2$, d, 9.4 Hz, 2H), 1.40 (—CH$_3$, s, 3H), 1.74 (—CH$_2$, s, 2H), 1.81 (—CH, s, 1H), 1.89 (—CH, s, 1H), 2.02 (—CH, t, J = 5.2 Hz, 1H), 2.12-2.21 (—CH$_2$, m, 1H), 2.27-2.36 (—CH$_2$, m, 1H), 3.07 (—CH$_2$, —CH, d, J = 7.1 Hz, 3H), 3.32 (—CH$_3$, s, 3H), 3.84 (—CH$_2$, s, 2H), 4.29 (—CH, d, J = 8.6 Hz, 1H), 4.64 (—CH, q, J = |

| No. | Structure | Chemical name and analytical data |
|---|---|---|
| | | 7.5 Hz, 1H), 6.02 (—CONH, d, J = 3.7 Hz, 1H), 7.07 (—CONH, d, J = 8.0 Hz, 1H), 7.23 (—Ph, d, J = 6.7 Hz, 2H), 7.25-7.30 (—Ph, m, 3H). MS (ESI): m/z 485.43 [M + H]⁺. |
| I-3p | 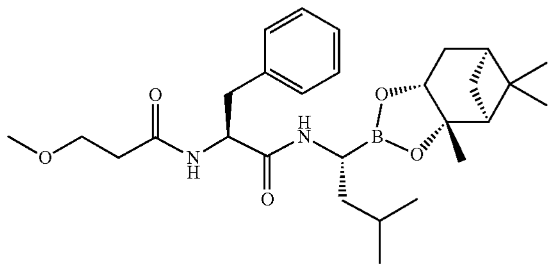 | (S)-N-(3-methoxypropionyl) phenylpropionamido-D-leucine borate-(+)-α-pinanediol ester Yield 85.7%. ¹H NMR (400 MHz, CDCl₃) 50.84 (—CH₃, s, 3H), 0.86 (—CH₃, d, J = 6.1 Hz, 6H), 1.28 (—CH₃, s, 3H), 1.33-1.38 (—CH₂, m, 2H), 1.41 (—CH₃, s, 3H), 1.47 (—CH, dd, J₁ = 6.6 Hz, J₂ = 13.2 Hz, 1H), 1.79-1.96 (—CH₂, —CH, m, 3H), 2.03 (—CH, t, J = 5.5 Hz, 1H), 2.15-2.23 (—CH₂, m, 1H), 2.29-2.37 (—CH₂, m, 1H), 2.41 (—CH₂, dd, J₁ =3.5 Hz, J₂ = 8.2 Hz, 2H), 3.03 (—CH, d, J = 6.9 Hz, 1H), 3.10 (—CH₂, td, J₁ = 6.1 Hz, J₂ = 14.0 Hz, 2H), 3.28 (—CH₃, s, 3H), 3.46-3.61 (—CH₂, m, 2H), 4.26-4.33 (—CH, m, 1H), 4.68 (—CH, dd, J₁ = 1.1 Hz, J₂ = 14.6 Hz, 1H), 6.20 (—CONH, s, 1H), 6.65 (—CONH, d, ) = 7.9 Hz, 1H), 7.20-7.25 (—Ph, m, 3H), 7.29 (—Ph, t, 6.3 Hz, 2H). MS (ESI): m/z 499.46 [M + H]⁺. |
| I-3q | 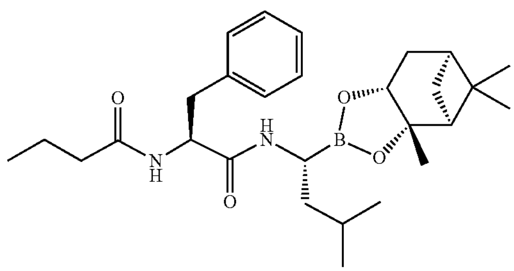 [SMILES: CCCC(=O)N[C@@H](Cc1ccccc1)C(=O)N[C@@H](CC(C)C)B1O[C@@H]2C[C@@H]3C[C@@H](C3(C)C)[C@]2(C)O1] | (S)-N-(butanoyl)phenylpropionamido-D-leucine borate-(+)-α-pinanediol ester Yield 75.9%. ¹H NMR (400 MHz, CDCl₃) δ 0.82 (—CH₃, s, 3H), 0.84 (—CH₃, s, 6H), 0.88 (—CH₃, d, J = 5.7 Hz, 3H), 1.28 (—CH₃, s, 3H), 1.34 (—CH₂, d, 7.7 Hz, 2H), 1.40 (—CH₃, s, 3H), 1.42-1.47 (—CH, m, 1H), 1.58-1.63 (—CH₂, m, 2H), 1.70 (—CH, s, 1H), 1.78-1.93 (—CH₂, m, 2H), 2.02 (—CH, t, J = 5.5 Hz, 1H), 2.12 (—CH₂, t, J = 7.6 Hz, 2H), 2.15-2.19 (—CH₂, m, 1H), 2.26-2.38 (—CH₂, m, 1H), 2.97-3.04 (—CH, m, 1H), 3.09-3.20 (—CH₂, m, 2H), 4.28 (—CH, d, J = 8.4 Hz, 1H), 4.61-4.67 (—CH, m, 1H), 5.99 (—CONH, s, 1H), 6.17 (—CONH, d, J = 7.8 Hz, 1H), 7.23 (—Ph, d, J = 7.4 Hz, 3H), 7.26-7.31 (—Ph, m, 2H). MS (ESI): m/z 483.42 [M + H]⁺. |
| I-3r | 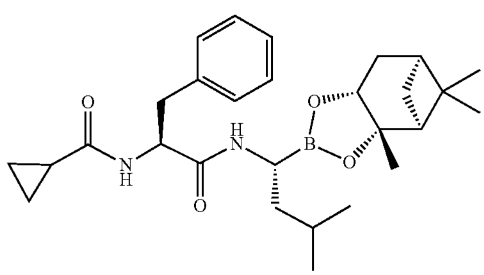 [SMILES: CC(C)C[C@H](NC(=O)[C@H](Cc1ccccc1)NC(=O)C1CC1)B1O[C@@H]2C[C@@H]3C[C@@H](C3(C)C)[C@]2(C)O1] | (S)-N-(cyclopropylformyl) phenylpropionamido-D-leucine borate-(+)-α-pinanediol ester Yield 82.4%. ¹H NMR (400 MHz, CDCl₃) δ 0.70-0.76 (—CH₂, m, 2H), 0.84 (—CH₃, dd, J₁ = 4.3 Hz, J₂ = 6.8 Hz, 9H), 0.90-0.96 (—CH₂, m, 2H), 1.20 (—CH, d = 10.8 Hz, 1H), 1.28 (—CH₃, s, 3H), 1.34 (—CH₂, d, J = 6.9 Hz, 2H), 1.40 (—CH₃, s, 3H), 1.66 (—CH, s, 1H), 1.82 (—CH₂, d, 14.5 Hz, 1H), 1.86-1.95 (—CH₂, m, 1H), 2.02 (—CH, t, J = 5.5 Hz, 1H), 2.18 (—CH₂, m, 1H), 2.26-2.37 (—CH₂, m, 1H), 3.00 (—CH₂, -d, 8.0 Hz, 1H), 3.11 (—CH₂, td, J₁ = 6.5 Hz, J₂ = 13.5 Hz, 2H), 4.25 (—CH, d, J = 8.3 Hz, 1H), 4.60 (—CH, dd, J₁ = 7.8 Hz, J₂ = 13.8 Hz, 1H), 5.97 (—CONH, s, 1H), 6.40 (—CONH, s, 1H), 7.20-7.26 (—Ph, m, 3H), 7.28 (—Ph, d, 7.8 Hz, 2H) MS (ESI): m/z 481.2 [M + H]⁺. |
| I-3s | 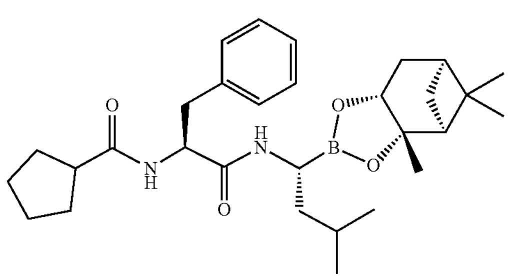 [SMILES: CC(C)C[C@H](NC(=O)[C@H](Cc1ccccc1)NC(=O)C1CCCC1)B1O[C@@H]2C[C@@H]3C[C@@H](C3(C)C)[C@]2(C)O1] | (S)-N-(cyclopentylformyl) phenylpropionamido-D-leucine borate-(+)-α-pinanediol ester Yield 84.9%. ¹H NMR (400 MHz, CDCl₃) δ 0.84 (—CH₃, t, J = 5.7 Hz, 9H), 1.18-1.23 (—CH, m, 1H), 1.28 (—CH₃, s, 3H), 1.34 (—CH₂, t, J = 7.2 Hz, 2H), 1.39 (—CH₃, s, 3H), 1.49-1.58 (—CH₂, m, 2H), 1.61-1.73 (—CH₂, —CH₂, m, 4H), 1.74-1.80 (—CH₂, m, 2H), 1.80-1.84 (—CH, m, 1H), 1.86-1.94 (—CH₂, m, 2H), 2.01 (—CH, dd, J₁ = 4.5 Hz, J₂ =10.2 Hz, 1H), 2.17 (—CH₂, m, 1H), 2.25-2.36 (—CH₂, m, 1H), 2.42-2.55 (—CH, m, |

| No. | Structure | Chemical name and analytical data |
|---|---|---|
| | | 1H), 3.01 (—CH$_2$, dd, J$_1$ = 1.6 Hz, J$_2$ =13.7 Hz, 1H), 3.09 (—CH$_2$, —CH, dd, J, = 6.3 Hz, J$_2$ = 13.7 Hz, 2H), 4.24 (—CH, d, J = 8.0 Hz, 1H), 4.62 (—CH, d, J = 7.5 Hz, 1H), 6.18 (—CONH, s, 1H), 6.28 (—CONH, s, 1H), 7.18-7.26 (—Ph, m, 4H), 7.26-7.30 (—Ph, m, 1H). MS (ESI): m/z 509.38 [M + H]$^+$. |

4. Production of (S)—N-(2,5-dichlorobenzoyl)-3-(4-trifluoromethyl phenyl)propionamido-D-leucine Boric Acid (IV-1)

Compound I-3a (317 mg, 0.49 mmol) was dissolved in MeOH (3 mL), and then isobutylboric acid (247 mg, 2.43 mmol), n-hexane (3 mL) and 1 N HCl (1.2 mL, 1.2 mmol) were added in sequence and reacted overnight with stirring until the reaction was completed as indicated by TLC. The n-hexane phase was extracted twice with methanol (2×3 mL), and the methanol phase was washed once with n-hexane (3 mL). Methanol is removed by evaporation under reduced pressure, and the aqueous phase was extracted twice with CH$_2$Cl$_2$ (2×2 mL). The organic phase was washed with saturated brine (3×5 mL) until the aqueous phase was neutral. The solvent was evaporated off under reduced pressure, and the residue was separated by column chromatography to obtain a product (193 mg, yield 76.5%). $^1$H NMR (400 MHz, CDCl$_3$) δ 1.18 (—CH$_3$, s, 3H), 1.25 (—CH$_3$, s, 3H), 2.13-2.41 (—CH$_2$, m, 2H), 2.45-2.61 (—CH, m, 1H), 3.20-3.58 (—CH$_2$, m, 2H), 3.58-3.71 (—CH, m, 1H), 5.21-5.62 (—CH, m, 1H), 7.62-7.75 (-Ph, m, 4H), 7.84 (-Ph, t, J=13.5 Hz, 3H). $^{13}$C NMR (CDCl$_3$, 100 MHz) δ 22.67, 27.21, 31.90, 35.60, 51.28, 54.80, 125.37, 125.55, 128.92, 129.05, 129.47, 129.76, 129.85, 131.34, 131.60, 133.12, 133.17, 139.92, 165.18, 170.98. MS (ESI): m/z 517.1 [M−H], calcd: 518.1. HRMS(ESI): calcd for C$_{22}$H$_{24}$BCl$_2$F$_3$N$_2$NaO$_4$ [M+Na]$^+$ 541.1054, found 541.1118.

Other boric compounds of the present invention can be synthesized through the above methods.

Specific compounds are shown in a Table below.

| No. | Structure | Chemical name and analytical data |
|---|---|---|
| IV-2 | 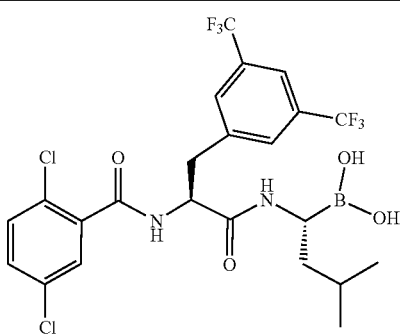 | (S)-N-(2,5-dichlorobenzoyl)-3-(3,5-bis(trifluoromethyl)phenyl)propionamido-D-leucine boric acid<br>Yield 41.4%. $^1$H NMR (400 MHz, CDCl$_3$) δ 0.81 (—CH$_3$, s, 3H) 0.86 (—CH$_3$, s, 3H), 1.29-1.50 (—CH$_2$, m, 2H), 1.50-1.74 (—CH, m, 1H), 3.04-3.33 (—CH$_2$, m, 2H) 3.34-3.44 (—CH, m 1H), 4.86-5.24 —CH, m, 1H), 7.20-7.25 (—Ph, m, 1H), 7.30 (—Ph, ddd, J$_1$ = 3.6 Hz, J$_2$ = 7.4 Hz, J$_3$ = 11.7 Hz, 2H), 7.73 (—Ph, d, J =13.0 Hz, 2H), 7.77 (—Ph, s, 1H). $^{13}$C NMR (CDCl$_3$, 100 MHz) δ 22.78, 25.76, 37.33, 39.62, 52.41, 53.60, 119.06, 121.77, 124.49, 129.36, 129.64, 131.30, 131.68, 132.00, 133.14, 133.24, 134.95, 135.32, 138.65, 165.83, 172.26. MS (ESI): m/z 585.2 [M − H]$^-$.<br>HRMS (ESI): calcd for C$_{23}$H$_{23}$BCl$_2$F$_6$N$_2$NaO$_4$ [M + Na]$^+$ 609.0928, found 609.0985. |
| IV-3 | 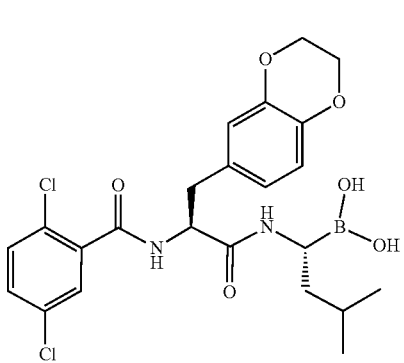 [SMILES: CC(C)C[C@H](NC(=O)[C@H](Cc1ccc2c(c1)OCCO2)NC(=O)c1cc(Cl)ccc1Cl)B(O)O] | (S)-N-(2,5-dichlorobenzoyl)-3-(2,3-dihydro-1,4-benzodioxol-6-yl)propionamido-D-leucine boric acid<br>Yield 59.2%. $^1$H NMR (400 MHz, CDCl$_3$) δ 0.84 (—CH$_3$, m, 3H), 0.87 (—CH$_3$, m, 3H), 1.29 (—CH, dd, J$_1$ = 8.8 Hz, J$_2$ = 15.0 Hz, 1H), 1.39-1.56 (—CH$_2$, m, 2H), 2.92 (—CH, d, 35.0 Hz, 1H), 3.09 (—CH$_2$, t, J = 6.2 Hz, 2H), 4.21 (—CH$_2$, d, J = 5.5 Hz, 4H), 4.91 (—CH, t, J = 19.8 Hz, 1H), 6.66 (—Ph, dt, J$_1$ = 12.5 Hz, J$_2$ = 27.4 Hz, 1H), 6.71-6.80 (—Ph, m, 2H), 7.21-7.59 (—Ph, m, 3H). $^{13}$C NMR (CDCl$_3$, 100 MHz) δ 22.98, 25.82, 37.32, 39.90, 50.52, 52.82, 64.25, 117.35, 118.30, 122.46, 128.74, 129.09, 129.48, 131.25, 132.94, 135.75, 142.68, 143.36, 165.24, 172.64. MS (ESI): m/z 507.2 [M − H]$^-$. HRMS (ESI): calcd for C$_{23}$H$_{27}$BCl$_2$N$_4$NaO$_6$ [M + Na]$^+$ 531.1325, found 531.1246. |

-continued

| No. | Structure | Chemical name and analytical data |
|---|---|---|
| IV-4 | 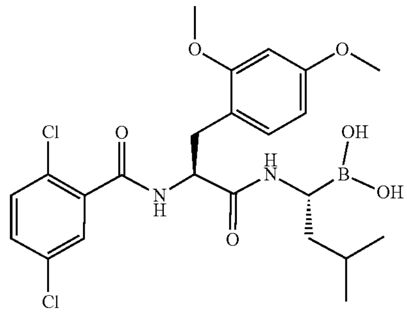 [SMILES: COc1ccc(C[C@H](NC(=O)c2cc(Cl)ccc2Cl)C(=O)N[C@@H](CC(C)C)B(O)O)c(OC)c1] | (S)-N-(2,5-dichlorobenzoyl)-3-(2,4-dimethoxy phenyl)propionamido-D-leucine boric acid<br>Yield 62.3%. $^1$H NMR (400 MHz, CDCl$_3$) δ 0.86 (—CH$_3$, s, 3H), 0.87 (—CH$_3$, s, 3H), 1.35 (—CH, dd, $J_1$ = 6.1 Hz, $J_2$ = 11.5 Hz, 1H), 1.43-1.62 (—CH$_2$, m, 2H), 2.92-3.11 (—CH, m, 1H), 3.10-3.26 (—CH$_2$, m, 2H), 3.74 (—CH$_3$, s, 3H), 3.79 (—CH$_3$, s, 3H), 4.90 (—CH, t, J = 18.1 Hz, 1H), 6.40-6.51 (—Ph, m, 2H), 7.10 (—Ph, d, J = 7.7 Hz, 2H), 7.17-7.23 (—Ph, m, 1H), 7.2.5 (—Ph, d, J = 2.7 Hz, 1H), 7.27 (—CONH, d, J = 6.2 Hz, 1H), 7.38 (—CONH, dd, $J_1$ = 9.2 Hz, $J_2$ = 42.9 Hz, 1H). $^{13}$C NMR (CDCl$_3$, 100 MHz) δ 23.03, 25.84, 29.63, 31.49, 50.52, 52.64, 55.30, 98.58, 104.50, 116.76, 129.08, 129.11, 129.31, 131.20, 132.05, 132.84, 136.01, 158.23, 360.22, 165.46, 173.4. MS (ESI): m/z 509.2 [M − H]$^-$. HRMS (ESI): calcd for C$_{23}$H$_{29}$BCl$_2$N$_4$NaO$_6$ [M + Na]$^+$ 533.1392, found 533.1403. |
| IV-5 | 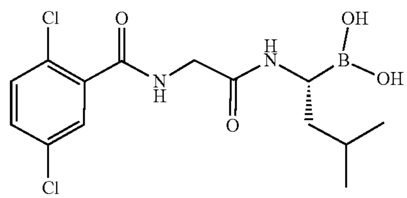 [SMILES: CC(C)C[C@H](NC(=O)CNC(=O)c1cc(Cl)ccc1Cl)B(O)O] | N-(2,5-dichlorobenzoyl)acetamido-D-leucine boric acid<br>Yield 62.4%. $^1$H NMR (400 MHz, DMSO) δ 0.82 (—CH$_3$, s, 3H), 0.84 (—CH$_3$, s, 3H), 1.19-1.28 (—CH$_2$, m, 2H), 1.61 (—CH, td, $J_1$ = 6.6 Hz, $J_2$ = 13.2 Hz, 1H), 2.66 (—CH, s, 1H), 4.04 (—CH$_2$, d, J = 5.6 Hz, 2H), 7.55 (—Ph, d, J = 1.3 Hz, 2H), 7.66 (—Ph, s, 1H), 8.82 (—CONH, d, J = 46.3 Hz, 1H), 8.99 (—CONH, t, J = 5.7 Hz, 1H). $^{13}$C NMR (CDCl$_3$, 100 MHz) δ 22.91, 25.94, 39.90, 44.28, 60.37, 129.20, 129.45, 131.25, 131.34, 132.97, 135.53, 166.38, 171.16. MS (ESI): m/z 359.2 [M − H]$^-$. HRMS (ESI): calcd for C$_{14}$H$_{19}$BCl$_2$N$_2$NaO$_4$ [M + Na]$^+$ 383.0710, found 383.0727. |
| IV-6 | 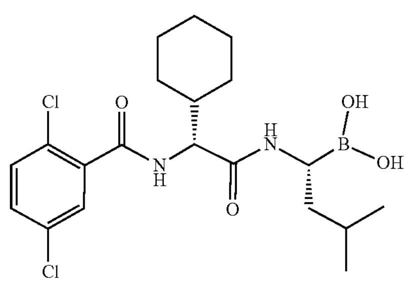 [SMILES: CC(C)C[C@H](NC(=O)[C@H](NC(=O)c1cc(Cl)ccc1Cl)C1CCCCC1)B(O)O] | (R)-N-(2,5-dichlorobenzoyl)-2-cyclohexylacetamido-D-leucine boric acid<br>Yield 68.5%. $^1$H NMR (400 MHz, CDCl$_3$) δ 0.80 (—CH$_3$, s, 3H), 0.86 (—CH$_3$, s, 3H), 1.13-1.29 (—CH$_2$, m, 5H), 1.29-1.45 (—CH$_2$, m, 2H), 1.53 (—CH, ddd, $J_1$ = 6.9 Hz, $J_2$ = 13.7 Hz, $J_3$ = 21.6 Hz, 1H), 1.68 (—CH, s, 1H), 1.83 (—CH$_2$, dd, $J_1$ = 23.0 Hz, $J_2$ = 26.6 Hz, 5H), 3.09 (—CH, d, J = 109.8 Hz, 1H), 4.65 (—CH, ddd, $J_1$ = 15.0 Hz, $J_2$ = 22.8 Hz, $J_3$ = 35.2 Hz, 1H), 7.28-7.88 (—Ph, m, 3H). $^{13}$C NMR (CDCl$_3$, 100 MHz) δ 23.08, 25.65, 25.77, 26.09, 29.65, 39.86, 39.92, 57.29, 57.37, 129.17, 129.77, 131.17, 132.91, 136.00, 165.32, 172.40. MS (ESI): m/z 441.3 [M − H]$^-$. HRMS (ESI): calcd for C$_{20}$H$_{29}$BCl$_2$N$_2$NaO$_4$ [M + Na]$^+$ 465.1493, found 465.1495. |
| IV-7 | 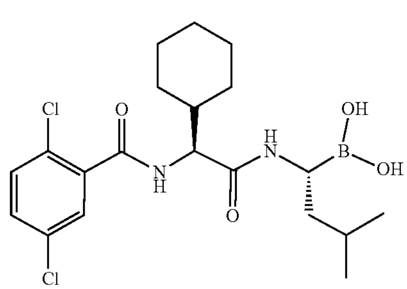 [SMILES: CC(C)C[C@H](NC(=O)[C@@H](NC(=O)c1cc(Cl)ccc1Cl)C1CCCCC1)B(O)O] | (S)-N-(2,5-dichlorobenzoyl)-2-cyclohexylacetamido-D-leucine boric acid<br>Yield 71.4%. $^1$H NMR (400 MHz, CDCl$_3$) δ 0.77 (—CH$_3$, s, 3H), 0.88 (—CH$_3$, s, 3H), 1.01-1.27 (—CH$_2$, m, 5H), 1.31-1.51 (—CH$_2$, m, 2H), 1.52-1.62 (CH, m, 1H), 1.67 (—CH, d, 11.3 Hz, 1H), 1.75 (—CH$_2$, s, 5H), 2.80-3.09 (—CH, m, 1H), 4.39-4.75 (—CH, m, 1H), 7.29-7.43 (—Ph, m, 2H), 7.50-7.62 (—Ph, m, 1H). $^{13}$C NMR (CDCl$_3$, 100 MHz) δ 23.05, 25.83, 28.85, 29.35, 29.64, 39.98, 40.62, 56.60, 58.10, 129.02, 129.62, 131.34, 133.10, 135.82, 135.98, 165.34, 172.59. MS (ESI): m/z 441.2 [M − H]$^-$. HRMS (ESI): calcd for C$_{20}$H$_{29}$BCl$_2$N$_2$NaO$_4$ [M + Na]$^+$ 465.1493, found 465.1497. |

| No. | Structure | Chemical name and analytical data |
| --- | --- | --- |
| IV-8 | 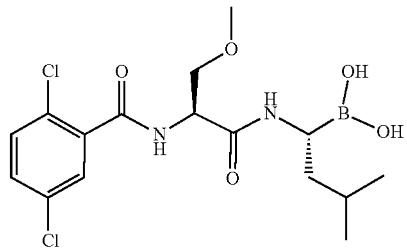 [SMILES: COC[C@H](NC(=O)c1cc(Cl)ccc1Cl)C(=O)N[C@@H](CC(C)C)B(O)O] | (S)-N-(2,5-dichlorobenzoyl)-3-methoxypropionamido-D-leucine boric acid<br>Yield 69.8%. $^1$H NMR (400 MHz, CDCl$_3$) δ 0.87 (—CH$_3$, s, 3H), 0.93 (—CH$_3$, s, 3H), 1.30-1.54 (—CH$_2$, m, 2H), 1.54-1.67 (—CH, m, 1H), 3.40 (—CH$_3$, s, 3H), 3.51-3.65 (—CH$_2$, m, 2H), 3.90 (—CH, qd, J$_1$ = 5.1 Hz, J$_2$ = 9.3 Hz, 1H), 4.62-4.93 (—CH, m, 1H), 7.29-7.37 (—Ph, m, 2H), 7.56-7.65 (—Ph, m, 1H), $^{13}$C NMR (CDCl$_3$, 100 MHz) δ 22.87, 25.79, 39.73, 53.20, 59.05, 59.12, 71.15, 129.03, 129.77, 131.32, 133.07, 135.55, 165.34, 172.18. MS (ESI): m/z 403.0 [M − H]$^−$. HRMS (ESI): calcd for C$_{16}$H$_{23}$BCl$_2$N$_2$NaO$_5$ [M + Na]$^+$ 427.0972, found 427.0974. |
| IV-9 | 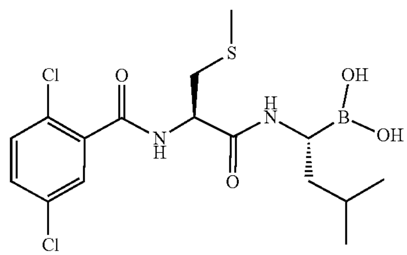 [SMILES: CSC[C@H](NC(=O)c1cc(Cl)ccc1Cl)C(=O)N[C@@H](CC(C)C)B(O)O] | (R)-N-(2,5-dichlorobenzoyl)-3-methylmercaptopropionamido-D-leucine boric acid<br>Yield 52.4%. $^1$H NMR (400 MHz, CDCl$_3$) 5 0.87 (—CH$_3$, s, 6H), 1.42 (—CH$_2$, ddd, J, = 6.4 Hz, J$_2$ = 12.8 Hz, J$_3$ = 13.3 Hz, 2H), 1.59 (—CH, dd, J$_1$ = 6.4 Hz, J$_2$ = 13.2 Hz, 1H), 2.18 (CH$_3$, s, 3H), 2.87-3.02 (—CH$_2$, m, 2H), 3.02-3.11 (—CH, m, 1H), 4.82-5.02 (—CH m, 1H), 7.32 (—PH, t, J = 5.9 Hz, 2H), 7.35-7.41 (—CONH, m, 1H), 7.42-7.54 (—CONH, m, 1H), 7.58 (—Ph, s, 1H). $^{13}$C NMR (CDCl$_3$, 100 MHz) δ 15.87, 22.94, 25.83, 29.60, 39.73, 50.90, 51.22, 129.09, 129.63, 1.31.35, 133.07, 135.41, 165.40, 171.84. MS (ESI): m/z 419.2 [M − H]$^−$. HRMS (ESI): calcd for C$_{16}$H$_{23}$BCl$_2$N$_2$NaO$_4$S [M + Na]$^+$ 443.0754, found 443.0744. |
| IV-10 | 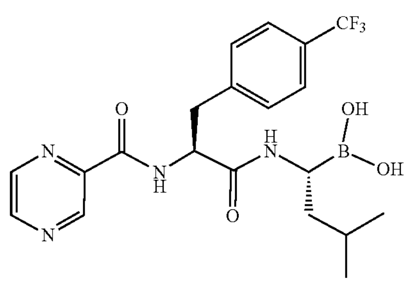 [SMILES: CC(C)C[C@H](NC(=O)[C@H](Cc1ccc(C(F)(F)F)cc1)NC(=O)c1cnccn1)B(O)O] | (S)-N-(pyrazinylformyl)-3-(4-trifluoromethyl phenyl)propionamido-D-leucine boric acid<br>Yield 73.3%. $^1$H NMR (400 MHz, CDCl$_3$) δ 0.69 (—CH$_3$, s, 3H), 0.83 (—CH$_3$, s, 3H), 1.26 (—CH$_2$, d, J = 11.4 Hz, 2H), 1.39 (—CH, dt, J$_1$ = 6.3 Hz, J$_2$ = 13.0 Hz, 1H), 2.93 (—CH, dd, J$_1$ = 77.8 Hz, J$_2$ = 115.9 Hz, 1H), 3.18-3.41 (—CH$_2$, m, 2H), 4.79-5.30 (—CH, m, 1H), 6.31-7.24 (—CONH, m, 1H), 7.40 (—Ph, dd, J$_1$ = 7.7 Hz, J$_2$ = 25.1 Hz, 2H), 7.52 (—Ph, d, 8.1 Hz, 2H), 8.16-8.40 (—Pyz, m, 1H), 8 41-8.57 (—Pyz, m, 1H), 8.66-8.81 (—Pyz, m, 1H), 9.10-9.36 (—CONH, m, 1H). $^{13}$C NMR (CDCl$_3$, 100 MHz) δ 22.7, 25.71, 37.89, 39.82, 52.12, 54.32, 125.31, 125.48, 129.63, 129.80, 139.80, 142.73, 144.17, 163.09, 172.24. MS (ESI): m/z 451.1 [M − H]$^−$. HRMS (ESI): calcd for C$_{20}$H$_{24}$BF$_3$N$_4$NaO$_4$ [M + Na]$^+$ 475.1738, found 475.1740. |
| IV-11 | 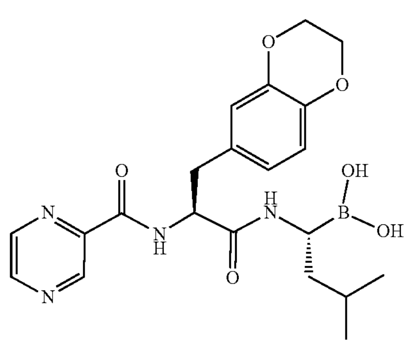 [SMILES: CC(C)C[C@H](NC(=O)[C@H](Cc1ccc2c(c1)OCCO2)NC(=O)c1cnccn1)B(O)O] | (S)-N-(pyrazinylformyl)-3-(2,3-dihydro-1,4-benzodioxol-6-yl)propionamido-D-leucine boric acid<br>Yield 74.7%. $^1$H NMR (400 MHz, DMSO) δ 0.74 (—CH$_3$, s, 3H), 0.84 (—CH$_3$, s, 3H), 1.02-1.21 (—CH$_2$, m, 1H), 1.35 (—CH$_2$. ddd, J$_1$ = 5.6 Hz, J$_2$ = 15.5 Hz, J$_3$ = 22.2 Hz, 1H), 1.51 (—CH, td, J$_1$ = 6.6 Hz, J$_2$ = 13.1 Hz, 1H), 2.82-3.01 (—CH$_2$, m, 2H), 3.02-3.15 (—CH, m, 1H), 4.14 (—CH$_2$, d, J = 5.5 Hz, 4H), 4.62-4.88 (—CH, m, 1H), 6.64 (—Ph, d, J = 10.7 Hz, 2H), 6.71 (—Ph, d, J = 4.2 Hz, 1H), 8.62 (—CONH, t, J = 8.3 Hz, 1H), 8.68-8.78 (—Pyz, m, 1H), 8.79-8.93 (—Pyz, m, 2H), 9.05-9.17 (—CONH, m, 1H). $^{13}$C NMR. (CDCl$_3$, 100 MHz) δ 22.96, 25.89, 31.88, 37.60, 52.41, 58.34, 64.21, 117.30, 118.18, 122.35, 128.72, 142.68, 142.74, 143.44, 143.78, 144.22, 147.44, 162.94, 172.84. MS (ESI): m/z 441.1 [M − H]$^−$. HRMS (ESI): calcd for C$_{21}$H$_{27}$BN$_4$NaO$_6$ [M + Na]$^+$ 465.1919, found 469.1932. |

-continued

| No. | Structure | Chemical name and analytical data |
|---|---|---|
| IV-12 | 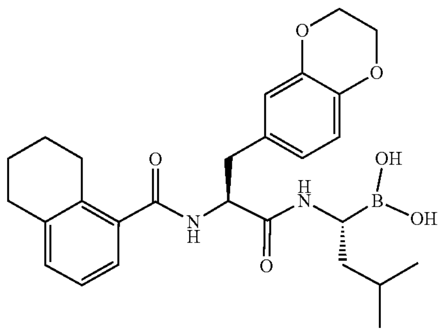 [SMILES: CC(C)C[C@H](NC(=O)[C@H](Cc1ccc2c(c1)OCCO2)NC(=O)c1cccc2c1CCCC2)B(O)O] | (S)-N-(5,6,7,8-tetrahydro-1-naphthoyl)-3-(2,3-dihydro-1,4-benzodioxol-6-yl)propionamido-D-leucine boric acid<br>Yield 32.3%. $^1$H NMR (400 MHz, CDCl$_3$) δ 0.83 (—CH$_3$, s, 3H), 0.86 (—CH$_3$, s, 3H), 1.41-1.51 (—CH$_2$, m, 2H), 1.52-1.64 (—CH, m, 1H), 1.73 (—CH$_2$, s, 4H), 2.50-2.67 (—CH$_2$, m, 2H), 2.73 (—CH$_2$, s, 2H), 2.88-2.98 (—CH, m, 1H), 2.99-3.15 (—CH$_2$, m, 2H), 4.11-4.31 (—CH$_2$, m, 4H), 4.82-4.99 (CH, m, 1H), 6.44-6.62 (—CONH, m, 1H), 6.63-6.82 (—Ph, m, 3H), 7.04 (—Ph, ddd, J$_1$ = 9.2 Hz, J$_2$ = 11.8 Hz, J$_3$ = 14.2 Hz, 3H), 7.37-7.97 (—CONH, m, 1H). $^{13}$C NMR (CDCl$_3$, 100 MHz) δ 22.41, 22.54, 22.87, 25.82, 26.54, 29.71, 31.88, 39.97, 52.20, 52.69, 64.25, 117.23, 118.17, 122.18, 124.03, 125.12, 129.14, 131.09, 134.83, 135.61, 138.02, 142.49, 143.37, 170.43, 173.44. MS (ESI): m/z 493.2 [M − H]$^-$. HRMS (ESI): calcd for C$_{27}$H$_{35}$BN$_2$NaO$_6$ [M + Na]$^+$ 465.1919, found 465.1932. |
| IV-13 | 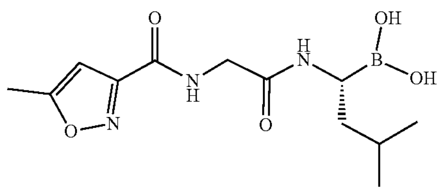 [SMILES: Cc1cc(C(=O)NCC(=O)N[C@@H](CC(C)C)B(O)O)no1] | N-(5-methylisoxazol-3-formyl)acetamido-D-leucine boric acid<br>Yield 32.0%. $^1$H NMR (400 MHz, DMSO) δ 0.77 (—CH$_3$, s, 3H), 0.79 (—CH$_3$, s, 3H), 1.24 (—CH$_2$, dd, J$_1$ = 6.9 Hz, J$_2$ = 16.1 Hz, 2H), 1.56 (—CH, td, J$_1$ = 6A Hz, J$_2$ =13.0 Hz, 1H), 2.47 (—CH$_3$, s, 3H), 2.56 (—CH, s, 1H), 3.99 (—CH$_2$, d, J = 5.7 Hz, 2H), 6.57 (—CH, s, 1H), 8.80 (—CONH, s, 1H), 8.88 (—CONH, t, 5.9 Hz, 1H). $^{13}$C NMR (DMSO, 100 MHz) δ 12.36, 22.95, 25.89, 29.80, 39.89, 40.62, 101.61, 158.25, 160.16, 171.47, 172.25. MS (ESI): m/z 296.1 [M − H]$^-$. HRMS (ESI): calcd for C$_{12}$H$_{20}$BN$_3$NaO$_5$ [M + Na]$^+$ 320.1390, found 320.1397. |
| IV-14 | 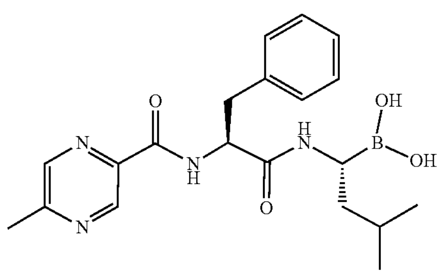 [SMILES: Cc1cnc(C(=O)N[C@@H](Cc2ccccc2)C(=O)N[C@@H](CC(C)C)B(O)O)cn1] | (S)-N-(5-methyl-2-pyrazinylformyl)phenylpropionamido-D-leucine boric acid<br>Yield 67.9%. $^1$H NMR (400 MHz, CDCl$_3$) δ 0.76 (—CH$_3$, s, 3H), 0.82 (—CH$_3$, s, 3H), 1.36 (—CH$_2$, d, J = 8.3 Hz, 2H), 1.53-1.75 (—CH, m, 1H), 2.62 (—CH$_3$, s, 3H), 2.97-3.21 (—CH$_2$, m, 2H), 3.21-3.34 (—CH, m, 1H), 4.70-5.03 (—CH, m, 1H), 6.94 (—CONH, dd, J$_1$ = 15.7 Hz, J$_2$ = 80.4 Hz, 1H), 7.24 (—Ph, dd, J$_1$ = 5.3 Hz, J$_2$ = 9.9 Hz, 5H), 8.27 (—CONH, dd, J$_1$ = 13 Hz, J$_2$ = 14.7 Hz, 1H), 8.31-8.44 (—Pyz, m, 1H), 9.02-9.21 (—Pyz, m, 1H). $^{13}$C NMR (CDCl$_3$, 100 MHz) δ 21.78, 23.96, 26.50, 33.85, 38.07, 51.25, 52.23, 127.10, 128.60, 129.38, 136.06, 142.50, 143.23, 156.83, 157.50, 163.33, 171.59. MS (ESI): m/z 397.2 [M − H]$^-$. HRMS (ESI): calcd for C$_{20}$H$_{27}$BN$_4$NaO$_4$ [M + Na]$^+$ 421.2021, found 421.2041. |
| IV-15 | 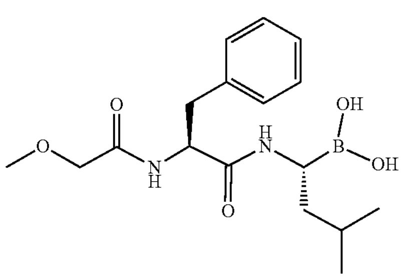 [SMILES: COCC(=O)N[C@@H](Cc1ccccc1)C(=O)N[C@@H](CC(C)C)B(O)O] | (S)-N-(methoxyacetyl)phenylpropionamido-D-leucine boric acid<br>Yield 80.0%. $^1$H NMR (400 MHz, CDCl$_3$) δ 0.84 (—CH$_3$, —CH$_3$, d, J = 4.1 Hz, 6H), 1.35 (—CH$_2$, d, 15.2 Hz, 2H), 1.42 (—CH, d, J = 5.1 Hz, 1H), 2.87 (—CH, s, 1H), 3.11 (—PhCH$_2$, d, J = 46.7 Hz, 2H), 3.31 (—OCH$_3$, s, 3H) 3.84 (—OCH$_2$, s, 2H), 4.74 (—CH, s, 1H), 7.09 (—CONH, s, 1H), 7.21 (—Ph, d, J = 7.8 Hz, 2H), 7.25 (—Ph, d, J = 8.8 Hz, 3H). $^{13}$C NMR (125 MHz, DMSO-d$_6$) δ 23.04, 25.86, 29.68, 37.99, 39.96, 51.80, 59.18, 71.60, 127.15, 128.65, 129.40, 135.86, 170.00, 172.89. MS (ESI): m/z 349.35 [M − H]$^-$. HRMS (ESI): calcd for C$_{17}$H$_{27}$BN$_2$NaO$_5$ [M + Na]$^+$ 373.1908, found 469.1965. |

| No. | Structure | Chemical name and analytical data |
|---|---|---|
| IV-16 | 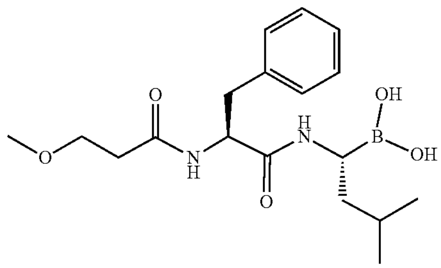 [SMILES: COCCC(=O)N[C@@H](Cc1ccccc1)C(=O)N[C@@H](CC(C)C)B(O)O] | (S)-N-(3-methoxypropionyl)phenylpropionamido-D-leucine boric acid<br>Yield 79.8%. $^1$H NMR (400 MHz, CDCl$_3$) δ 0.86 (—CH$_3$, —CH$_3$, d, J = 5.8 Hz, 6H), 1.34 (—CH$_2$, t, 12.7 Hz, 2H), 1.50-1.46 (—CH, m, 1H), 2.41-2.43 (—CH$_2$, m, 2H), 2.91 (—CH, s, 1H), 3.15-3.18 (—PhCH$_2$, m, 2H), 3.26 (—CH$_3$, s, 3H), 3.54 (—CH$_2$, dd, J = 22.4 Hz, 16.9 Hz, 2H), 4.83 (—CH, d, J = 7.2 Hz, 1H), 6.81 (—CONH, s, 1H), 7.00-7.14 (—CONH, m, 1H), 7.22 (—Ph, t, J = 8.5 Hz, 3H), 7.29 (—Ph, d, J = 7.0 Hz, 2H). $^{13}$C NMR (125 MHz, DMSO-d$_6$) δ 23.05, 25.82, 29,34, 36.75, 37.40, 40.04, 52.06, 58.68, 68.46, 127.01, 128.57, 129.42, 136.13, 171.71, 173.59. MS (ESI): m/z 363.35 [M − H]$^-$. HRMS (ESI): calcd for C$_{18}$H$_{29}$BN$_2$NaO$_5$ [M + Na]$^+$ 387.2065, found 387.2059. |
| IV-17 | 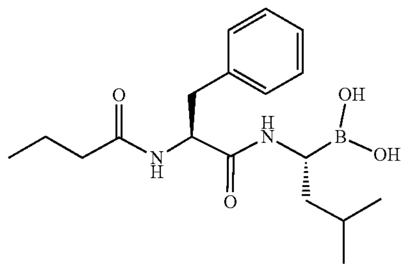 [SMILES: CCCC(=O)N[C@@H](Cc1ccccc1)C(=O)N[C@@H](CC(C)C)B(O)O] | (S)-N-(butanoyl)phenylpropionamido-D-leucine boric acid<br>Yield 76.3%. $^1$H NMR (400 MHz, CDCl$_3$) δ 0.80 (—CH$_3$, s, 3H), 0.86 (—CH$_3$, —CH$_3$, d, J = 6.3 Hz, 6H), 1.29-1.32 (—CH$_2$, m, 2H), 1.40-1.45 (—CH, m, 1H), 1.48-1.55 (—CH$_2$, m, 2H), 2.15-2.22 (—CH$_2$, m, 2H), 3.03-3.12 (—CH, m, 1H), 3.14-3.32 (—PhCH$_2$, m, 2H), 4.90 (—CH, dd, 14.3, 6.3 Hz, 1H), 6.70 (—CONH, s, 1H), 6.98 (—CONH, d, J = 7.5 Hz, 1H), 7.13 (—Ph, d, J = 6.8 Hz, 2H), 7.28 (—Ph, dt, J = 14.5 Hz, 6.9 Hz, 3H). $^{13}$C NMR (125 MHz, DMSO-d$_6$) δ 13.52, 19.26, 23.02, 25.85, 29.56, 36.85, 37.62, 39.98, 52.26, 127.11, 128.67, 129.44, 136.03, 170.73, 172.87. MS (ESI): m/z 347.34 [M − H]$^-$. HRMS (ESI): calcd for C$_{18}$H$_{29}$BN$_2$NaO$_4$ [M + Na]$^+$ 371.2115, found 371.2117. |
| IV-18 | 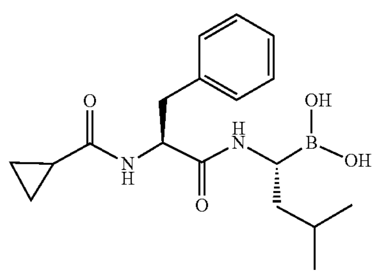 [SMILES: CC(C)C[C@H](NC(=O)[C@H](Cc1ccccc1)NC(=O)C1CC1)B(O)O] | (S)-N-(cyclopropylformyl)phenylpropionamido-D-leucine boric acid<br>Yield 56.1% $^1$H NMR (500 MHz, CD$_3$CD) δ 0.76-0.79 (—CH$_2$, m, 4H), 0.82 (—CH$_3$, t, J = 7.0 Hz, 6H). 1.07-1.11 (—CH$_2$, m, 2H), 1.32-1.37 (—CH, m, 1H), 1.64-1.69 (—CH, m, 1H), 2.64-2.67 (—CH, m, 1H), 3.06-3.15 (—CH$_2$, m, 2H), 4.74-4.77 (—CH, m, 1H), 7.22-7.32 (—Ph, m, 5H). $^{13}$C NMR (125 MHz, CD$_3$CD) δ 7.75, 14.41, 23.73, 26.58, 28.29, 38.43, 40.59, 52.81, 128.24, 129.68, 130.41, 136.87, 176.61, 178.20. MS (ESI) m/z 345.31 [M − H]$^-$. HRMS (ESI): calcd for C$_{18}$H$_{27}$BN$_2$NaO$_4$ [M + Na]$^+$ 369.1959, found 369.1958. |
| IV-19 | 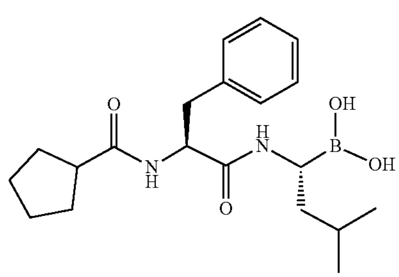 [SMILES: CC(C)C[C@H](NC(=O)[C@H](Cc1ccccc1)NC(=O)C1CCCC1)B(O)O] | (S)-N-(cyclopentylformyl)phenylpropionamido-D-leucine boric acid<br>Yield 70.1%; $^1$H NMR (500 MHz, CD$_3$CD) δ 0.83 (—CH$_3$, —CH$_3$, t, J = 6.8 Hz, 6H), 1.10-1.18 (—CH$_2$, m, 2H), 1.26-1.40 (—CH, m, 1H), 1.55-1.59 (—CH$_2$, —CH$_2$, m, 3H), 1.62-1.63 (—CH$_2$, —CH$_2$, m, 3H), 1.67-1.83 (—CH$_2$, —CH$_2$, m, 2H), 2.61-2.68 (—CH, m, 1H), 3.00-3.11 (CH$_2$, m, 2H), 4.75 (—CH, t, J = 8.0 Hz, 1H), 7.21-7.30 (—Ph, m, 5H). $^{13}$C NMR (125 MHz, CD$_3$CD) δ 21.94, 26.64, 26.91, 31.22, 31.43, 38.59, 40.82, 45.88, 52.50, 128.13, 129.62, 130.45, 137.17, 177.68, 179.16. MS (ESI) m/z 373.47 [M − H]$^-$. HRMS (ESI): calcd for C$_{20}$H$_{31}$BN$_2$NaO$_4$ [M + Na]$^+$ 397.2272, found 397.2269. |

The above-mentioned boric compound can react with, for example, citric acid, to produce borate ester compounds as a prodrug. The preparation method is as described in the following example, without limitation.

5. Production of (S)-diethanolamine N-(2,5-dichlorobenzoyl)-3-methoxypropionamido-D-leucine Borate

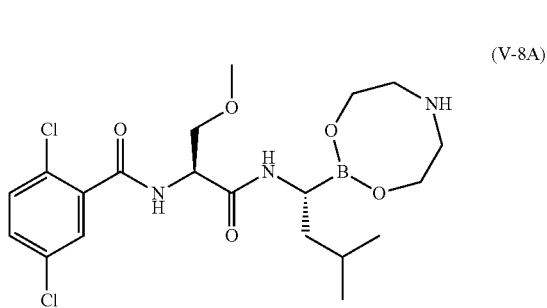 [SMILES: COC[C@H](NC(=O)c1cc(Cl)ccc1Cl)C(=O)N[C@@H](CC(C)C)B1OCCNCCO1]

(V-8A)

Diethanolamine (160 mg, 1.52 mmol) was dissolved in ethyl acetate (8 mL), and heated to 74° C. IV-1 (500 mg, 1.38 mmol) dissolved in ethyl acetate (1.5 mL) was added, slowly cooled to 60° C., reacted for 3 hrs, then slowly cooled to 25° C. and reacted overnight until the reaction was completed as indicated by TLC. After filtering, the filter cake was dried under vacuum to obtain a pure product (557 mg, yield 85.4%). $^1$H NMR (400 MHz, DMSO) δ 0.80 (—CH$_3$, dd, J$_1$=6.7 Hz, J$_2$=9.7 Hz, 6H), 1.12-1.39 (—CH$_2$, m, 2H), 1.59 (—CH, d, J=5.5 Hz, 1H), 2.75 (—CH$_2$, dd, J$_1$=6.4 Hz, J$_2$=26.3 Hz, 2H), 2.85-3.04 (—CH$_2$, m, 2H), 3.08-3.20 (—CH, m, 1H), 3.26 (—CH$_3$, s, 3H), 3.59 (—CH$_2$, dt, J$_1$=8.1 Hz, J$_2$=22.2 Hz, 4H), 3.69 (—CH$_2$, d, J=5.3 Hz, 2H), 4.59 (—CH, dd, J$_1$=6.7 Hz, J$_2$=12.9 Hz, 1H), 6.56 (—NH, s, 1H), 6.99 (—CONH d, J=8.2 Hz, 1H), 7.45 (-Ph, d, J=13.7 Hz, 1H), 7.54 (-Ph, s, 2H), 8.69-8.82 (—CONH, m, J=7.9 Hz, 1H). HRMS (ESI): calcd for C$_{20}$H$_{30}$BCl$_2$N$_3$O$_5$ [M+Na]$^+$ 496.1548, found: 497.1546.

6. Production of (S)—N-(2,5-dichlorobenzoyl)-3-methoxypropionamido-D-leucine Borate Citrate (V-8B)

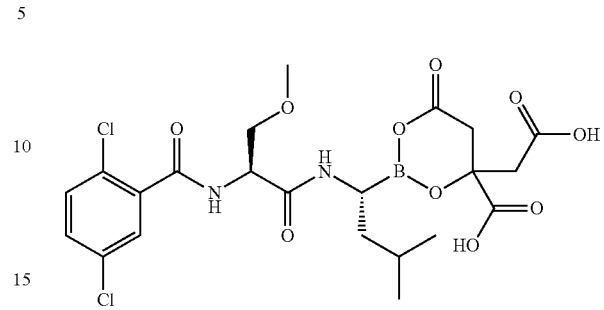

Citric acid (192.12 mg, 0.39 mmol) was dissolved in ethyl acetate (2 mL), and heated to 74° C. After citric acid was completely dissolved, Compound IV-1 (363.03 mg, 0.36 mmol) dissolved in ethyl acetate (1 mL) was added, slowly cooled to 60° C., reacted for 3 hrs, then slowly cooled to 25° C. and reacted overnight. After filtering, the filter cake was dried under vacuum to obtain a pure product (90.0 mg, yield 48.6%). $^1$H NMR (400 MHz, DMSO) δ 0.86 (—CH$_3$, d, 6.3 Hz, 6H), 1.39-1.21 (—CH$_2$, m, 2H), 1.70 (—CH, d, J=26.1 Hz, 1H), 2.81-2.52 (—CH$_2$, m, 4H), 2.88 (—CH$_3$, s, 1H), 3.15 (—CH$_3$, s, 3H)

3.30-3.55 (—CH$_2$, m, 2H), 4.46 (—CH, m, 1H) 7.78-7.44 (-Ph, m, 3H), 9.12 (—NH, s, 1H), 10.73 (—NH, s, 1H), 12.15 (—COOH, s, 2H). HRMS (ESI): calcd for C$_{20}$H$_{30}$BCl$_2$N$_3$O$_5$ [M+Na]$^+$ 583.1028, found: 583.1030.

The other diethanolamine borate and citrate borate prodrug compounds of the present invention can be synthesized by the methods described in Example 5 and Example 6. Specific compounds are shown in a Table below.

| No. | Structure | Chemical name and analytical data |
|---|---|---|
| V-8A | (structure shown) | (S)-diethanolamine N-(2,5-dichlorobenzoyl)-3-methoxypropionamido-D-leucine borate Yield 85.4%. $^1$H NMR (400 MHz, DMSO) δ 0.80 (—CH$_3$, dd, J$_1$ = 6.7 Hz, J$_2$ = 9.7 Hz, 6H), 1.12-1.39 (—CH$_2$, m, 2H), 1.59 (—CH, d, J = 5.5 Hz, 1H), 2.75 (—CH$_2$, dd, J$_1$ = 6.4 Hz, J$_2$ = 26.3 Hz, 2H), 2.85-3.04 (—CH$_2$, m, 2H), 3.08-3.20 (—CH, m, 1H), 3.26 (—CH$_3$, s, 3H), 3.59 (—CH$_2$, dt, J$_1$ = 8.1 Hz, J$_2$ = 22.2 Hz, 4H), 3.69 (—CH$_2$, d, J = 5.3 Hz, 2H), 4.59 (—CH, dd, J$_1$ = 6.7 Hz, J$_2$ = 12.9 Hz, 1H), 6.56 (—NH, s, 1H), 6.99 (—CONH, d, J = 8.2 Hz, 1H), 7.45 (—Ph, d, J = 13.7 Hz, 1H), 7.54 (—Ph, s, 2H), 8.69-8.82 (—CONH, m, J = 7.9 Hz, 1H). HRMS (ESI): calcd for C$_{20}$H$_{30}$BCl$_2$N$_3$O$_5$ [M + Na]$^+$ 496.1548, found: 496.1546 |

| No. | Structure | Chemical name and analytical data |
|---|---|---|
| V-8B | 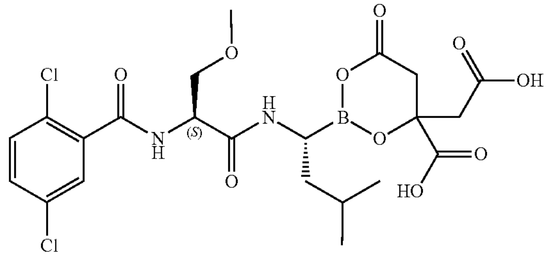 | (S)-N-(2,5-dichlorobenzoyl)-3-methoxypropionamido-D-leucine borate citrate<br>Yield 48.6%. $^1$H NMR (400 MHz, DMSO) δ 0.86 (—CH$_3$, d, J = 6.3 Hz, 6H), 1.39-1.21 (—CH$_2$, m, 2H), 1.70 (—CH, d, J = 26.1 Hz, 1H), 2.81-2.52 (—CH$_2$, m, 4H), 2.88 (—CH, s, 1H), 3.15 (—CH$_3$, s, 3H) 3.30-3.55 (—CH$_2$, m, 2H), 4.46(—CH, m, 1H), 7.78-7.44 (—Ph, m, 3H), 9.12 (—NH, s, 1H), 10.73 (—NH, s, 1H), 12.15 (—COOH, s, 2H). MS (ESI): observed: m/z 562.11 [M]+.<br>[M − H]$^-$. HRMS (ESI): calcd for C$_{22}$H$_{27}$BCl$_2$N$_2$O$_{10}$ [M + Na]$^+$ 583.1028, found 583.1030. |
| V-9A | 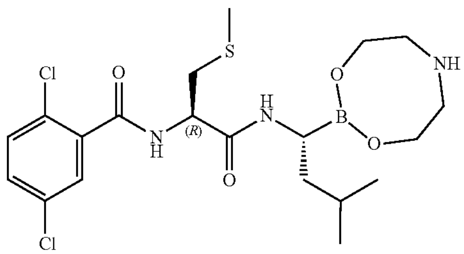 | (R)-diethanolamine N-(2,5-dichlorobenzoyl)-3-methylmercaptopropionamido-D-leucine borate<br>$^1$H NMR (400 MHz, DMSO) δ 0.87(—CH$_3$, dd, J$_1$ = 6.7 Hz, J$_2$ = 9.7 Hz, 6H), 1.12-1.39 (—CH$_2$, m, 2H), 1.59 (—CH, d, J = 5.5 Hz, 1H), 2.17 (—CH$_3$, s, 3H), 2.75 (—CH$_2$, dd, J$_1$ = 6.4 Hz, J$_2$ = 26.3 Hz, 2H), 2.85-3.04 (—CH$_2$, m, 2H), 3.24-3.51 (—CH, m, 1H), 3.87 (—CH$_2$, dt, J$_1$ = 8.1 Hz, J$_2$ = 22.2 Hz, 4H), 4.63 (—CH, dd, J$_1$ = 6.7 Hz, J$_2$ = 12.9 Hz, 1H), 5.66 (—NH, s, 1H), 6.99 (—CONH, d, J = 8.2 Hz, 1H), 7.45 (—Ph, d, J = 13.7 Hz, 1H), 7.54 (—Ph, s, 2H), 8.69-8.82 (—CONH, m, J = 7.9 Hz, 1H). HRMS (ESI): calcd for C$_{22}$H$_{27}$BCl$_2$N$_2$O$_{10}$ [M + Na]$^+$ 512.1319, found 512.1315. |
| V-9B | 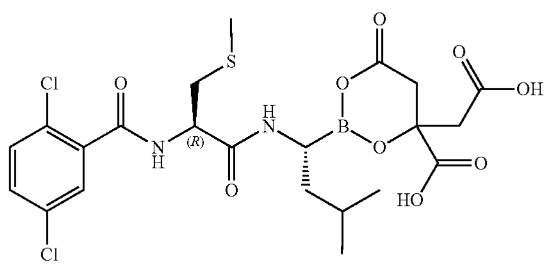 | (R)-N-(2,5-dichlorobenzoyl)-3-methylmercaptopropionamido-D-leucine borate citratte<br>Yield 78.4%. $^1$H NMR (400 MHz, DMSO) δ 0.81 (—CH$_3$, d, J = 6.3 Hz, 6H), 1.18-1.24 (—CH$_2$, m, 2H), 1.55 (—CH, d, J = 26.1 Hz, 1H), 2.16 (—CH$_3$, s, 3H), 2.84-2.58 (—CH$_2$, m, 4H), 2.88 (—CH, s, 1H), 3.30-3.55 (—CH$_2$, m, 2H), 4.48 (—CH, m, 1H), 7.78-7.44 (—Ph, m, 3H), 8.67 (—NH, s, 1H), 9.68 (—NH, s, 1H), 12.34 (—COOH, s, 2H), HRMS (ESI): calcd for C$_{22}$H$_{27}$BCl$_2$N$_2$O$_9$S [M + Na]$^+$ 599.0800, found 599.0806. |
| V-10A | 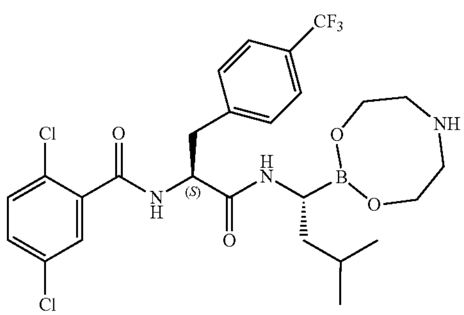 | (S)-diethanolamine N-(2,5-dichlorobenzoyl)-3-(4-trifluoromethylphenyl) propionamido-D-leucine borate<br>Yield 73.3%. $^1$H NMR (400 MHz, CDCl$_3$) δ 0.69 (—CH$_3$, s, 3H), 0.83 (—CH$_3$, s, 3H), 1.26 (—CH$_2$, d, J = 11.4 Hz, 2H), 1.39 (—CH, dt, J$_1$ = 6.3 Hz, J$_2$ = 13.0 Hz, 1H), 2.76 (—CH$_2$, m, 4H), 2.93 (—CH, dd, J$_1$ = 77.8 Hz, J$_2$ = 115.9 Hz, 1H), 3.18-3.41 (—CH$_2$, m, 2H), 3.89 (—CH$_2$, m, 4H), 4.79-5.30 (—CH, m, 1H), 6.31-7.24 (—CONH, m, 1H), 7.40 (—Ph, dd, J$_1$ = 7.7 Hz, J$_2$ = 25.1 Hz, 2H), 7.52 (—Ph, d, 8.1 Hz, 2H), 8.16-8.40 (—Pyz, m, 1H), 8.41-8.57 (—Pyz, m, 1H), 8.66-8.81 (—Pyz, m, 1H), 9.10-9.36 (—CONH, m, 1H). $^{13}$C NMR (CDCl$_3$, 100 MHz) δ 22.7, 25.71, 37.89, 39.82, 52.12, 53.6, 54.32, 62.5, 125.31, 125.48, 129.63, 129.80, 139.80, 142.73, 144.17, 163.09, 172.24. HRMS (ESI): calcd for C$_{26}$H$_{31}$BCl$_2$F$_3$N$_3$O$_4$ [M + Na]$^+$ 610.1629, found 610.1635. |

| No. | Structure | Chemical name and analytical data |
|---|---|---|
| V-10B | 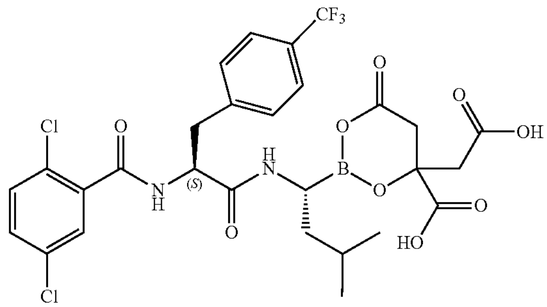 | (S)-N-(2,5-dichlorobenzoyl)-3-(4-trifluoromethylphenyl) propionamido-D-leucine borate citrate<br>Yield 73.3%. $^1$H NMR (400 MHz, CDCl$_3$) δ 0.69 (—CH$_3$, s, 3H), 0.83 (—CH$_3$, s, 3H), 1.26 (—CH$_2$, d, J = 11.4 Hz, 2H), 1.39 (—CH, dt, J$_1$= 6.3 Hz, J$_2$ = 13.0 Hz, 1H), 2.49-2.67 (—CH$_2$, m, 4H), 2.93 (—CH, dd, J$_1$ = 77.8 Hz, J$_2$ = 115.9 Hz, 1H), 3.18-3.41 (—CH$_2$, m, 2H), 4.79-5.30 (—CH, m, 1H), 6.31-7.24 (—CONH, m, 1H), 7.40 (—Ph, dd, J$_1$ = 7.7 Hz, J$_2$ = 25.1 Hz, 2H), 7.52 (—Ph, d, J = 8.1 Hz, 2H), 8.16-8.40 (—Pyz, m, 1H), 8.41-8.57 (—Pyz, m, 1H), 8.66-8.81 (—Pyz, m, 1H), 9.10-9.36 (—CONH, m, 1H), 14.27 (—COOH, s, 2H). $^{13}$C NMR (CDCl$_3$, 100 MHz) δ 22.7, 25.71, 37.89, 39.82, 52.12, 54.32, 125.31, 125.48, 129.63, 129.80, 139.80, 142.73, 144.17, 163.09, 172.24, 174.4, 175.6, 175.9. HRMS (ESI): calcd for C$_{28}$H$_{28}$BCl$_2$F$_3$N$_2$O$_9$ [M + Na]$^+$ 697.1109, found 697.1114. |
| V-11A | 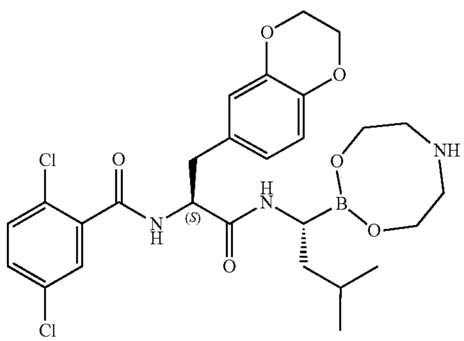 | (S)-diethanolamine N-(2,5-dichlorobenzoyl)-3-(2,3-dihydro-1,4-benzodioxol-6-yl) propionamido-D-leucine borate<br>Yield 74.7%. $^1$H NMR (400 MHz, DMSO) δ 0.74 (—CH$_3$, s, 3H), 0.84 (—CH$_3$, s, 3H), 1.02-1.21 (—CH$_2$, m, 1H), 1.35 (—CH$_2$, ddd, J$_1$ = 5.6 Hz, J$_2$ = 15.5 Hz, J$_3$ = 22.2 Hz, 1H), 1.51 (—CH, td, J$_1$ = 6.6 Hz, J$_2$ = 13.1 Hz, 1H), 2.65(—CH$_2$, m, 4H), 2.82-3.01 (—CH$_2$, m, 2H), 3.02-3.15 (—CH, m, 1H), 3.78 (—CH$_2$, m, 4H), 4.14 (—CH$_2$, d, J = 5.5 Hz, 4H), 4.62-4.88 (—CH, m, 1H), 6.64 (—Ph, d, J = 10.7 Hz, 2H), 6.71 (—PH, d, J = 4.2 Hz, 1H), 8.62 (—CONH, t, J = 8.3 Hz, 1H), 8.68-8.78 (—Pyz, m, 1H), 8.79-8.93 (—Pyz, m, 2H), 9.05-9.17 (—CONH, m, 1H). $^{13}$C NMR (CDCl$_3$, 100 MHz) δ 22.96, 25.89, 31.88, 37.60, 52.6, 52.41, 58.34, 63.2, 64.21, 117.30, 118.18, 122.35, 128.72, 142.68, 142.74, 143.44, 143.78, 144.22, 147.44, 162.94, 172.84. HRMS (ESI): calcd for C$_{27}$H$_{34}$BCl$_2$N$_3$O$_6$ [M + Na]$^+$ 610.1810, found 610.1816. |
| V-11B | 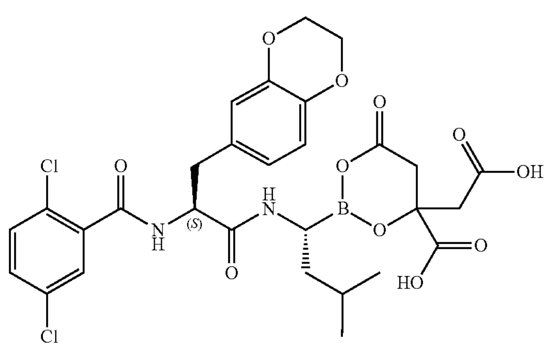 | (S)-diethanolamine N-(2,5-dichlorobenzoyl)-3-(2,3-dihydro-1,4-benzodioxol-6-yl) propionamido-D-1eucine borate<br>Yield 74.7%. $^1$H NMR (400 MHz, DMSO) δ 0.74 (—CH$_3$, s, 3H), 0.84 (—CH$_3$, s, 3H), 1.02-1.21 (—CH$_2$, m, 1H), 1.35 (—CH$_2$, ddd, J$_1$ = 5.6 Hz, J$_2$ = 15.5 Hz, J$_3$ = 22.2 Hz, 1H), 1.51 (—CH, td, J$_1$ = 6.6 Hz, J$_2$ = 13.1 Hz, 1H), 2.73 (—CH$_2$, m, 4H), 2.82-3.01 (—CH$_2$, m, 2H), 3.02-3.15 (—CH, m, 1H), 4.14 (—CH$_2$, d, J = 5.5 Hz, 4H), 4.62-4.88 (—CH, m, 1H), 6.64 (—Ph, d, J = 10.7 Hz, 2H), 6.71 (—Ph, d, J = 4.2 Hz, 1H), 8.62 (—CONH, t, J = 8.3 Hz, 1H), 8.68-8.78 (—Pyz, m, 1H), 8.79-8.93 (—Pyz, m, 2H), 9.05-9.17 (—CONH, m, 1H), 14.16 (—COOH, s, 2H). $^{13}$C NMR (CDCl$_3$, 100 MHz) δ 22.96, 25.89, 31.88, 37.60, 41.7, 44.8, 52.41, 58.34, 64.21, 78.6, 117.30, 118.18, 122.35, 128.72, 142.68, 142.74, 143.44, 143.78, |

-continued

| No. | Structure | Chemical name and analytical data |
|---|---|---|
| | | 144.22, 147.44, 162.94, 172.84, 174.7, 175.2, 175.7. HRMS (ESI): calcd for $C_{29}H_{31}BCl_2N_2O_{11}$ [M + Na]$^+$ 687.1290, found 687.1294. |
| V-12A | 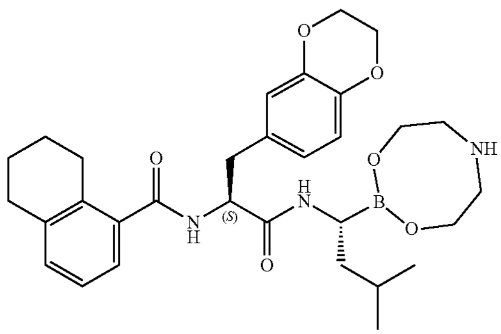 | (S)-N-(5,6,7,8-tetrahydro-1-naphthoyl)-3-(2,3-dihydro-1,4-benzodioxol-6-yl)propionamido-D-leucine boric acid<br>Yield 32.3%. $^1$H NMR (400 MHz, CDCl$_3$) δ 0.83 (—CH$_3$, s, 3H), 0.86 (—CH$_3$, s, 3H), 1.41-1.51 (—CH$_2$, m, 2H), 1.52-1.64 (—CH, m, 1H), 1.73 (—CH$_2$, s, 4H), 2.50-2.67 (—CH$_2$, m, 2H), 2.73 (—CH$_2$, s, 2H), 2.88-2.98 (—CH, m, 1H), 2.99-3.15 (—CH$_2$, m, 2H), 4.11-4.31 (—CH$_2$, m, 4H). 4.82-4.99 (CH, m, 1H), 6.44-6.62 (—CONH, m, 1H), 6.63-6.82 (—Ph, m, 3H), 7.04 (—Ph, ddd, J$_1$ = 9.2 Hz, J$_2$ = 11.8 Hz, J$_3$ = 14.2 Hz, 3H), 7.37-7.97 (—CONH, m, 1H). $^{13}$C NMR (CDCl$_3$, 100 MHz) δ 22.41, 22.54, 22.87, 25.82, 26.54, 29.71, 31.88, 39.97, 52.20, 52.69, 53.4, 63.7, 64.25, 117.23, 118.17, 122.18, 124.03, 125.12, 129.14, 131.09, 134.83, 135.61, 138.02, 142.49, 143.37, 170.43, 173.44. HRMS (ESI): calcd for $C_{31}H_{42}BN_3O_6$ [M + Na]$^+$ 586.3059, found 586.3063. |
| V-13A | 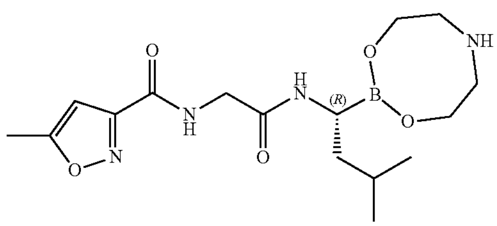 | Diethanolamine N-(5-methylisoxazol-3-formyl)acetamido-D-leucine borate<br>Yield 32.0%. $^1$H NMR (400 MHz, DMSO) δ 0.77 (—CH$_3$, s, 3H), 0.79 (—CH$_3$, s, 3H), 1.24 (—CH$_2$, dd, J$_1$ = 6.9 Hz, J$_2$ = 16.1 Hz, 2H), 1.56 (—CH, td, J$_1$ = 6.4 Hz, J$_2$ = 13.0 Hz, 1H), 2.47 (—CH$_3$, s, 3H), 2.56 (—CH, s, 1H), 2.88 (—CH, m, 4H), 3.99 (—CH$_2$, d, J = 5.7 Hz, 2H), 4.21 (—CH$_2$, m, 4H), 6.57 (—CH, s, 1H), 8.80 (—CONH, s, 1H), 8.88 (—CONH, t, J = 5.9 Hz, 1H). $^{13}$C NMR (DMSO, 100 MHz) δ 12.36, 22.95, 25.89, 29.80, 39.89, 40.62, 52.9, 62.6, 101.61, 158.25, 160.16, 171.47, 172.25. HRMS (ESI): calcd for $C_{16}H_{27}BN_4O_5$ [M + Na]$^+$ 389.1967, found 389.1974. |
| V-13B | 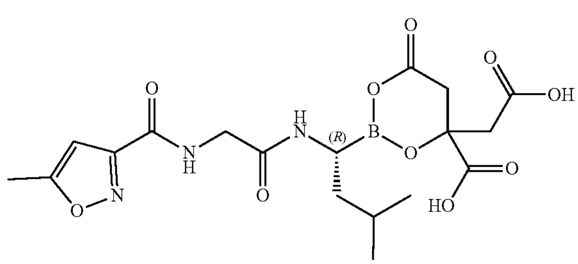 | N-(5-methylisoxazol-3-formyl)acetamido-D-leucine borate citrate<br>Yield 32.0%. $^1$H NMR (400 MHz, DMSO) δ 0.77 (—CH$_3$, s, 3H), 0.79 (—CH$_3$, s, 3H), 1.24 (—CH$_2$, dd, J$_1$ = 6.9 Hz, J$_2$ = 16.1 Hz, 2H), 1.56 (—CH, td, J$_1$ = 6.4 Hz, J$_2$ = 13.0 Hz, 1H), 2.47 (—CH$_3$, s, 3H), 2.49 (—CH$_2$, d, 2H) 2.56 (—CH s, 1H), 2.88 (—CH$_2$, d, 2H), 3.99 (—CH$_2$, d, J = 5.7 Hz, 2H), 6.57 (—CH, s, 1H), 8.80 (—CONH, s, 1H), 8.88 (—CONH, t, J = 5.9 Hz, 1H). $^{13}$C NMR (DMSO, 100 MHz) δ 12.36, 22.95, 25.89, 29.80, 39.89, 40.62, 41.7, 44.8, 78.6, 101.61, 158.25, 160.16, 171.47, 172.25, 174.5, 175.2, 175.7. HRMS (ESI): calcd for $C_{18}H_{24}BN_3O_{10}$ [M + Na]$^+$ 476.1447, found 476.1459. |

Section II: Assay of Inhibition on Proteasome Activity

Proteasome Inhibitory Activity

In the present invention, the fluorescent polypeptide substrate Suc-Leu-Leu-Val-Tyr-AMC Suc-LLVY-AMC, where Suc denotes a succinyl group, and AMC denotes 7-amido-4-methyl coumarin) is used to determine the chymotrypsin-like enzymatic activity of proteasome.

The proteasome used in the present invention is human erythrocyte 20S proteasome, and the enzyme, fluorescent substrate and test buffer are all purchased from Enzo. The experimental system is 16 μL, of which the substrate is 8 μL; the proteasome is 4 μL (0.8 ng) and has a final concentration of 50 μM; the test agent (inhibitor) is 4 μL, and has a final concentration of $2\times10^{-6}$ M-$4.88\times10^{-10}$ M, and the last concentration is 0 M, where the actually formulated concentration is $8\times10^{-6}$M-$1.95\times10^{-9}$M, and the last concentration is 0 M. The specific experimental process is as follows.

1. Formulation of Agents:

An agent was weighed, and dissolved in DMSO to give a concentration of $10^{-2}$ M. 2 μL was pipetted to 98 μL of DMSO to give a concentration of $2\times10^{-4}$ M. Then 8 μL of the $2\times10^{-4}$ M solution was pipetted to 198 μL of $H_2O$ to give a concentration of $8\times10^{-6}$ M. Following the method, solutions having a concentration of $2\times10^{-6}$M, $5\times10^{-7}$M, $1.25\times10^{-7}$M, $3.12\times10^{-8}$M, $7.8\times10^{-9}$M, and $1.95\times10^{-9}$M were respectively obtained, and the last concentration was 0 M, in which no agent was added.

2. Substrate Preparation:

25 mg of a fluorescent peptide substrate was dissolved in 654 μL of DMSO to obtain a 50 mM stock solution, which was stored at −20° C., and diluted 500 times when used. 8 μL was added to each sample, so that the final substrate concentration in the reaction system was 5 μM.

3. Preparation of Reaction System:

The 20S proteasome (2 ng/μL) was diluted with the buffer into a solution with a concentration of 8 ng/μL, and added to a 384-well fluorescent microplate in an amount of 4 μL per well. Then 4 μL of the test sample was added to each well. The marketed drug Velcade was a positive control drug. The reaction was continued for 15 min at 37° C. After the reaction, 8 μL of the fluorescent substrate was added to each well, and reacted for 1 hr at 37° C. in the dark. The fluorescence intensity was measured on a 360 nm/460 nm fluorescent microplate reader (BMG LABTECH POLARstar OPTIMA Microplate Reader).

4. Data Processing

The fluorescence intensity of the product obtained in the presence of different concentrations of the agent after subtracting the background was calculated.

The $IC_{50}$ concentration of the agent to inhibit the proteasome was calculated by GraphPad Prism software.

The results for some compounds are shown below:

| Compound No. | $IC_{50}$ (nM) |
| --- | --- |
| IV-8 | 7.517 |
| IV-9 | 4.862 |
| V-8A | 7.023 |
| V-8B | 8.197 |
| V-9A | 5.686 |
| V-9B | 6.597 |
| Velcade | 9.916 |
| MLN-9708 | 7.468 |

The chemical structural formulas of Velcade and MLN9708 are:

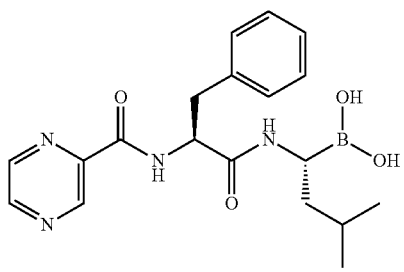

Velcade

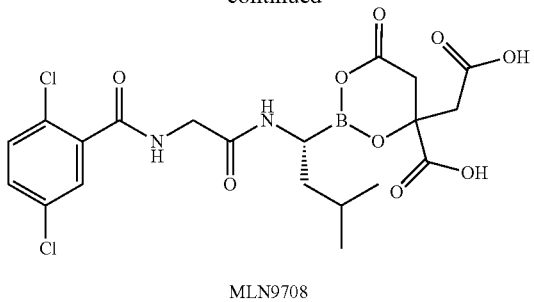

MLN9708

Cell Inhibitory Activity

The detection solution used in the present invention is One Solution Cell Proliferation Detection Kit from Promega; and the cells used are U266, RPMI8226, and ARH77. The experimental system is 110 μL, of which the cell suspension is 90 μL; the detection solution is 10 μl; and the test agent (inhibitor) is 10 μL, and has a final concentration of $4.54\times10^{-8}$ M-$1.77\times10^{-9}$ M, and the last concentration is 0 M, where the actually formulated concentration is $5\times10^{-7}$M-$1.95\times10^{-8}$M, and the last concentration is 0 M. The specific experimental process is as follows.

1. Formulation of Agents:

An agent was weighed accurately, and dissolved in DMSO to give a concentration of $10^{-2}$ M. 1 μL was pipetted to 199 μL of DMSO to give a concentration of $5\times10^{-5}$M. Then 3.3 μL of the $5\times10^{-5}$ M solution was pipetted to 326.7 μL of serum-free RPMI1640 medium to give a concentration of $5\times10^{-7}$ M, and then 1.5-fold serially diluted, to obtain solutions having a concentration of $3.3\times10^{-7}$M, $2.2\times10^{-7}$M, $1.48\times10^{-7}$M, $9.87\times10^{-8}$M, $6.58\times10^{-8}$M, $4.38\times10^{-8}$M, $2.92\times10^{-8}$M, and $1.95\times10^{-8}$M respectively. The last concentration was 0 M, in which no agent was added.

2. Formulation of Cell Suspension

After the cells were counted separately, U266 was diluted and formulated in an amount of $1\times10^4$ cells/well, RPMI8226 and ARH77 were diluted and formulated in an amount of $1\times10^4$ cells/well.

3. Preparation of Reaction System:

The cell suspension was added in 90 μL per well to a 96-well fluorescent microplate, and incubated for 24 hrs. Then, 10 μL of the test sample was added to each well and incubated for 24 hrs. The marketed drug Velcade was a positive control drug. After reaction, the detection solution was added in 10 μL per well, and incubated for 2-3 hrs. The absorbency was measured on a fluorescence microplate reader (BMG LABTECH POLARstar OPTIMA Microplate Reader) at 490 nm.

4. Data Processing

The absorbency of the product obtained in the presence of different concentrations of the agent after subtracting the background was calculated.

The results for some compounds are shown below:

| No. | RPMI8226 | ARH-77 | U266B1 | No. | RPMI8226 | ARH-77 | U266B1 |
|---|---|---|---|---|---|---|---|
| IV-8 | 8.99 | 9.10 | 6.75 | V-9A | 8.66 | 8.96 | 6.54 |
| IV-9 | 8.97 | 8.85 | 6.45 | V-9B | 8.17 | 9.34 | 6.42 |
| IV-10 | 150.4 | 58.03 | 79.89 | V-8A | 8.43 | 8.21 | 7.02 |
| IV-11 | 43.44 | 29.26 | 30.26 | V-8B | 8.15 | 8.93 | 7.14 |
| Velcade | 11.2 | 9.57 | 11.63 | MLN2238 | 55.32 | 65.50 | 52.15 |
| MLN9708 | 49.74 | 43.25 | 67.1 | | | | |

From the test results of n-vitro enzyme activity and cytotoxicity, it can be found that the compounds and their prodrugs of the present invention show better activity in in-vitro enzyme activity assay and in a variety of cells compared with the currently marketed proteasome drugs.

In-Vivo Pharmacokinetic Evaluation

Twelve male SD rats weighing 220±20g, were randomly divided into four groups.

Two groups were respectively given IV-9 and V-9A by tail vein injection at doses given in a table below, and before and 10 min, 20 min. 30 min, 1 h, 2 h, 4 h, 8 h, 12 h, 24 h and 36 h after administration, about 0.200 mL of blood was collected from the jugular vein, placed in a test tube containing EDTA-K2, and centrifuged at a high speed (7800×g) for 15 min. The plasma was separated, and stored at −15° C. to −35° C. The pharmacokinetic differences of IV-9 and V-9A administered by intravenous injection were compared.

The other two groups were respectively given IV-9 and V-9A by oral gavage at doses given in a table below, and before and 5 min, 10 min, 20 min, 30 min, 1 h, 2 h, 4 h, 8 h, 12 h, 24 h and 36 h after administration, about 0.200 mL of blood was collected from the jugular vein, placed in a test tube containing EDTA-K2, and centrifuged at a high speed (7800×g) for 15 min. The plasma was separated, and stored at −15° C. to −35° C. The pharmacokinetic differences of IV-9 and V-9A administered by oral gavage were compared.

Comparison of Pharmacokinetic Parameters of V-9A and its Prodrug (IV-9)

| Compound | | Dose (mg/kg) | $T_{1/2}$ (h) | $AUC_{last}$ (h*ng/ml) | $MRT_{last}$ (h) | Vz_obs (ml/kg) | CL_obs (ml/h/kg) | F (%) |
|---|---|---|---|---|---|---|---|---|
| IV-9 | p.o | 2.0 | 2.14 | 208 | 2.35 | | | 11.0 |
| | i.v. | 2.0 | 2.08 | 1890 | 1.55 | 2914 | 986 | |
| V-9A | p.o. | 2.0 | 2.88 | 634 | 3.37 | | | 24.9 |
| | i.v. | 2.0 | 3.10 | 2546 | 2.18 | 3010 | 671 | |

From the above pharmacokinetic data, it can be seen that after Compound IV-9 is prepared into a diethanolamine borate prodrug (V-9A), the pharmacokinetic performance of the compound is significantly improved, the half-life ($T_{1/2}$) is extended, and the oral bioavailability is increased from 11% (IV-9) to 24.9% (V-9A). It can be seen that the series of peptide borate ester compounds preferred in the present invention have better pharmacokinetic performance than peptide boric acid compounds.

Evaluation in Animal Model of Xenotransplantation

The human multiple myeloma cell line ARH-77 was used to implant tumors under the skin of Balb/enude mice to establish a transplanted tumor model. The specific experimental process is as follows.

1. 4-6 week-old Balb/c nude mice purchased from Shanghai Bikai Laboratory Animal Co., Ltd., were transferred to a barrier system to adapt to the environment for one week.

2. The cells were cultured to the logarithmic growth phase, digested, centrifuged, re-suspended in Matrigel at a density of 1×10$^7$ cells/ml, and placed on ice for later use. In the barrier system, the tumor cells were inoculated into the axilla of the animal's right forelimb in an amount of 1×10$^6$ cells per animal, and the inoculation volume for each animal was 100 microliters.

3. The animals were grown and the tumor volume was measured by a vernier caliper. When the average volume was increased to 100-150 mm$^3$, the animals were randomly divided into three groups including a blank control group, a positive drug group (Compound MLN-9708) and an experimental group (Compound MLN-9708). V-2A), each group having 6 animals.

The formula for calculating tumor volume is:

$$\text{Volume}_{(mm^3)} = 0.5 \times (\text{Length}_{(mm)} \times \text{Width}_{(mm)}^2)$$

4. The compound used was formulated with a 5% R-sulfobutyl cyclodextrin sodium aqueous solution to give an appropriate concentration, ultrasonicated until the solution became clear, and then stored in a refrigerator at 4° C. for later use.

5. The mice were orally administered. The frequency of administration for the positive drug group was twice a week, and the dosage was 5 mg/kg. The mice in the experimental group were administered daily, and the dosage was 1 mg/kg. The administration was continuous for three weeks, and then the mice were sacrificed to end the experiment. During this process, the tumor volume was measured and recorded twice a week. The inhibitory effect of agents on tumor growth was calculated by the GraphPad Prism software. The specific experimental results are shown in FIG. 1.

Influence on Growth of ARH-77 Xenograft Tumors after Administration

| Group | TV Mean (mm$^3$) | RTV Mean | T/C (%) | TW Mean (Day 21, g) | TGI (%) |
|---|---|---|---|---|---|
| Control | 2166.52 | 15.49 | | 1.78 | |
| MLN9708 (5 mg/kg) | 1042.71 | 9.13 | 58.94% | 1.33 | 25.28% |
| V-9A (1 mg/kg) | 354.78 | 3.72 | 24.02% | 0.65 | 63.48% |

According to the above results, it can be known that Compound V-9A has a tumor inhibition rate of 63.48% at a dose of 1 mg/kg, which is significantly higher than the tumor inhibition rate of the marketed oral proteasome inhibitor MLN-9708 at 5 mg/kg (25.28%). The above research results prove that, compared with the products available on the market, V-9A exhibits better in-vivo efficacy at a lower dose.

In-Vivo Study on the Pharmacodynamics in Blood Cells

The compound designed in the present invention can be used to treat malignant tumors of the blood system, so the efficacy of the compound was evaluated by detecting the activity of the proteasome in the blood after single administration, and the in-vivo pharmacodynamic study can be carried out by blood sampling at different time points.

The specific experimental process is as follows.

1. 8 week-old ICR mice purchased from Shanghai Bikai Laboratory Animal Co., Ltd., were transferred to a barrier system to adapt to the environment for one week.

2. The animals were divided into three groups, including a positive control group (MLN9708) and two experimental groups (IV-9, V-9A), each group having 3 animals.

3. Before administration, 100 µL of blood was sampled from each animal from the orbital venus plexus and used as the blank control, and the proteasome activity measured in blood cells in this sample was taken as 100%. 1 and 24 hrs after administration, blood was sampled from the orbital venus plexus, and the proteasome activity in blood cells was detected. The inhibitory effect of the drug on proteasome activity and recovery of proteasome activity in blood was obtained by comparison with the data at time 0.

4. The agent was orally administered, and the administered dose of MLN9708 was 5 mg/kg; and the administered dose of IV-9 and V-9A was 2 mg/kg.

5. The kit for detecting proteasome activity in blood cells was purchased from Promega. The specific experimental steps were as follows. 100 µL of whole blood was drawn, and 500 µL of PBS was added to wash and collect red blood cells. After further washing, 100 µL of PBS was added to re-suspend the blood cell, and 50 µL of the suspension was drawn. A cell lysing solution was added for protein quantification to correct the detected value. Additional 20 µL was drawn and 5-fold diluted with PBS to 100 µL. The dilution was further reacted with the fluorescent peptide substrate to detect the proteasome activity on a microplate reader.

Figure 2:
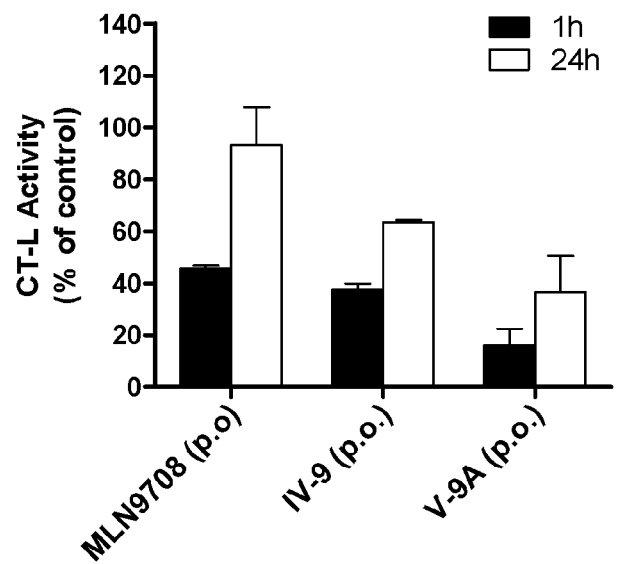
FIG. 2 shows the detection results of proteasome activity in blood cells.

The specific data obtained in the experiment is shown in FIG. 2. The results of the study show that 1 hr after administration, Compound IV-9 achieves an inhibitory activity that is basically comparable to that of MLN9708, and V-9A has an even better inhibitory activity. 24 hrs after administration, the proteasome activity in the MLN9708 group is recovered to 80% of the activity in the control group, the proteasome activity in the IV-9 is recovered only to 60% of the activity in the control group, and the proteasome activity in the V-9A group is recovered only to 40% of the activity in the control group. The above research data shows that the compound of the present invention has better pharmacodynamic performance, and higher and extended potency in the body.

The therapeutic dose of the compound designed in the present invention can be determined according to the route of administration, the purpose of treatment, the patient's health status and the doctor's prescription. The concentration and proportion of the compound designed by the present invention in a drug combination will vary with a variety of factors, including the route of administration, dosage and chemical nature. For example, the compound designed by the present invention can be provided in an aqueous physiological buffer for parenteral administration in an amount of approximately 0.1 to 10% w/v. Some conventional dosage ranges are about 1 µg/kg to 1 g/kg per day. In a specific embodiment, the dosage ranges from about 10 µg/kg body weight to 100 mg/kg body weight per day. The dosage will vary according to the route of administration, the patient's health status, the type and degree of progression of the disease or disorder, the relative biological potency of the compound and the formulation of excipients. The effective dose can be calculated from the dose-response curve in an in-vitro or animal model test system.

What is claimed is:

1. A compound or a pharmaceutically acceptable salt thereof, which is one of:

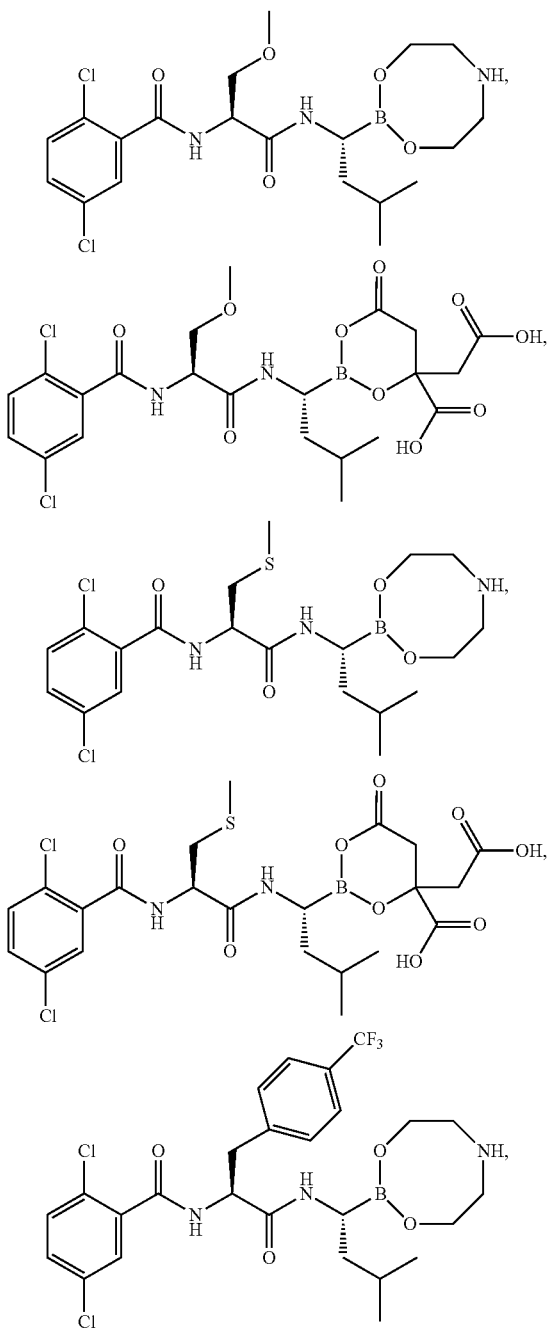

-continued

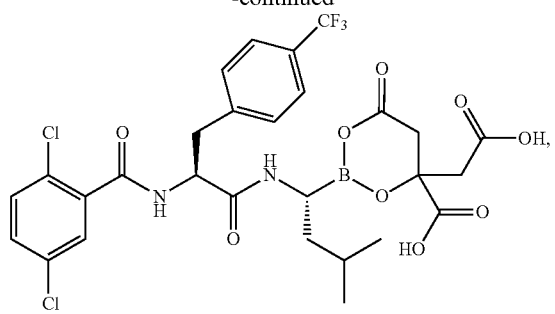

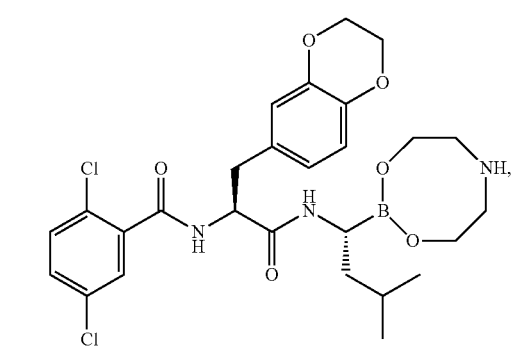

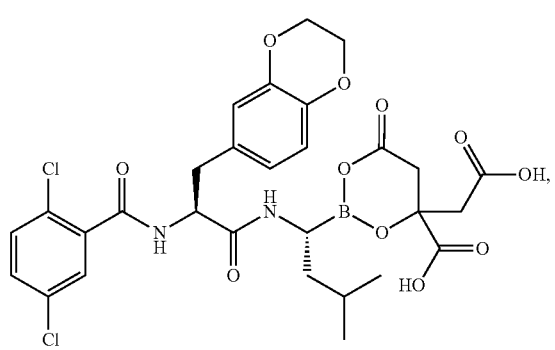

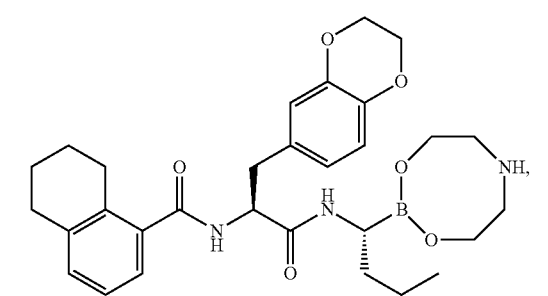

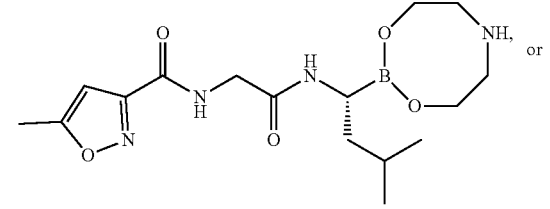

-continued

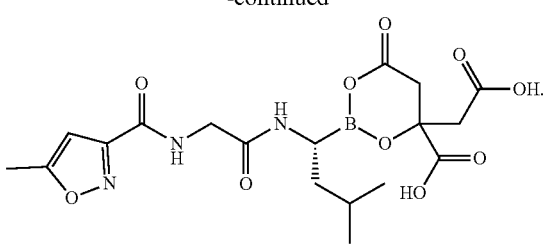

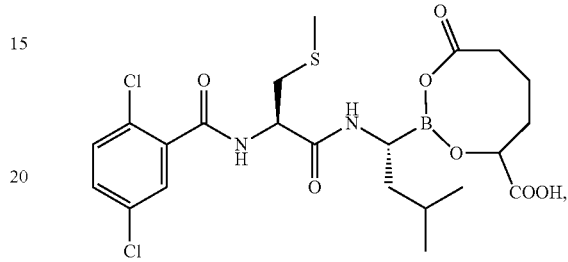

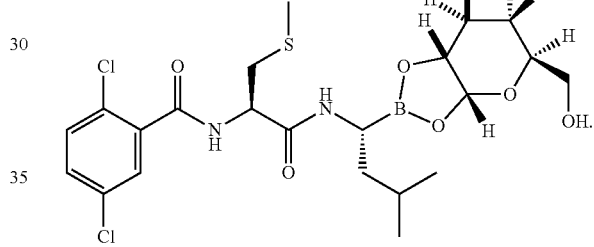

2. A pharmaceutical composition, comprising a pharmaceutical carrier and a compound according to claim 1, optionally combined with one or more other therapeutic agents simultaneously, separately, or sequentially.

3. A pharmaceutical composition, comprising a pharmaceutical carrier and a compound according to claim 1.

4. A method for inhibiting a proteasome comprising contacting the proteasome with a compound according to claim 1.

5. A method for treating solid tumors or blood tumors in a subject comprising administering to the subject an amount of a compound according to claim 1 effective to treat the solid tumors or blood tumors.

6. The method of claim 5 for treating solid tumors, wherein the tumor is non-small cell lung cancer, small cell lung cancer, lung adenocarcinoma, lung squamous cell carcinoma, pancreatic cancer, breast cancer, prostate cancer, liver cancer, skin cancer, epithelial cell carcinoma, gastrointestinal stromal tumor, or nasopharyngeal carcinoma.

7. The method of claim 5 for treating a blood tumors, wherein the blood tumor is leukemia, multiple myeloma, mantle cell lymphoma or histiocytic lymphoma.

8. The compound or a pharmaceutically acceptable salt thereof according to claim 1, wherein the compound is one of:

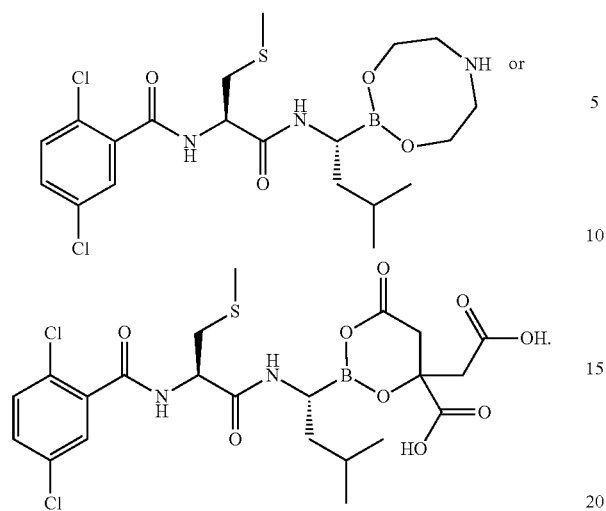
* * * * *